US011171295B2

(12) United States Patent
Ogawa et al.

(10) Patent No.: US 11,171,295 B2
(45) Date of Patent: Nov. 9, 2021

(54) ORGANIC ELECTROLUMINESCENT ELEMENT

(71) Applicant: NIPPON STEEL CHEMICAL & MATERIAL CO., LTD., Tokyo (JP)

(72) Inventors: Junya Ogawa, Tokyo (JP); Masashi Tada, Tokyo (JP); Yuji Ikenaga, Tokyo (JP)

(73) Assignee: NIPPON STEEL CHEMICAL & MATERIAL CO., LTD., Tokyo (JP)

(*) Notice: Subject to any disclaimer, the term of this patent is extended or adjusted under 35 U.S.C. 154(b) by 236 days.

(21) Appl. No.: 16/334,576

(22) PCT Filed: Jul. 27, 2017

(86) PCT No.: PCT/JP2017/027232
§ 371 (c)(1),
(2) Date: Mar. 19, 2019

(87) PCT Pub. No.: WO2018/061446
PCT Pub. Date: Apr. 5, 2018

(65) Prior Publication Data
US 2021/0083195 A1 Mar. 18, 2021

(30) Foreign Application Priority Data
Sep. 30, 2016 (JP) .............................. JP2016-194097

(51) Int. Cl.
*H01L 51/00* (2006.01)
*C09K 11/06* (2006.01)
*H01L 51/50* (2006.01)

(52) U.S. Cl.
CPC .......... *H01L 51/0067* (2013.01); *C09K 11/06* (2013.01); *H01L 51/001* (2013.01);
(Continued)

(58) Field of Classification Search
CPC ............. H01L 51/0067; H01L 51/0085; H01L 51/0072; C09K 11/06; C09K 2211/1029
See application file for complete search history.

(56) References Cited

U.S. PATENT DOCUMENTS

2014/0197386 A1 7/2014 Kim et al.
2014/0306207 A1 10/2014 Nishimura et al.
(Continued)

FOREIGN PATENT DOCUMENTS

WO WO 2011/136755 A1 11/2011
WO WO 2014/050588 A1 4/2014
(Continued)

OTHER PUBLICATIONS

English translation of International Preliminary Report on Patentability and Written Opinion dated Apr. 11, 2019, in PCT/JP2017/027232 (Forms PCT/IB338, PCT/IB/373, and PCT/ISA237.
(Continued)

*Primary Examiner* — Anthony Ho
(74) *Attorney, Agent, or Firm* — Birch, Stewart, Kolasch & Birch, LLP

(57) ABSTRACT

Provided is an organic electroluminescent (organic EL) element that exhibits a high efficiency while having a low drive voltage, and that exhibits a high stability while being driven. The organic electroluminescent element contains, in a light-emitting layer formed between an anode and a cathode opposing each other, a first host selected from indolocarbazole compounds represented by general formula (Continued)

(1), a second host selected from carbazole compounds represented by general formula (2), and a light-emitting dopant material. Here, $Ar^2$ and $Ar^3$ are aromatic hydrocarbon groups, $L^1$ is a direct bond or a phenylene group, and $L^2$ is an o-phenylene group.

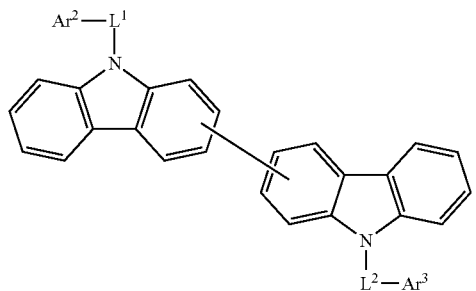

16 Claims, 1 Drawing Sheet

(52) U.S. Cl.
CPC ...... *H01L 51/0072* (2013.01); *H01L 51/0085* (2013.01); *C09K 2211/1029* (2013.01); *C09K 2211/185* (2013.01); *H01L 51/5012* (2013.01); *H01L 51/5016* (2013.01); *H01L 51/5096* (2013.01); *H01L 2251/5384* (2013.01)

(56) References Cited

U.S. PATENT DOCUMENTS

| | | |
|---|---|---|
| 2014/0374728 A1 | 12/2014 | Adamovich et al. |
| 2015/0001488 A1 | 1/2015 | Min et al. |
| 2015/0236262 A1 | 8/2015 | Cho et al. |
| 2017/0213968 A1* | 7/2017 | Park ........................ H05B 33/20 |
| 2017/0263869 A1 | 9/2017 | Tada et al. |

FOREIGN PATENT DOCUMENTS

| | | |
|---|---|---|
| WO | WO 2013/062075 A1 | 4/2015 |
| WO | WO 2015/156587 A1 | 10/2015 |
| WO | WO 2016/010402 A1 | 1/2016 |
| WO | WO 2016/013867 A1 | 1/2016 |
| WO | WO 2016/013875 A | 1/2016 |
| WO | WO 2016/042997 A1 | 6/2017 |

OTHER PUBLICATIONS

English translation of International Search Report dated Oct. 24, 2017, in PCT/JP2017/027232.

* cited by examiner

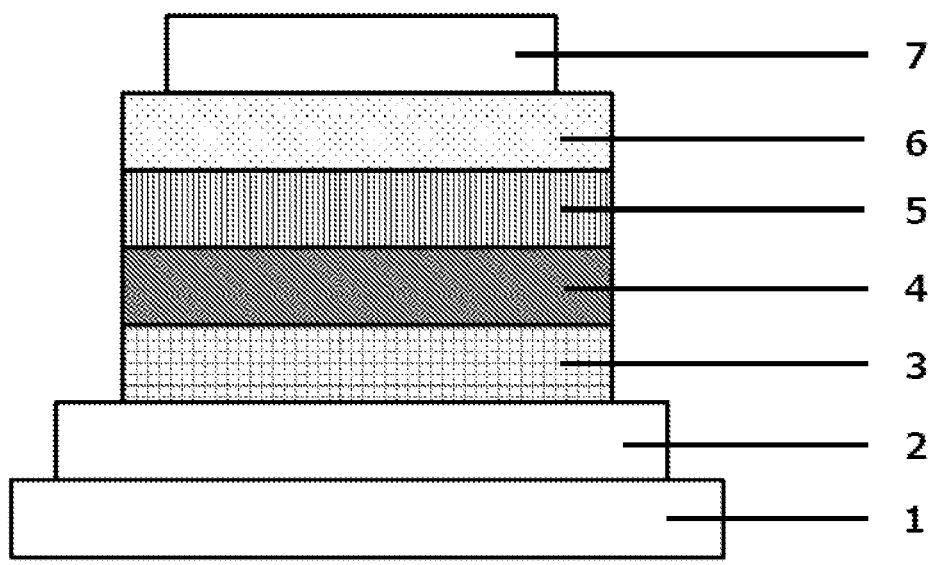

ORGANIC ELECTROLUMINESCENT ELEMENT

TECHNICAL FIELD

The present invention relates to an organic electroluminescent element (organic EL element). More particularly, the present invention relates to an organic EL element that contains a first host, a second host, and a light-emitting dopant material.

BACKGROUND ART

Upon the application of voltage to an organic EL element, holes are injected into the light-emitting layer from the anode and electrons are injected into the light-emitting layer from the cathode. The injected holes and electrons then recombine in the light-emitting layer to form excitons. Based on statistical rules for electron spin, singlet excitons and triplet excitons are produced at this point at a 1:3 ratio. Fluorescent organic EL elements, which use emission based on singlet excitons, are thus regarded as having a limit of 25% for the internal quantum efficiency. On the other hand, phosphorescent organic EL elements, which use emission based on triplet excitons, are known to have an internal quantum conversion that can be increased to 100% when intersystem conversion from singlet excitons is efficiently carried out.

However, extending the life of phosphorescent organic EL elements has been a technical problem.

In addition, high-efficiency organic EL elements that utilize delayed fluorescence have been developed quite recently. For example, PTL 1 discloses an organic EL element that utilizes the triplet-triplet fusion (TTF) mechanism, which is one mechanism of delayed fluorescence. The TTF mechanism utilizes a phenomenon in which a singlet exciton is produced by the collision of two triplet excitons, and the theoretical internal quantum conversion is thought to be increased to 40%. However, the efficiency is lower than in phosphorescent organic EL elements, and as a consequence additional improvements in efficiency are required.

PTL 2, on the other hand, discloses an organic EL element that utilizes a thermally activated delayed fluorescence (TADF) mechanism. The TADF mechanism utilizes a phenomenon in which reverse intersystem crossing from a triplet exciton to a singlet exciton is produced in a material that exhibits a small energy difference between the singlet level and triplet level, and it is thought that the theoretical internal quantum conversion here may be increased to 100%. However, as with phosphorescent elements, additional improvements in the life characteristics are required.

CITATION LIST

Patent Literature

[PTL 1] WO 2010/134350A
[PTL 2] WO 2011/070963A
[PTL 3] WO 2008/056746A
[PTL 4] Japanese Patent Application Laid-open No. 2003-133075
[PTL 5] WO 2013/062075A
[PTL 6] US 2014/0374728A
[PTL 7] US 2014/0197386A
[PTL 8] US 2015/0001488A
[PTL 9] US 2015/0236262A
[PTL 10] WO 2011/136755A The use of indolocarbazole compounds as a host material is disclosed in PTL 3. The use of biscarbazole compounds as a host material is disclosed in PTL 4.

PTL 5 and 6 disclose the use of a biscarbazole compound for a mixed host. PTL 7, 8, and 9 disclose the use of an indolocarbazole compound and a biscarbazole compound as a mixed host.

PTL 10 discloses the use of a host material provided by the premixing of a plurality of hosts that include an indolocarbazole compound.

However, none of these can be regarded as satisfactory and further improvement is desired.

SUMMARY OF INVENTION

The application of organic EL elements to display devices, e.g., flat panel displays, and light sources requires that the emission efficiency of the element be improved and that at the same time the stability while being driven is satisfactorily secured. Considering these circumstances, an object of the present invention is to provide a practically useful organic EL element that exhibits a high efficiency while having a low drive voltage, and that exhibits a high stability while being driven.

The present invention is an organic EL element that contains one or more light-emitting layers between an anode and a cathode opposing each other, wherein at least one light-emitting layer produced by vacuum vapor deposition contains a first host selected from compounds represented by the following general formula (1), a second host selected from compounds represented by the following general formula (2), and a light-emitting dopant material.

[C1]

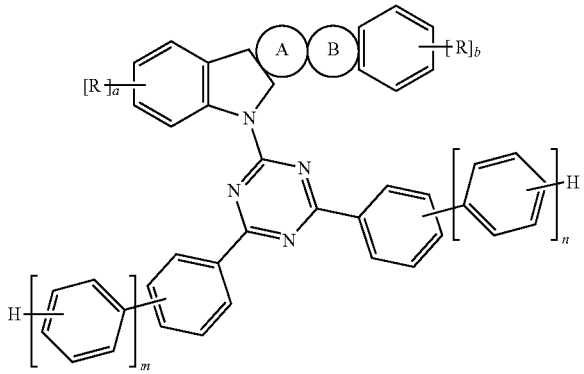

(1)

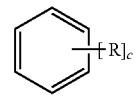

(1a)

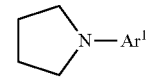

(1b)

(Here, ring A is an aromatic hydrocarbon ring represented by formula (1a), ring B is a heterocycle represented by formula (1b), and ring A and ring B are each fused at any position with rings adjacent thereto;

$Ar^1$ is a phenyl group, a biphenyl group, or a terphenyl group;

each R is independently an aliphatic hydrocarbon group having 1 to 10 carbons, an aromatic hydrocarbon group having 6 to 10 carbons, or an aromatic heterocyclic group having 3 to 12 carbons;

a, b, and c represent the number of substituents and each independently represents an integer of 0 to 3; and m and n represent the number of repetitions and each independently represents an integer of 0 to 2)

[C2]

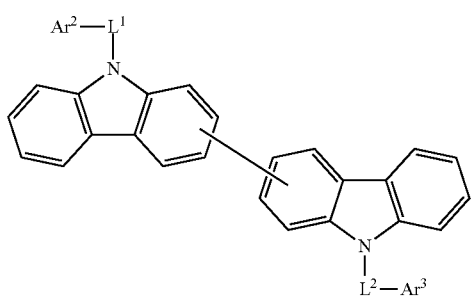

(2)

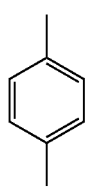

(2a)

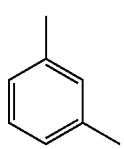

(2b)

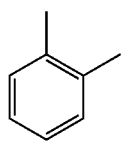

(2c)

(Here, $Ar^2$ and $Ar^3$ represent an aromatic hydrocarbon group having 6 to 14 carbons or a group in which two of the foregoing aromatic hydrocarbon groups are linked to each other, wherein the two aromatic hydrocarbon groups linked to each other may be the same or may differ. $L^1$ represents a direct bond or a phenylene group of formula (2a), formula (2b), or formula (2c), and $L^2$ represents a divalent phenylene group of formula (2c).)

General formula (3) is a preferred aspect of general formula (2) and general formula (4) is a more preferred aspect.

[C3]

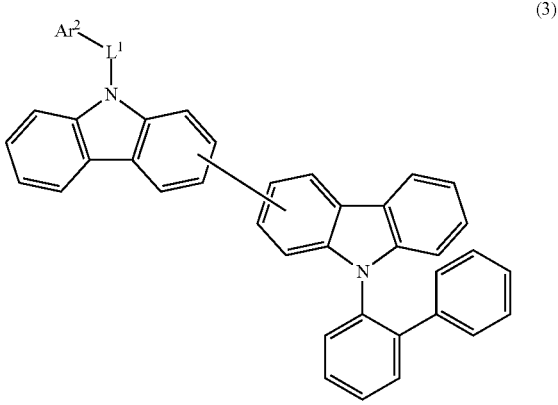

$Ar^2$ and $L^1$ in general formulas (3) and (4) are defined as for $Ar^2$ and $L^1$ in general formula (2).

The first host and the second host are preferably used after premixing prior to vapor deposition. In addition, the difference between the 50% weight loss temperatures of the first host and the second host is preferably within 20° C., and the proportion of the first host with reference to the sum of the first host and second host is preferably greater than 20 wt % and less than 55 wt %.

The light-emitting dopant material can be a phosphorescent dopant material, a fluorescent dopant material, or a thermally activated delayed fluorescence light-emitting dopant material. An organometal complex that contains at least one metal selected from ruthenium, rhodium, palladium, silver, rhenium, osmium, iridium, platinum, and gold is an example of the phosphorescent dopant material.

In addition, the organic EL element can have a hole blocking layer disposed adjacent to the light-emitting layer, and a compound represented by general formula (1) can be incorporated in this hole blocking layer.

In order to improve the characteristics of the element, the materials used for the organic layer must exhibit a high ability to withstand charge, and in particular the inhibition of exciton and charge leakage from the light-emitting layer to surrounding layers is crucial. Improving the segregation of the light-emitting regions in the light-emitting layer is effective for inhibiting this charge/exciton leakage, and due to this control of the amount of injection of the two charges (electron/hole) into the light-emitting layer—or of the amount of transport of the two charges in the light-emitting layer—into a preferred range is crucial.

The indolocarbazole compounds represented by general formula (1) have a very stable skeleton and, through their isomers and substituents, enable a certain amount of control of the injection and transport properties of the two charges; however, it is difficult using these compounds by themselves to control the amount of injection/transport of the two charges into preferred ranges as referenced above. On the other hand, the biscarbazole compounds represented by general formula (2) enable, based on alterations in the type and number of substituents, a high level of control of the charge injection/transport properties and in addition have the same high skeleton stability as the indolocarbazole compounds. As a consequence, through the use of a mixture of the indolocarbazole compound and this biscarbazole compound, the amount of charge injection into the organic layer can be more precisely regulated than is the case for the individual use of either. In the particular case of use in the light-emitting layer of a delayed fluorescence light-emitting EL element or a phosphorescent light-emitting EL element, a lowest excited triplet energy is exhibited that is high enough to confine the excitation energy produced at the light-emitting layer, and because of this energy outflow from within the light-emitting layer does not occur and a high efficiency at low voltages and a long life can be achieved.

BRIEF DESCRIPTION OF DRAWINGS

FIG. 1 is a schematic cross-sectional diagram that shows an example of an organic EL element.

DESCRIPTION OF EMBODIMENTS

The organic EL element according to the present invention contains, between an anode and a cathode opposing each other, one or more light-emitting layers, wherein at least one such layer is produced by vacuum vapor deposition and contains a first host, a second host, and a light-emitting dopant material. The first host is a compound represented by general formula (1), and the second host is a compound represented by general formula (2). This organic EL element has an organic layer comprising a plurality of layers between the anode and cathode opposing each other, and at least one layer of the plurality of layers is a light-emitting layer and a plurality of light-emitting layers may be present.

General formula (1) will now be described.

Ring A is an aromatic hydrocarbon ring represented by formula (1a); ring B is a heterocycle represented by formula (1b); and ring A and ring B are each fused at any position with rings adjacent thereto.

$Ar^1$ represents a phenyl group, a biphenyl group, or a terphenyl group. A phenyl group and a biphenyl group are preferred while a phenyl group is more preferred. Here, a biphenyl group is a group represented by -Ph-Ph, and a terphenyl group is a group represented by -Ph-Ph-Ph Ph or -Ph(-Ph)-Ph. This Ph is, e.g., a phenyl group or a phenylene group.

Each R is independently an aliphatic hydrocarbon group having 1 to 10 carbons, an aromatic hydrocarbon group having 6 to 10 carbons, or an aromatic heterocyclic group having 3 to 12 carbons. Aliphatic hydrocarbon groups having 1 to 8 carbons, a phenyl group, and aromatic heterocyclic groups having 3 to 9 carbons are preferred. Aliphatic hydrocarbon groups having 1 to 6 carbons, a phenyl group, and aromatic heterocyclic groups having 3 to 6 carbons are more preferred.

Specific examples of the aliphatic hydrocarbon groups having 1 to 10 carbons are methyl, ethyl, propyl, butyl, pentyl, hexyl, heptyl, octyl, nonyl, and decyl.

The aromatic hydrocarbon groups having 6 to 10 carbons and the aromatic heterocyclic groups having 3 to 12 carbons can be specifically exemplified by aromatic groups generated by removing one H from benzene, naphthalene, pyridine, pyrimidine, triazine, thiophene, isothiazole, triazole, pyridazine, pyrrole, pyrazole, imidazole, triazole, thiadiazole, pyrazine, furan, isoxazole, oxazole, oxadiazole, quinoline, isoquinoline, quinoxaline, quinazoline, thiadiazole, benzotriazine, phthalazine, tetrazole, indole, benzofuran, benzothiophene, benzoxazole, benzothiazole, indazole, benzimidazole, benzotriazole, benzisothiazole, benzothiadiazole, dibenzofuran, dibenzothiophene, dibenzoselenophene, and carbazole. Preferred are aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, oxadiazole, quinoline, isoquinoline, quinoxaline, quinazoline, thiadiazole, benzotriazine, phthalazine, tetrazole, indole, benzofuran, benzothiophene, benzoxazole, benzothiazole, indazole, benzimidazole, benzotriazole, benzisothiazole, and benzothiadiazole. More preferred are aromatic groups generated from benzene, pyridine, pyrimidine, triazine, thiophene, isothiazole, thiazole, pyridazine, pyrrole, pyrazole, imidazole, triazole, thiadiazole, pyrazine, furan, isoxazole, oxazole, and oxadiazole.

a, b, and c represent the number of substituents, and each independently represents an integer of 0 to 3, wherein an integer of 0 or 1 is preferred. m and n represent the number of repetitions, and each independently represents an integer of 0 to 2, wherein an integer of 0 or 1 is preferred. m+n is preferably 0 or an integer equal to or greater than 1 and is more preferably an integer of 1, 2, or 3.

Specific examples of the compounds represented by general formula (1) are given below, but there is no limitation to these exemplary compounds.

[C4]

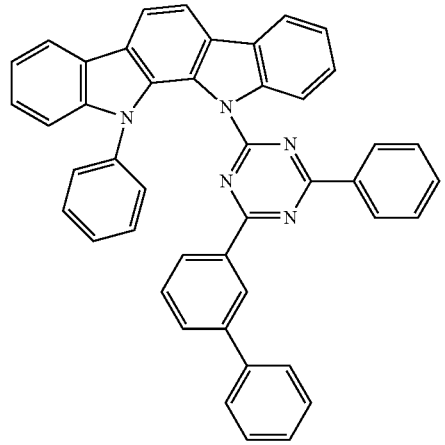

1-1

-continued
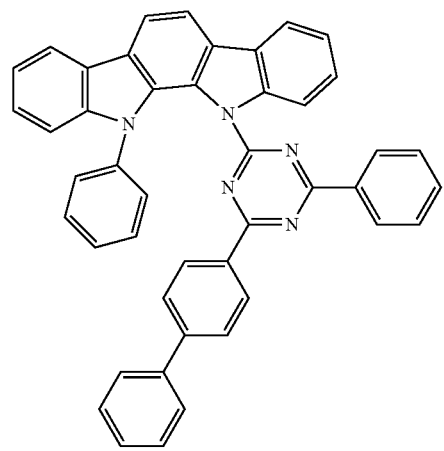
1-2
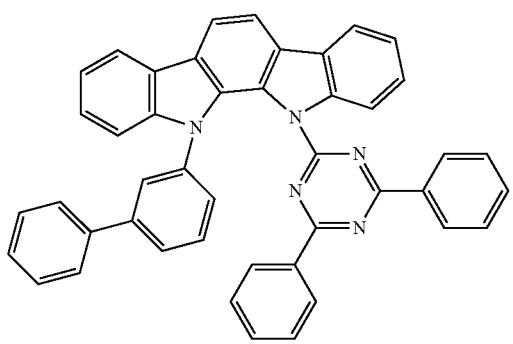
1-3
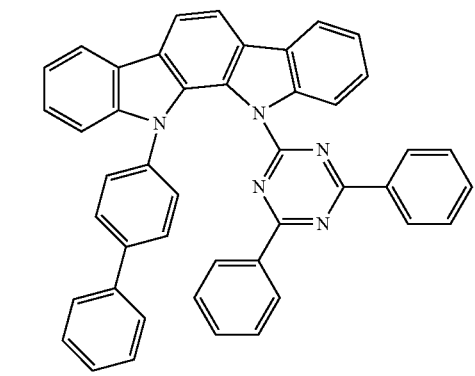
1-4
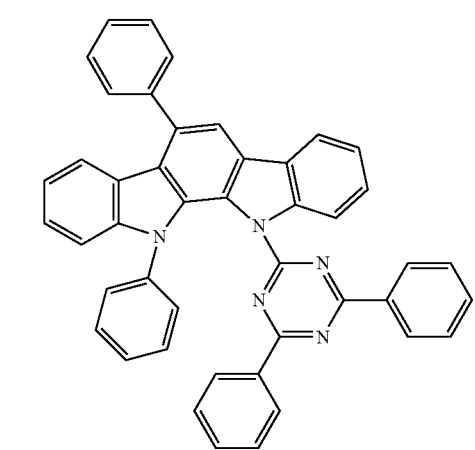
1-5
-continued
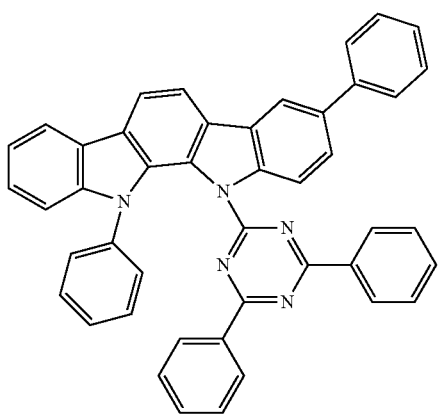
1-6
1-7
1-8
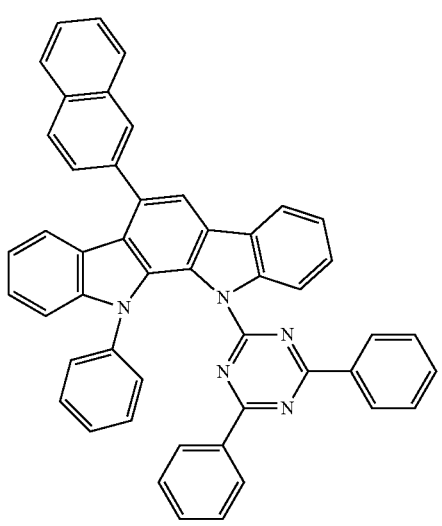

1-9
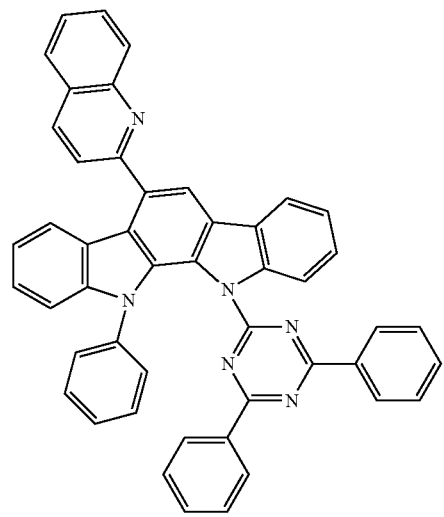
1-10
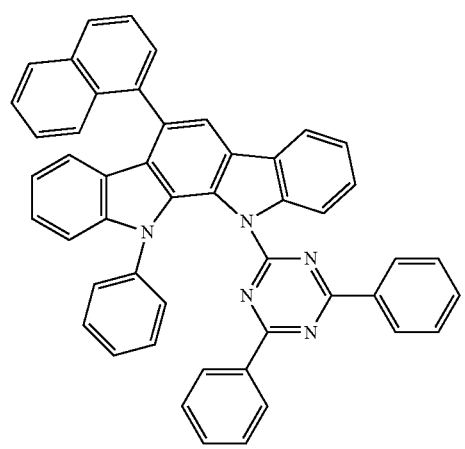
1-11
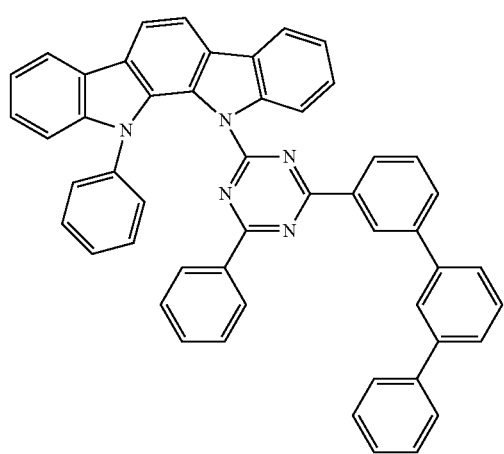
1-12
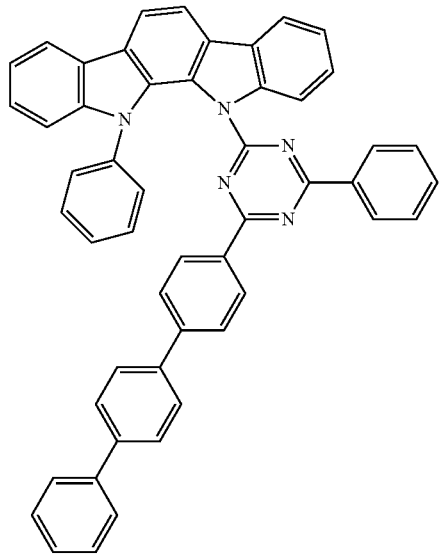
1-13
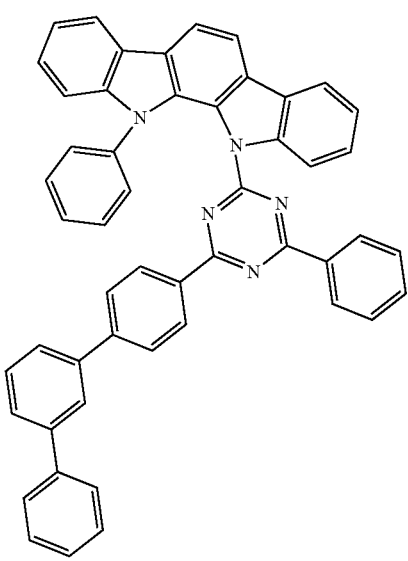
1-14
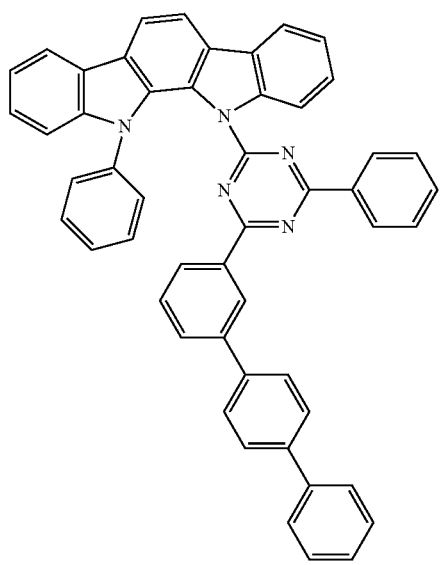

1-15
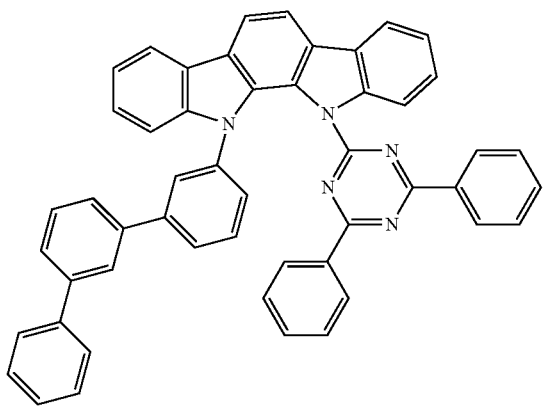
1-16
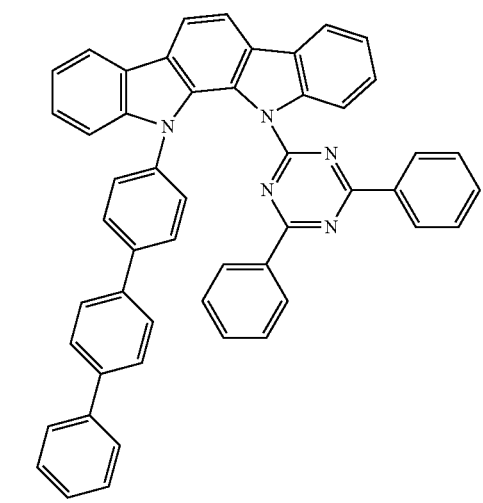
1-17
1-18
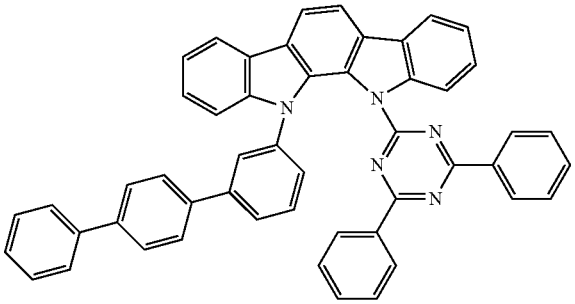
1-19
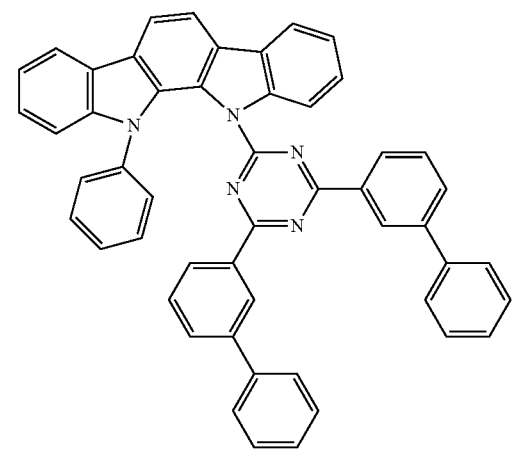
1-20
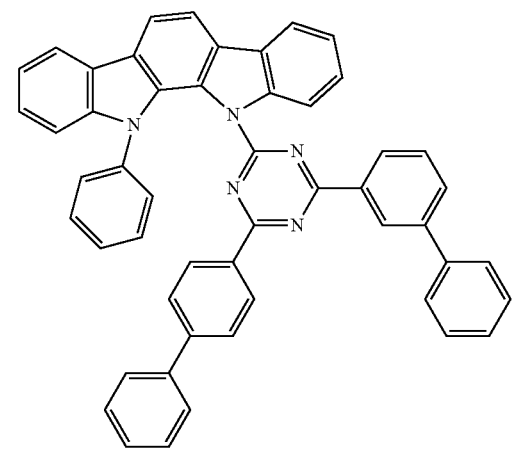

[C5]
1-21
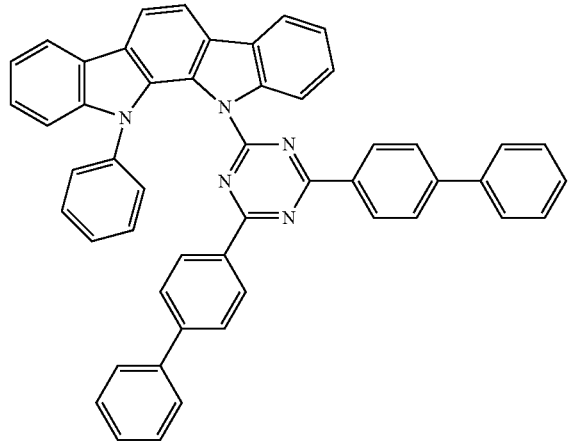
1-24
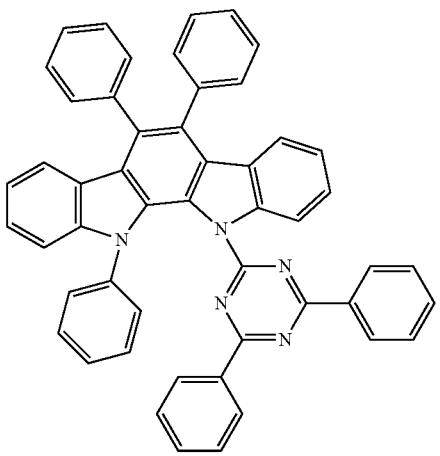
1-22
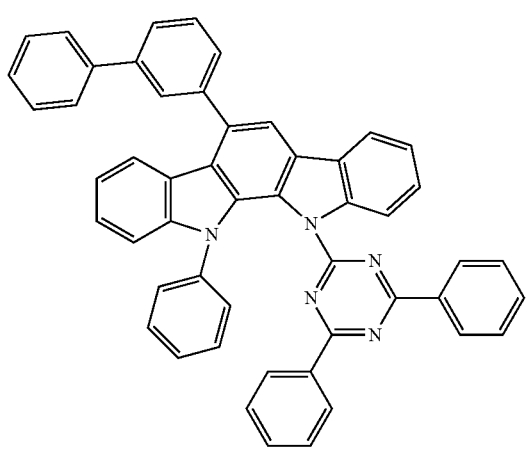
1-25
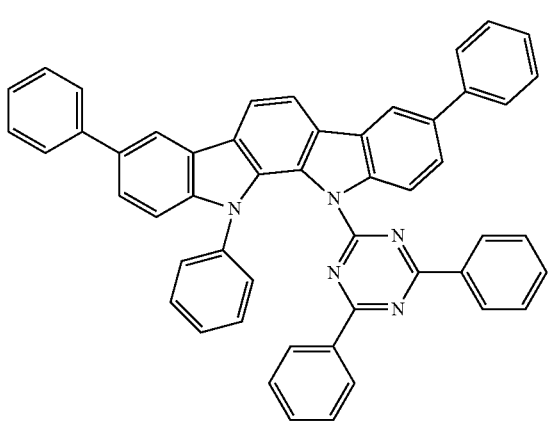
1-23
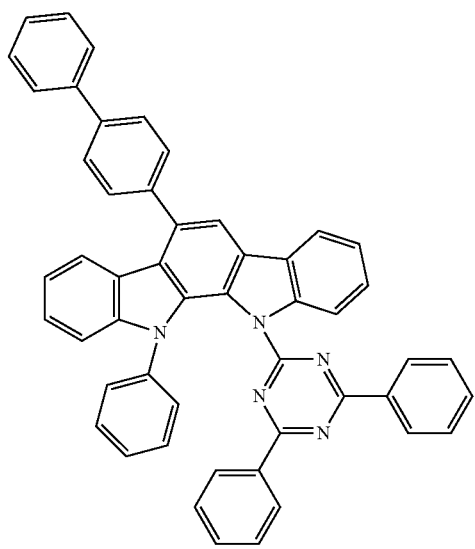
1-26
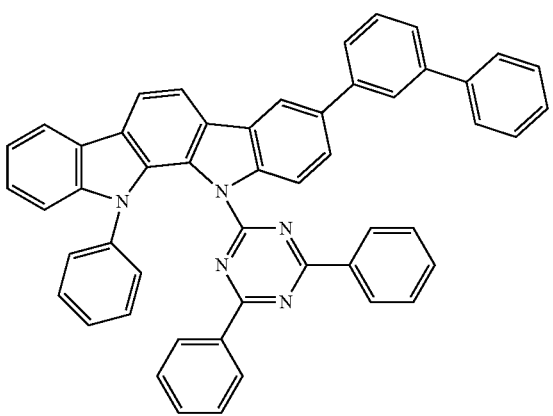

1-27
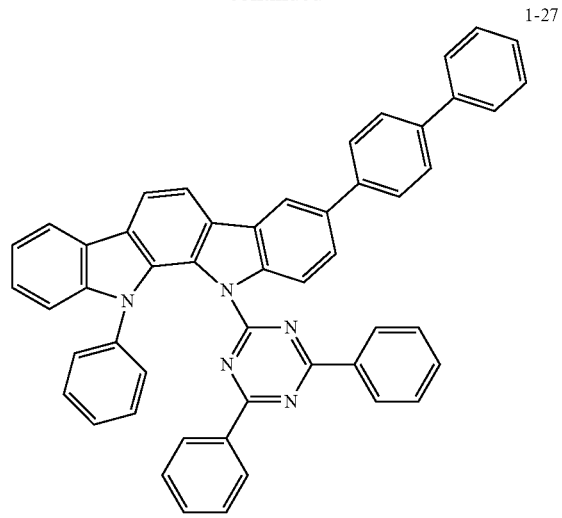
1-28
1-29
1-30
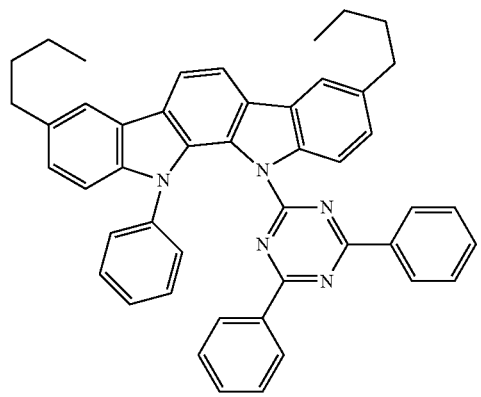
1-31
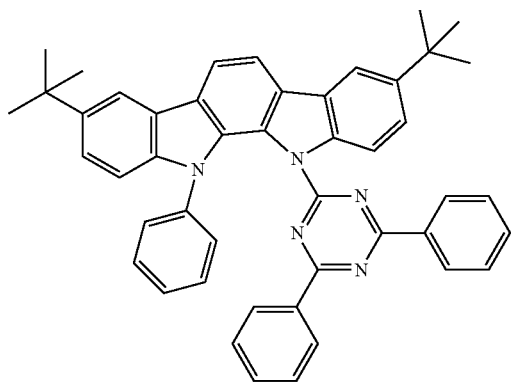
1-32
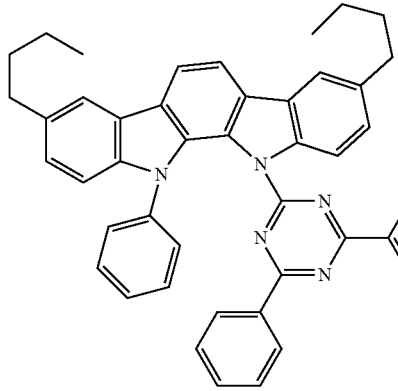
1-33
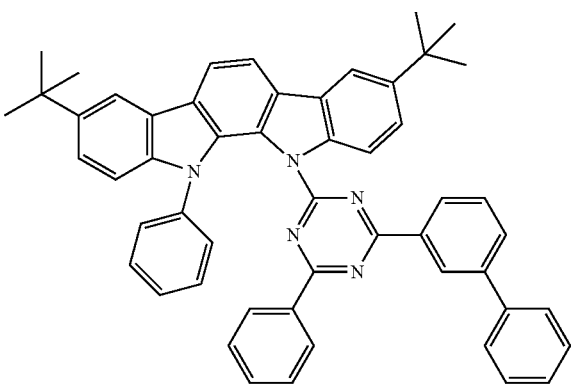

1-34
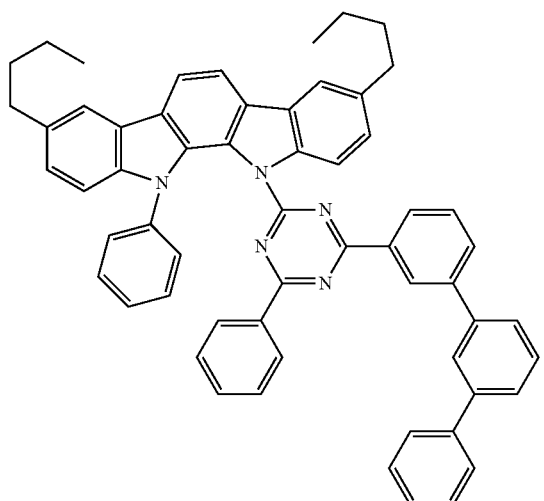
1-35
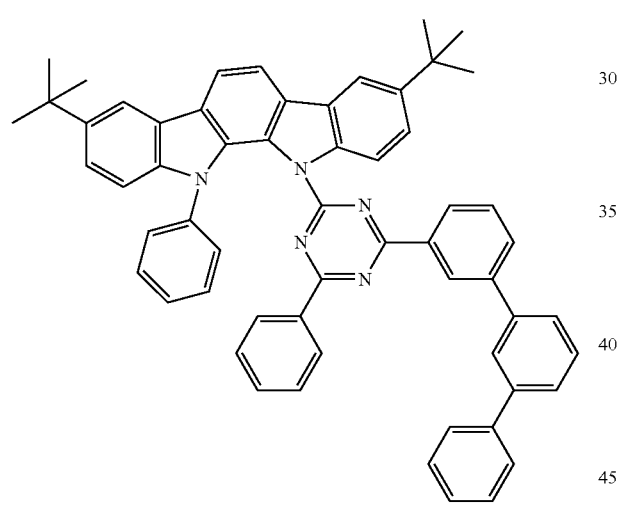
1-36
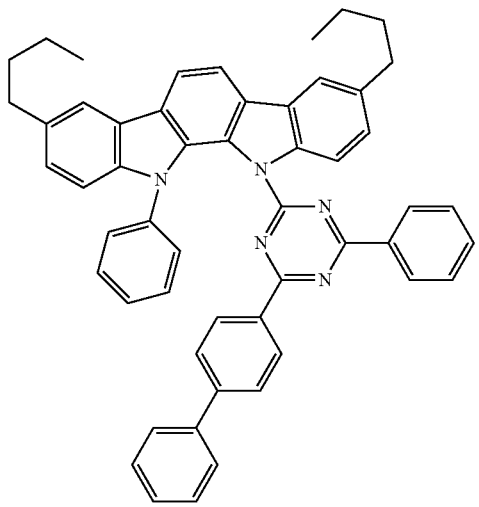
1-37
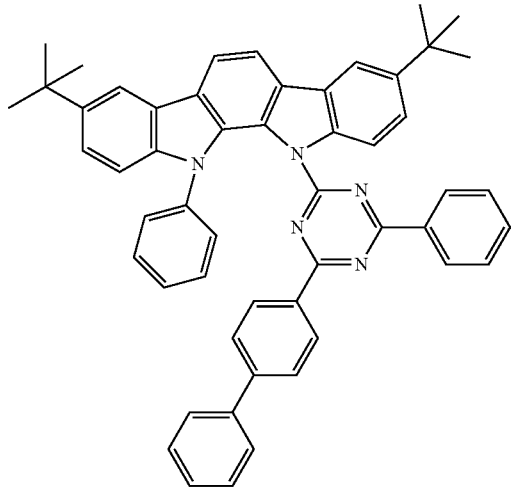
1-38
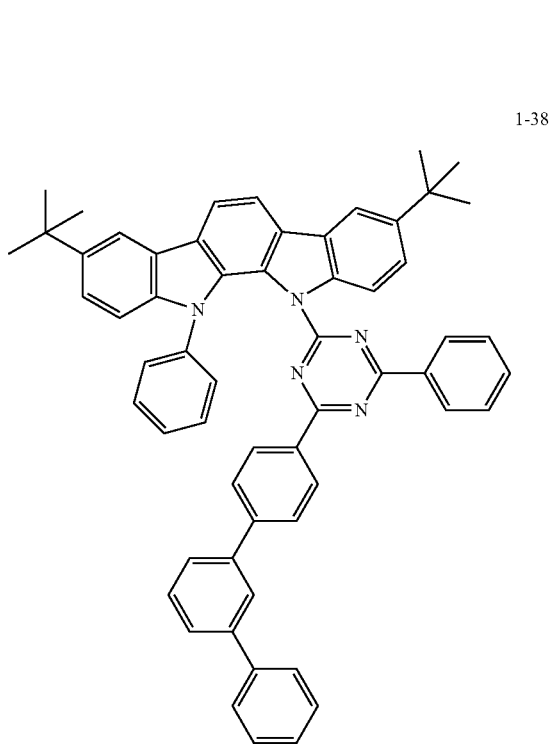

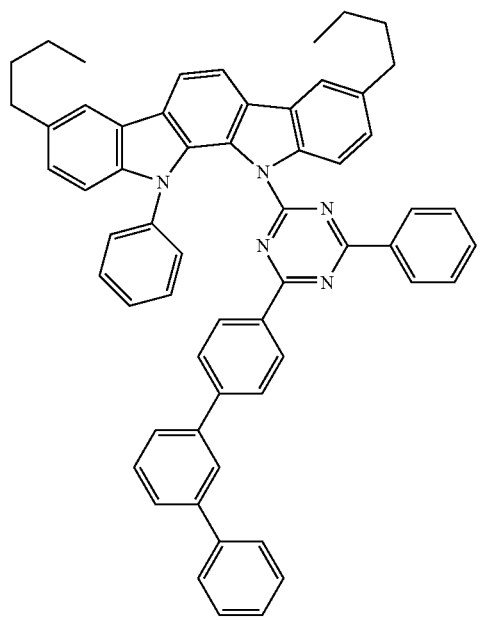
1-39
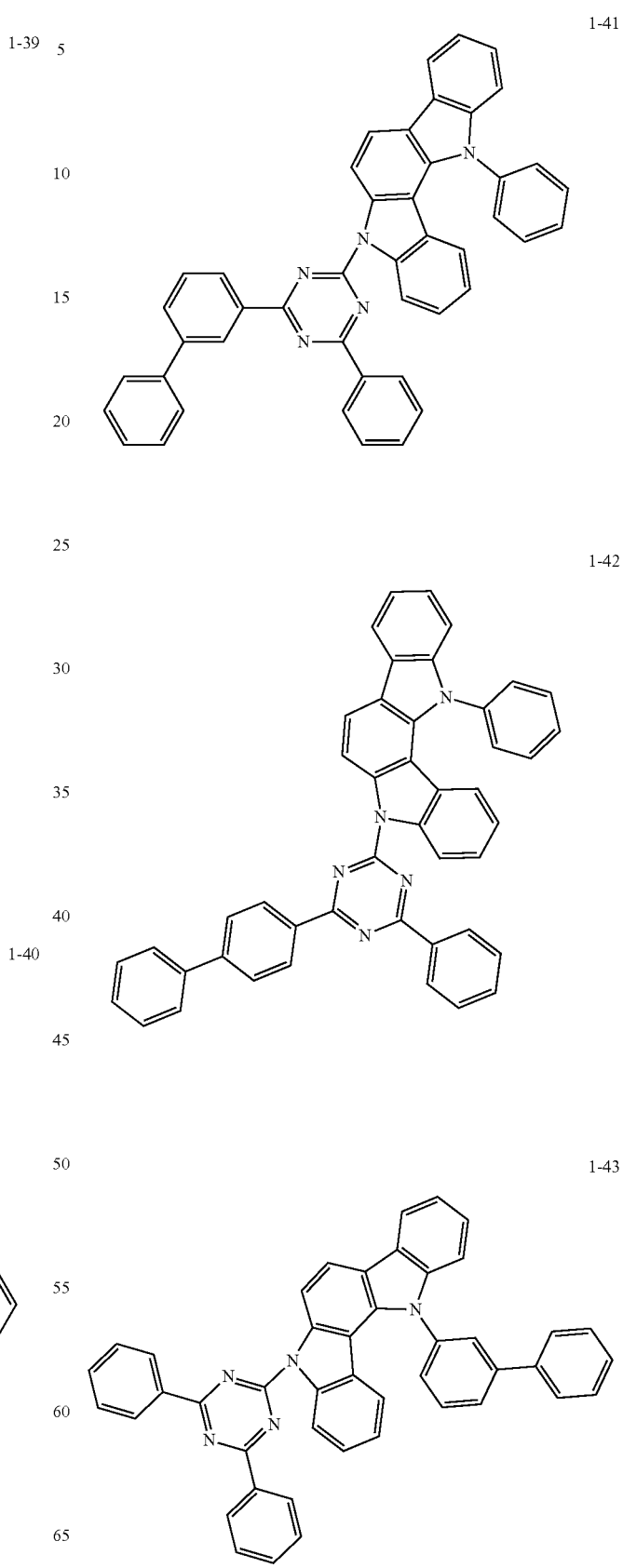

-continued
1-44
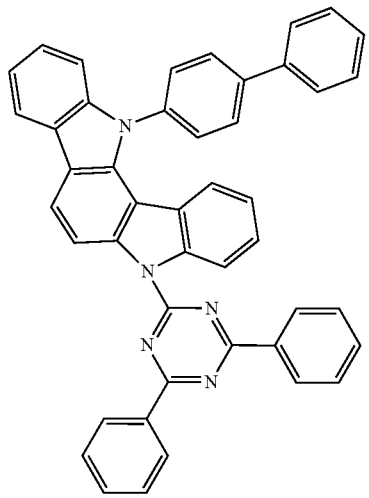
1-45
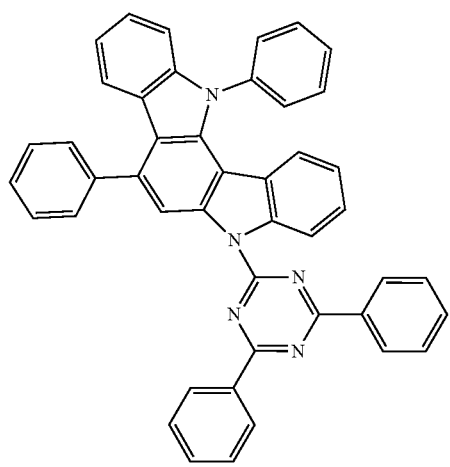
1-46
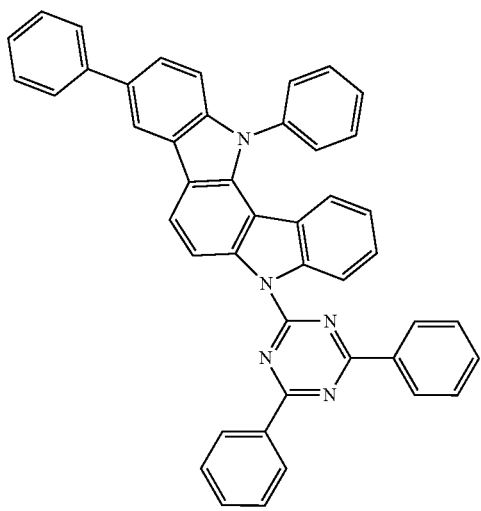
1-47
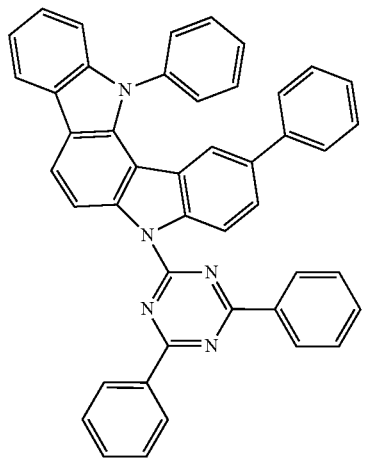
1-48
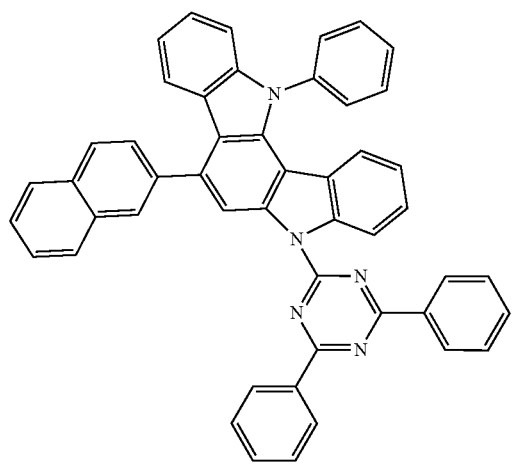
1-49
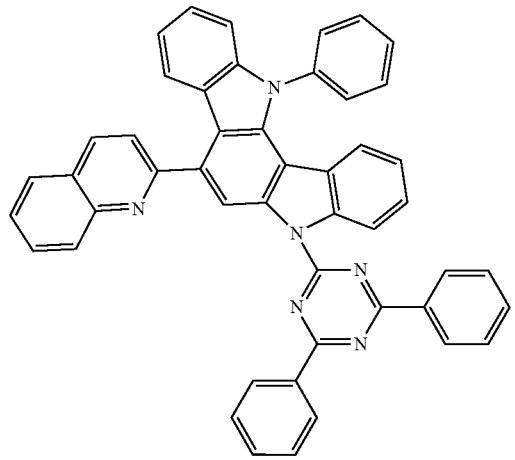

1-50
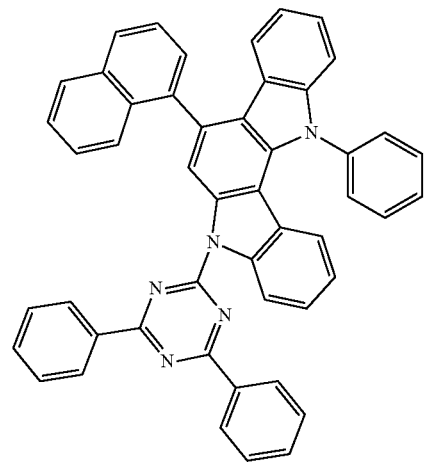
1-51
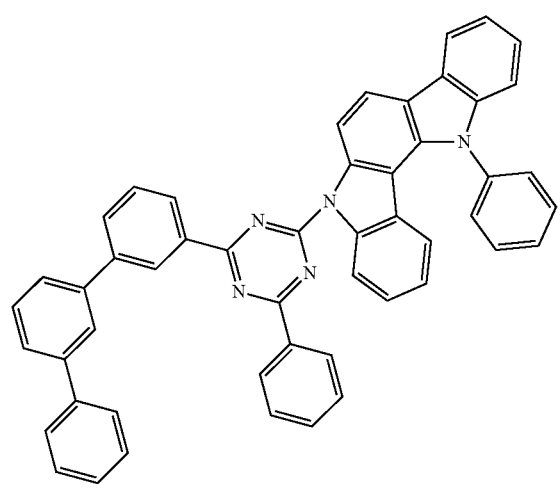
1-53
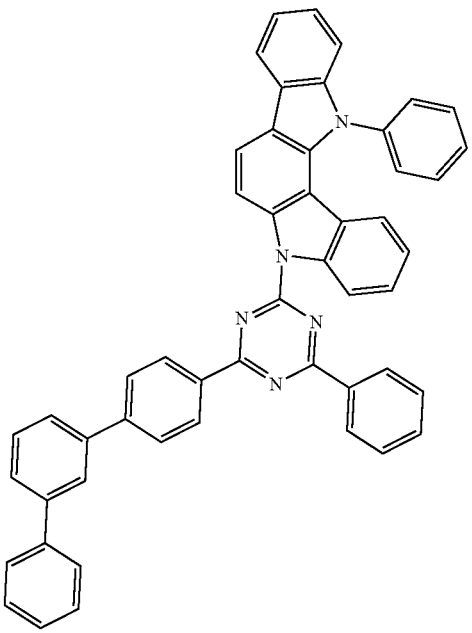
1-52
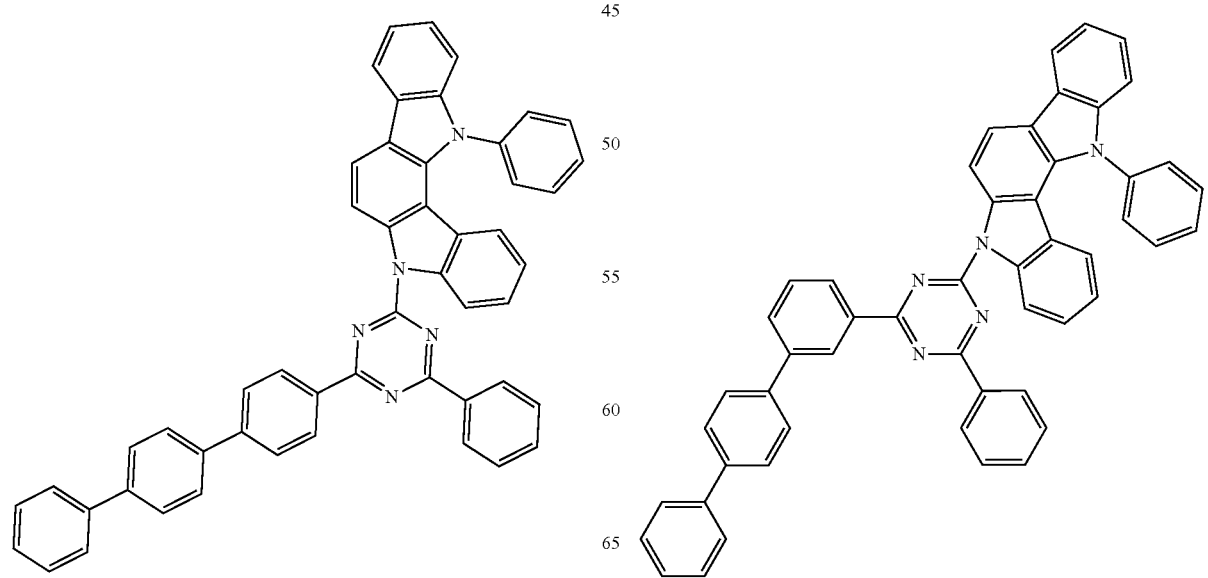
1-54

1-55
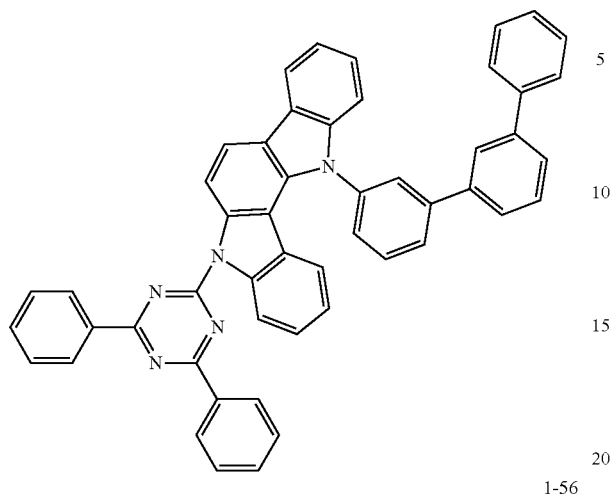
1-56
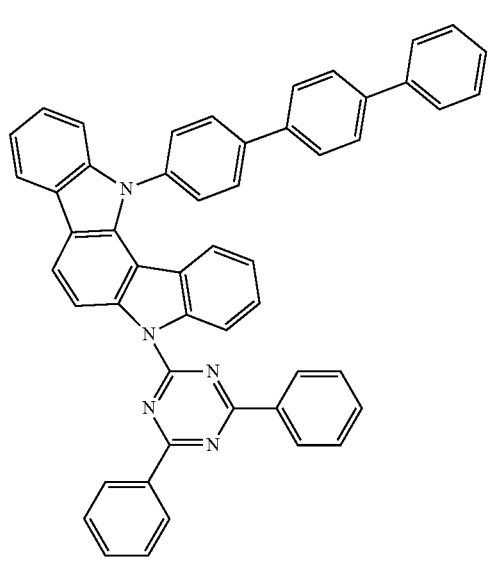
1-57
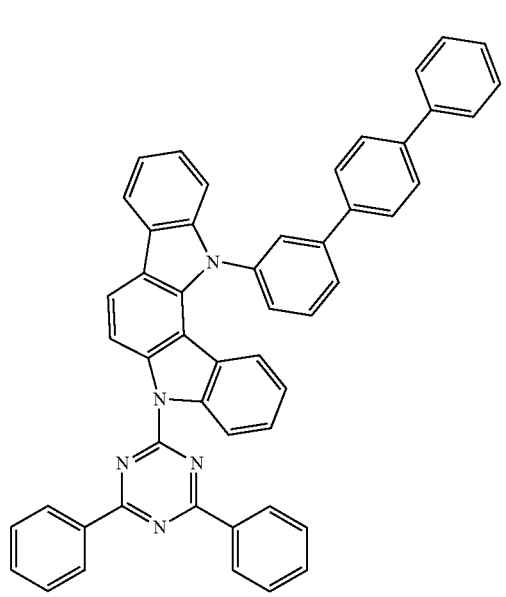
1-58
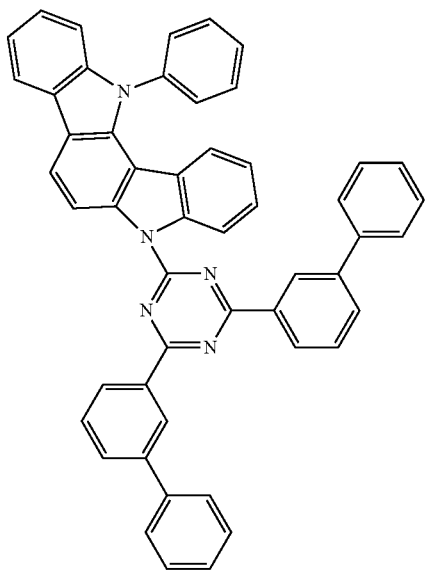
1-59
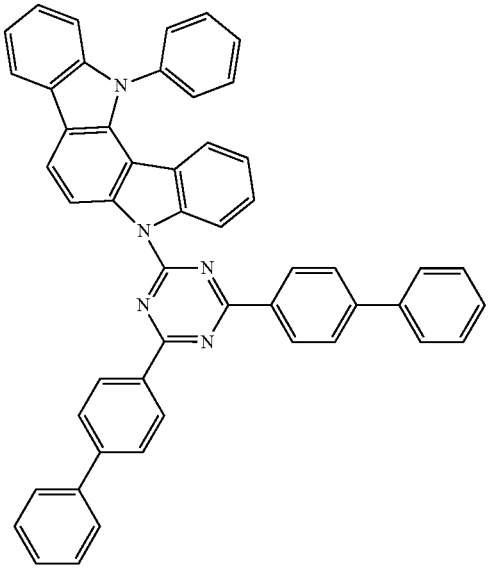

1-60
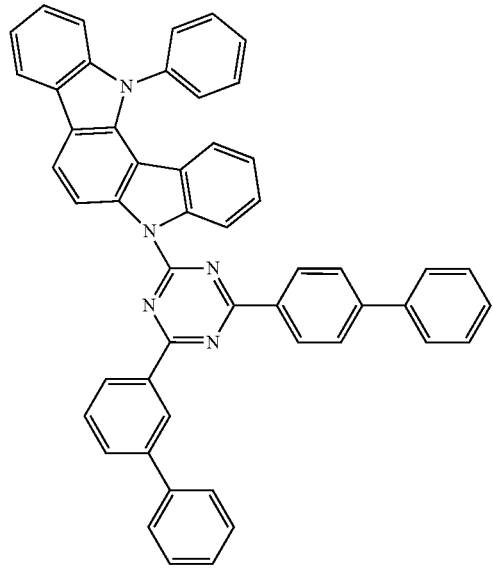
[C7]
1-61
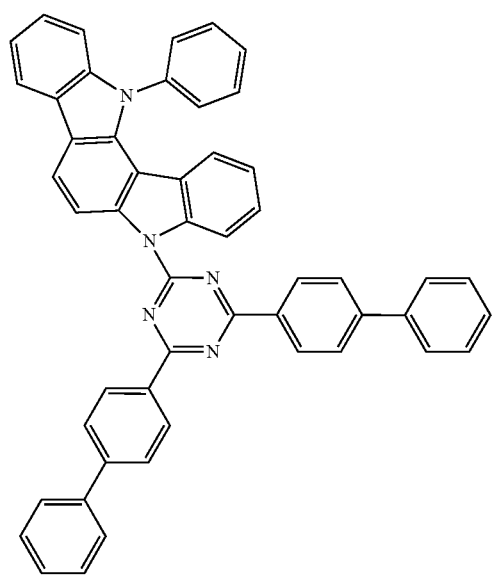
1-62
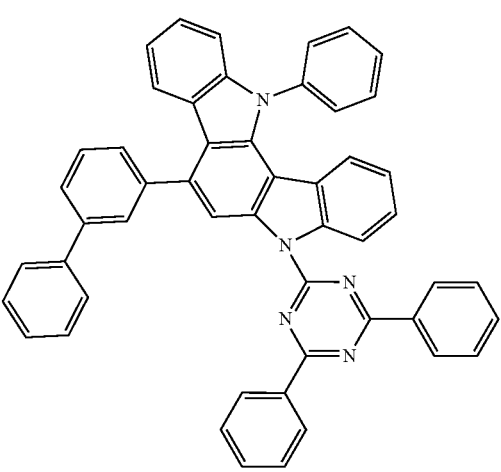
1-63
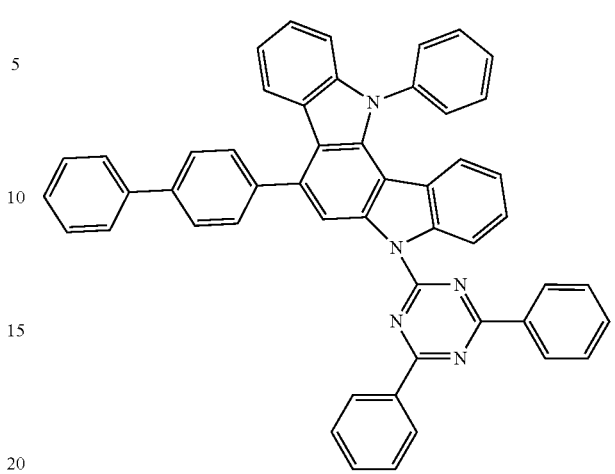
1-64
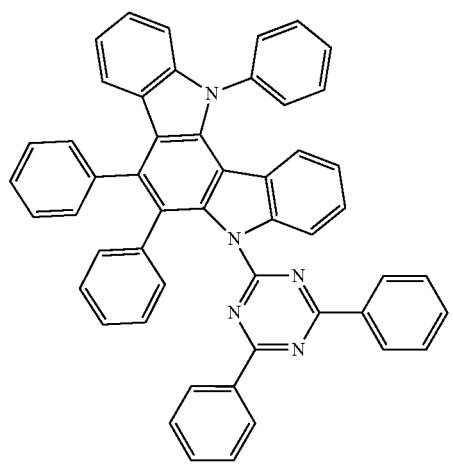
1-65
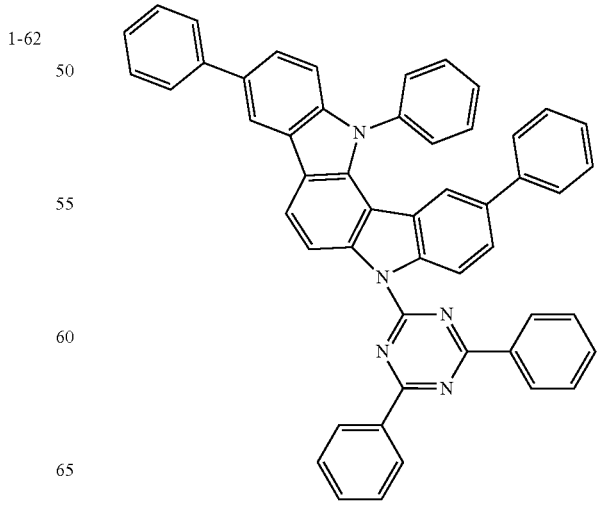

1-66
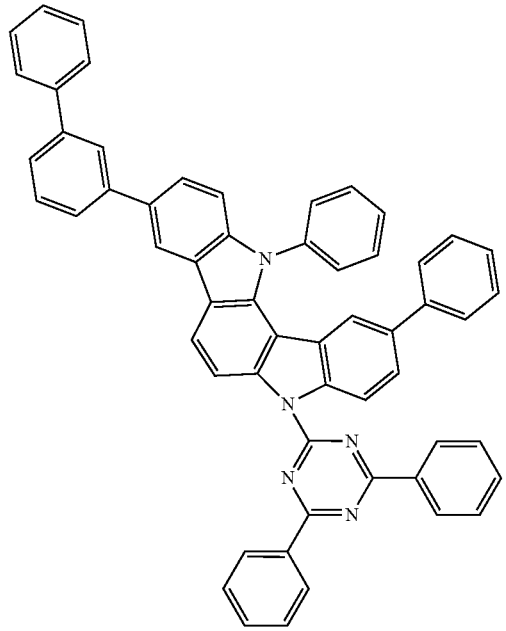
1-67
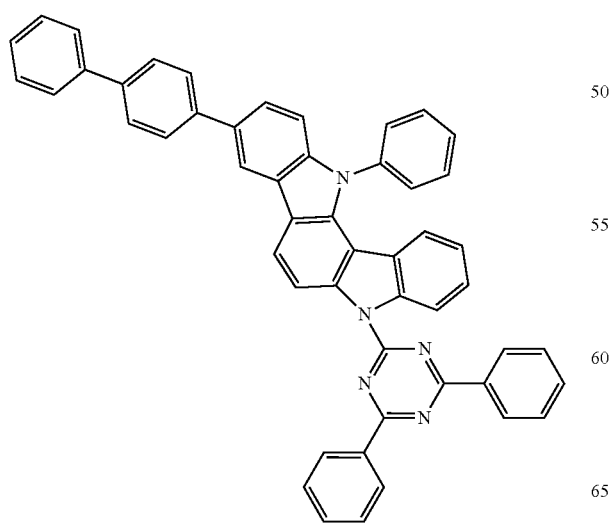
1-68
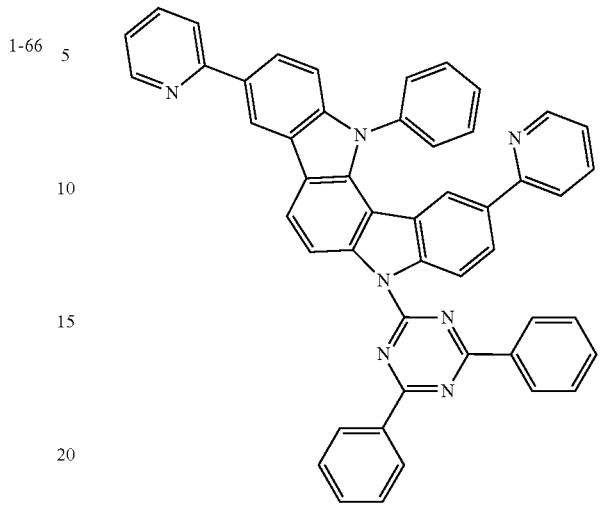
1-69
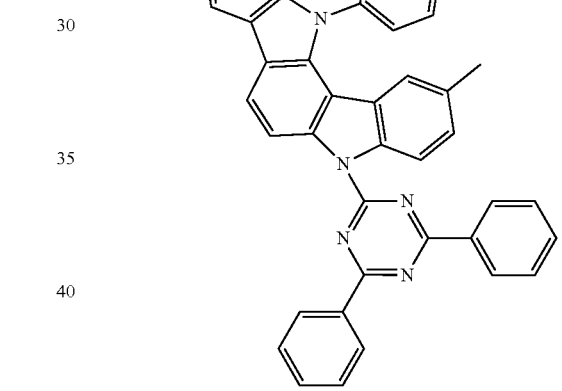
1-70
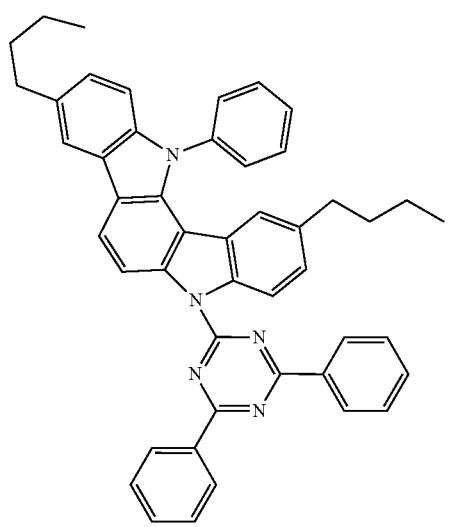

1-71
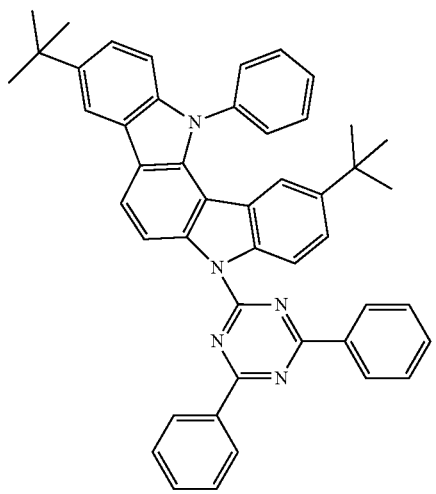
1-72
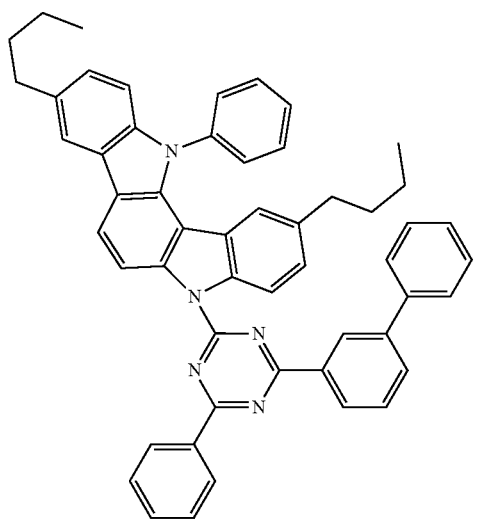
1-73
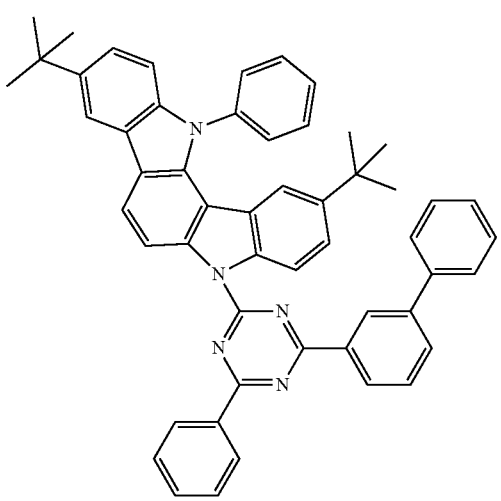
1-74
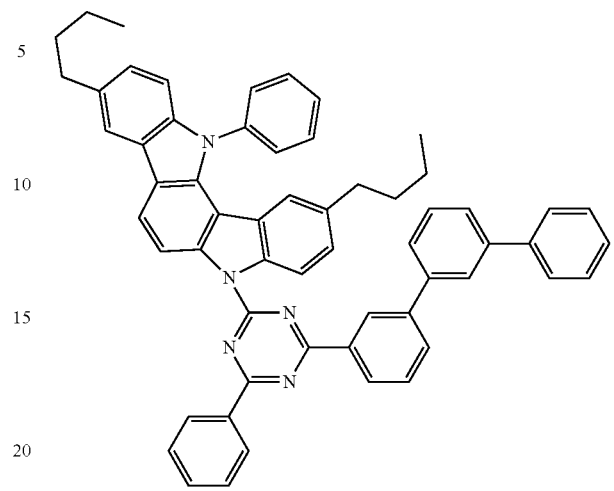
1-75
1-76
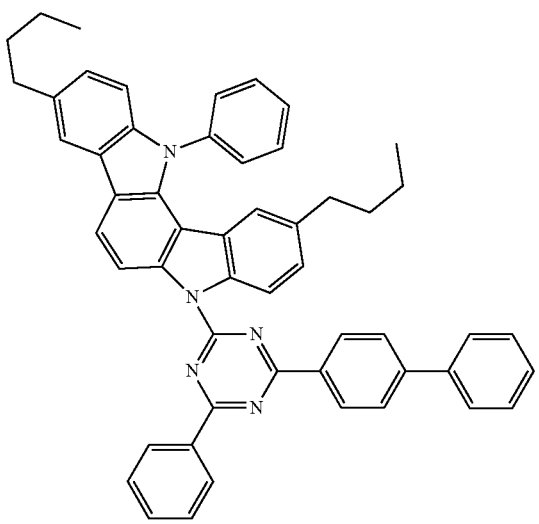

1-77
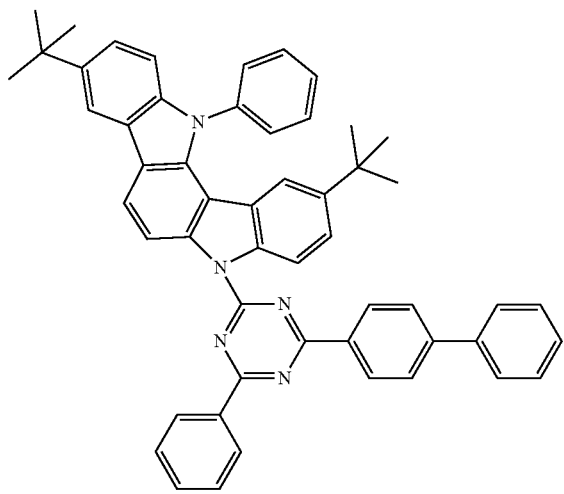
1-78
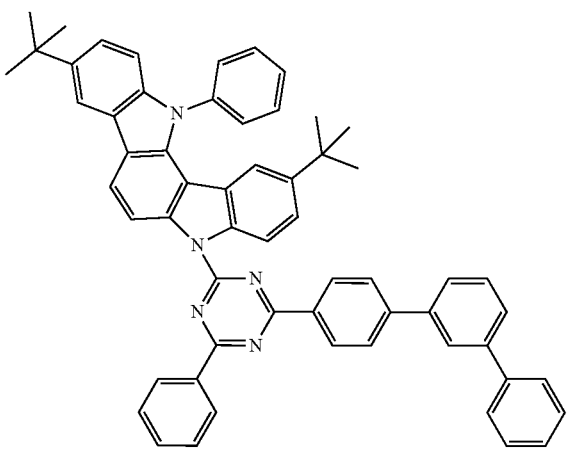
1-79
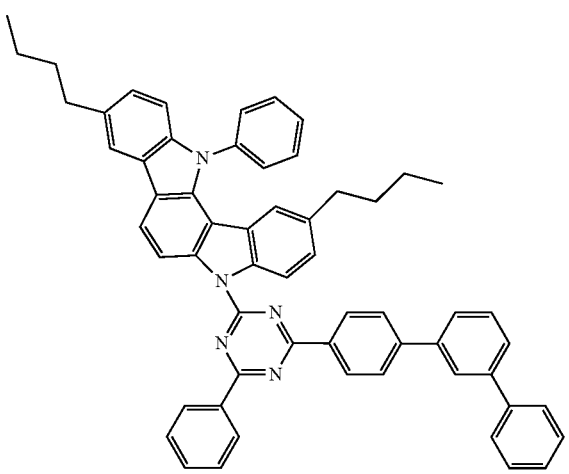
1-80
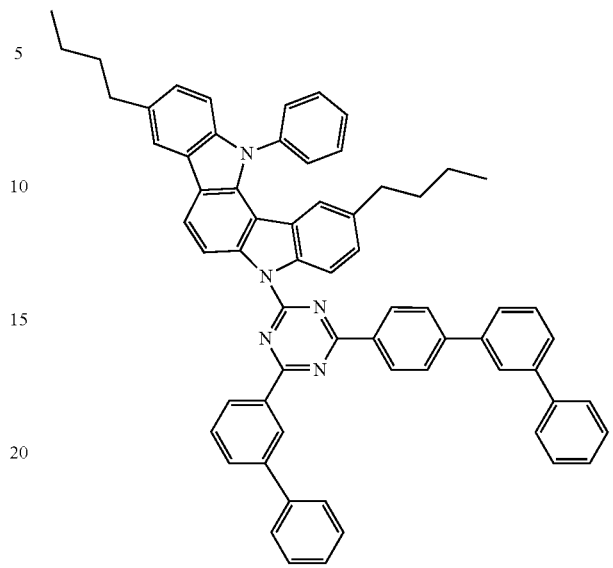
[C8]
1-81
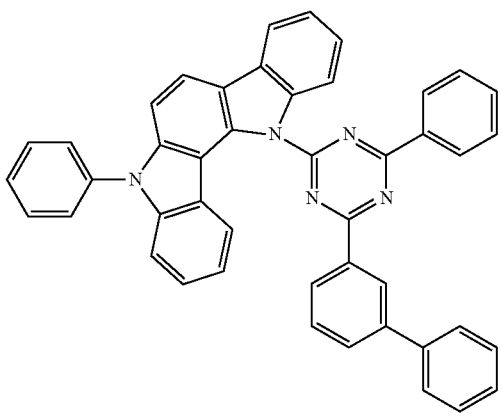
1-82
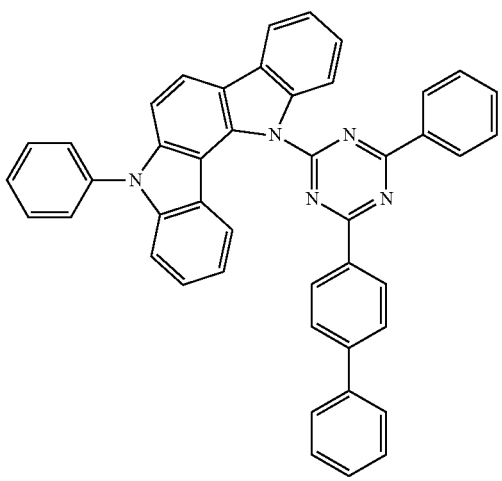

-continued
1-83
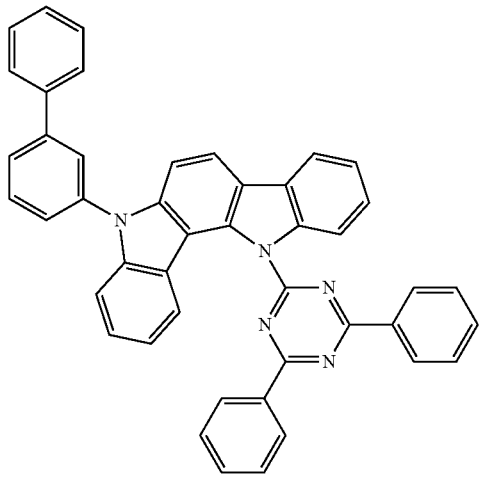
1-84
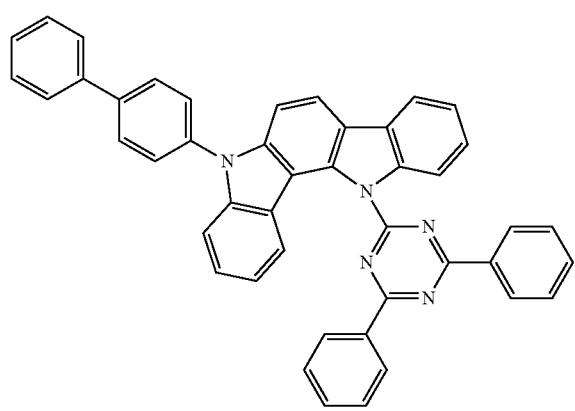
1-85
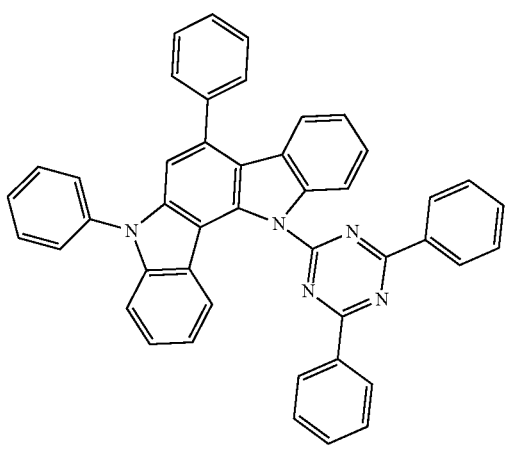
1-86
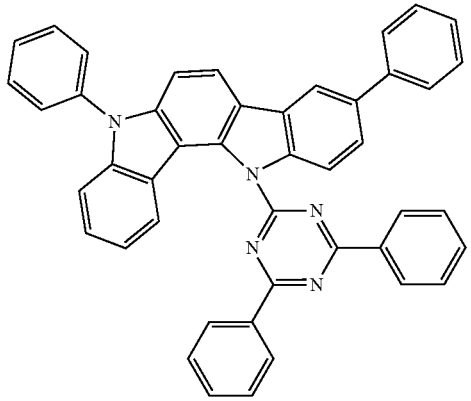
1-87
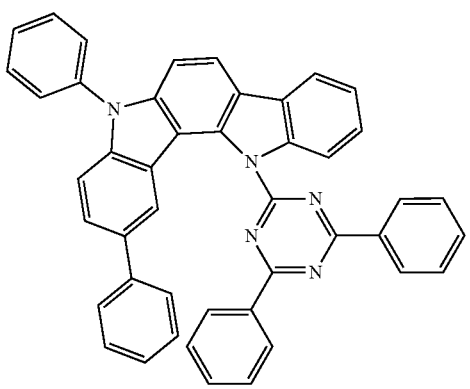
1-88
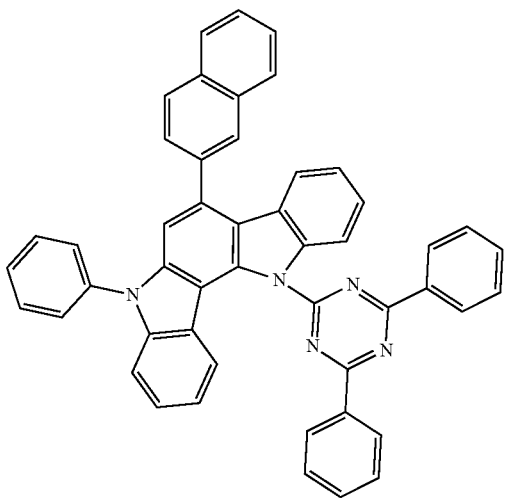

1-89
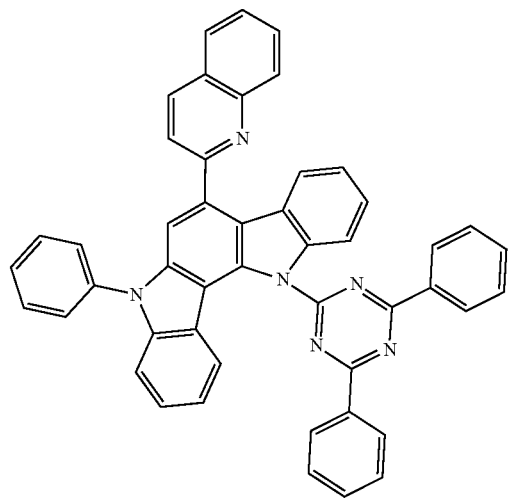
1-90
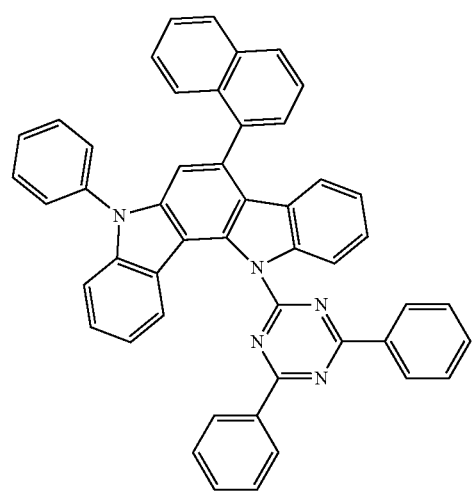
1-91
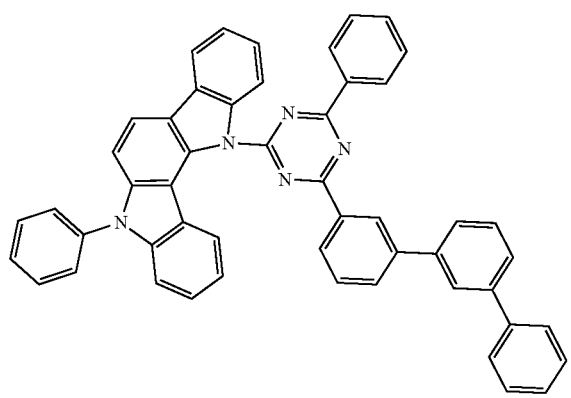
1-92
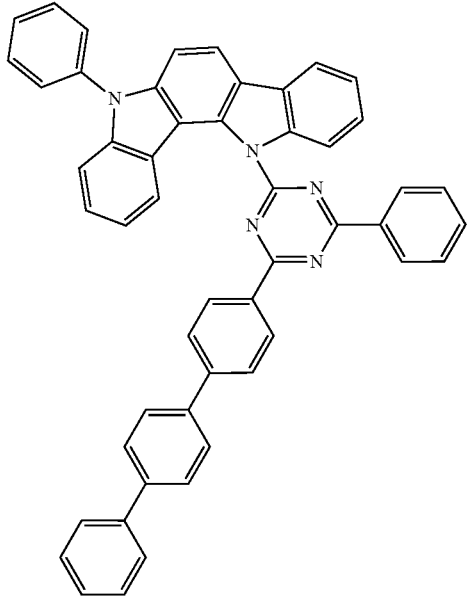
1-93
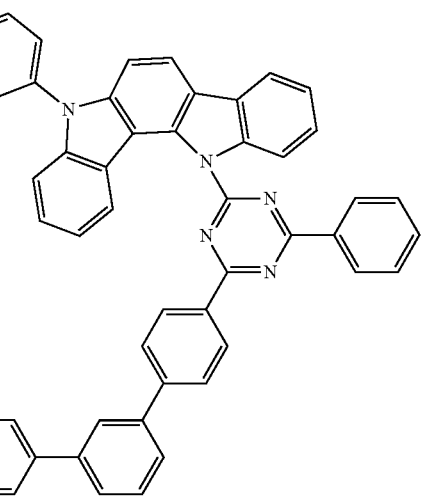

1-94
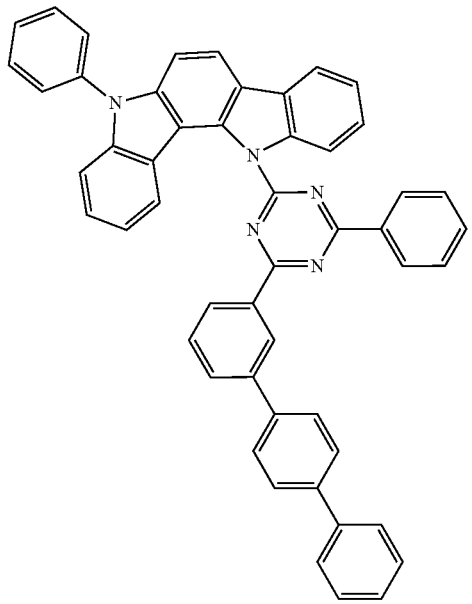
1-95
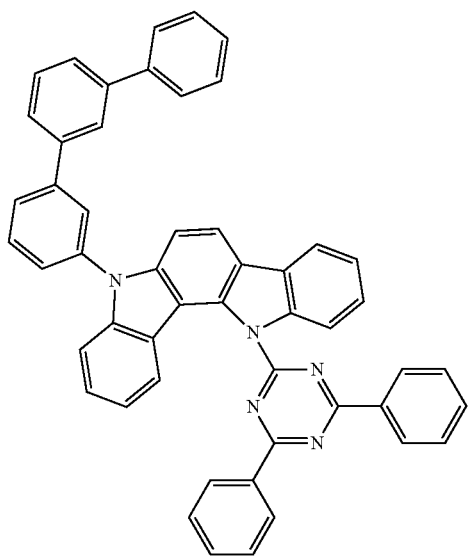
1-96
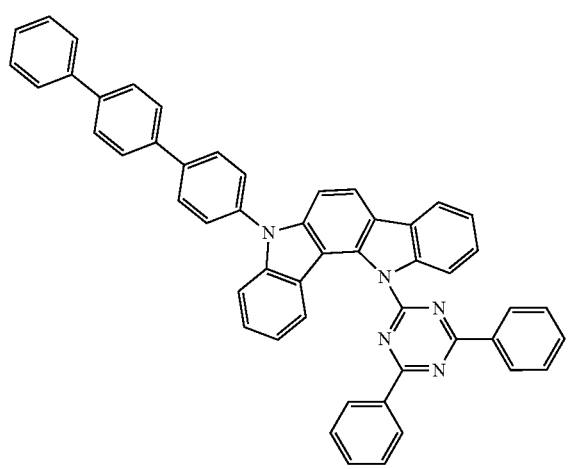
1-97
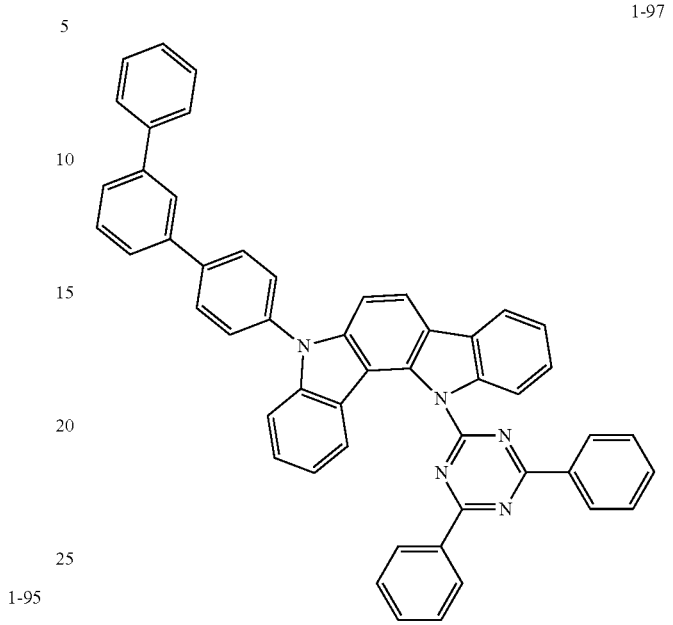
1-98

1-99
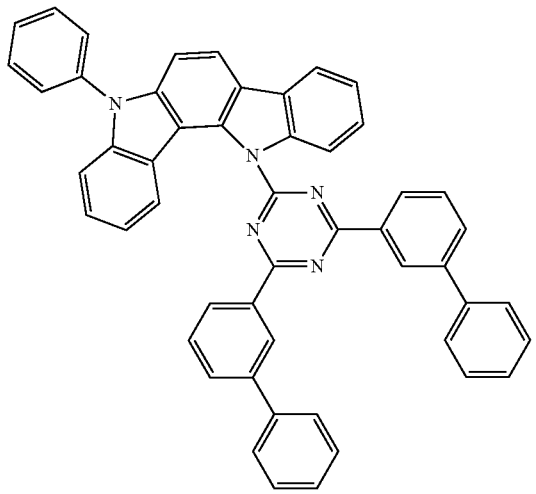
1-100
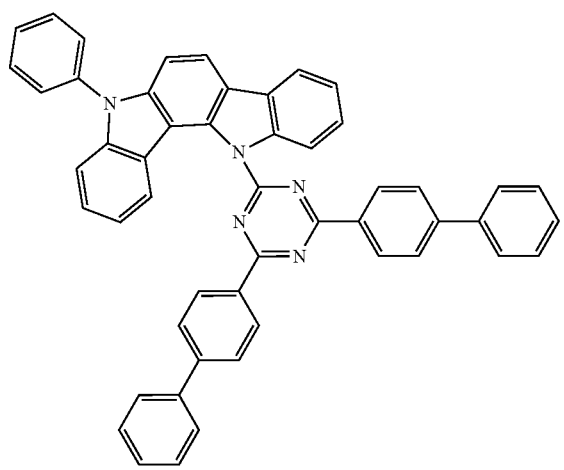
[C9]
1-101
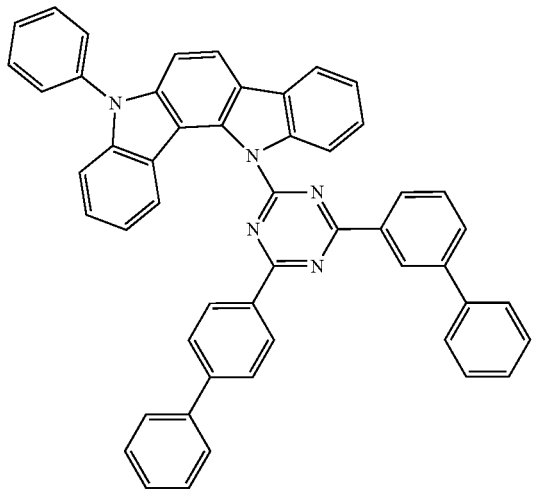
1-102
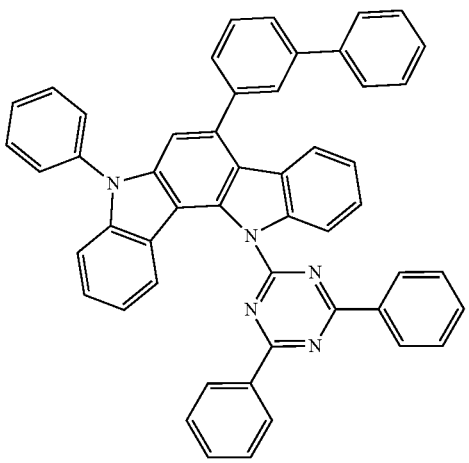
1-103
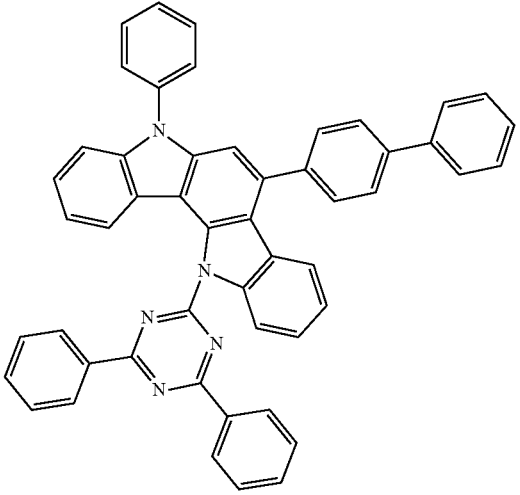
1-104
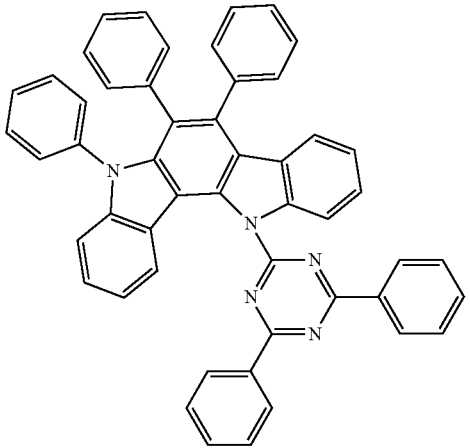

1-105
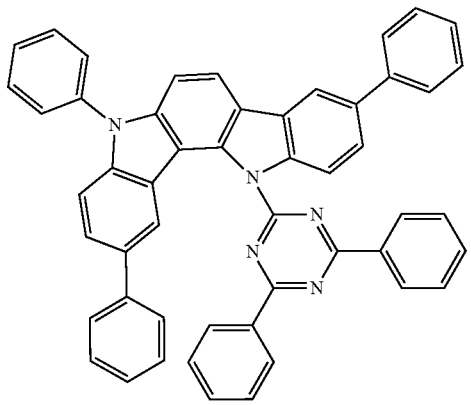
1-106
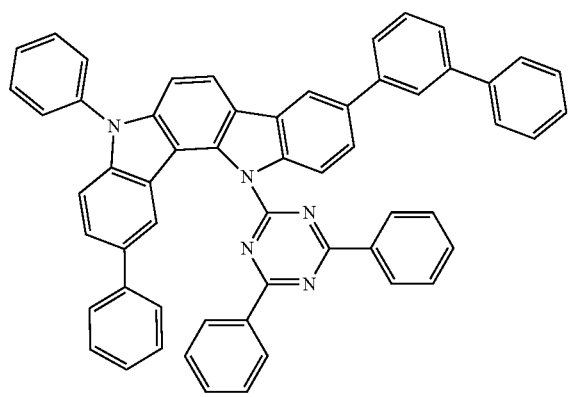
1-107
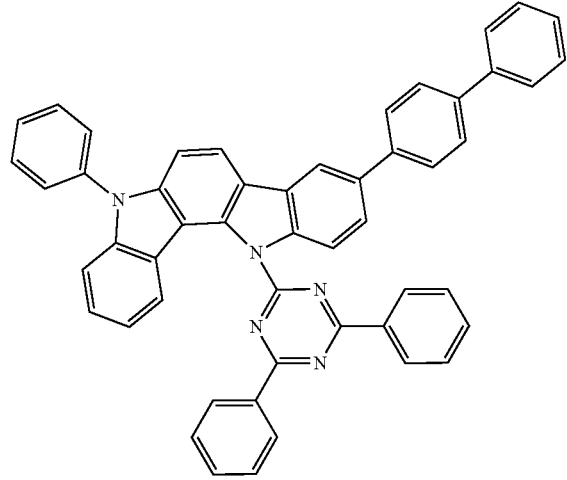
1-108
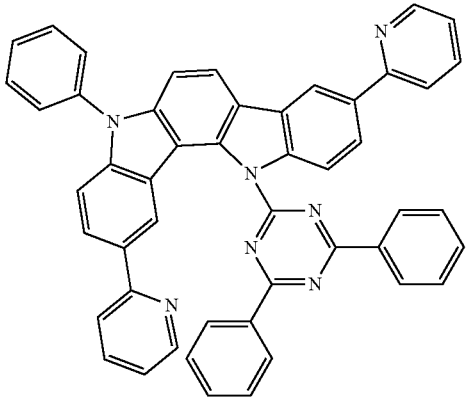
1-109
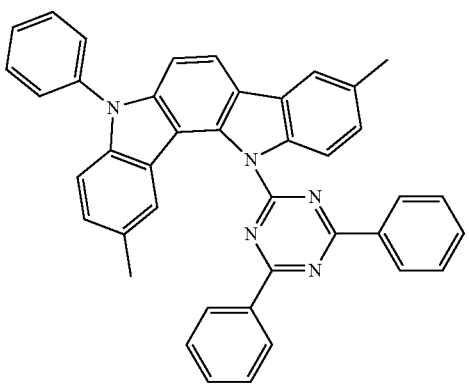
1-110
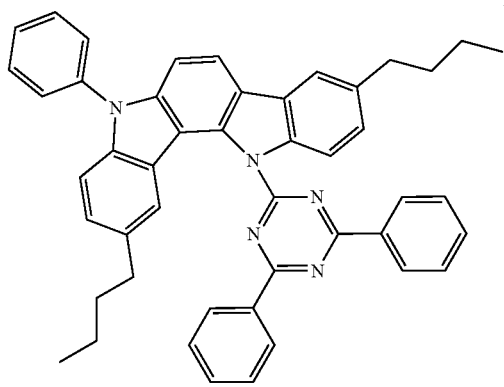
1-111
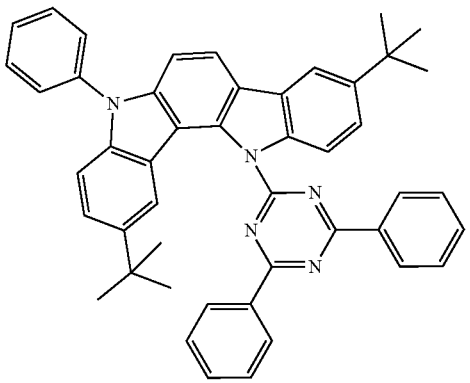

-continued
1-112
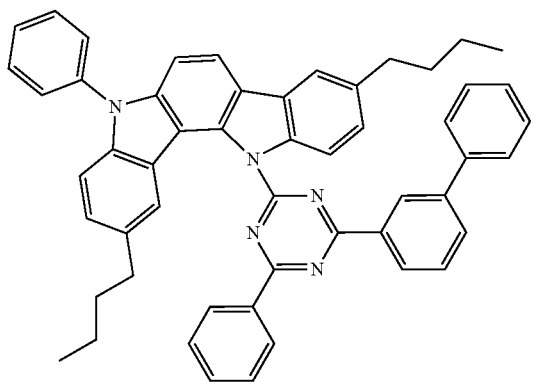
1-113
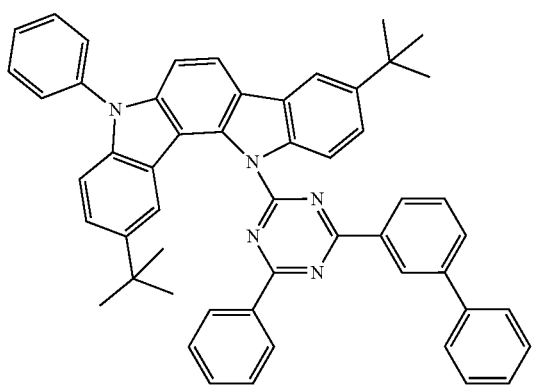
1-114
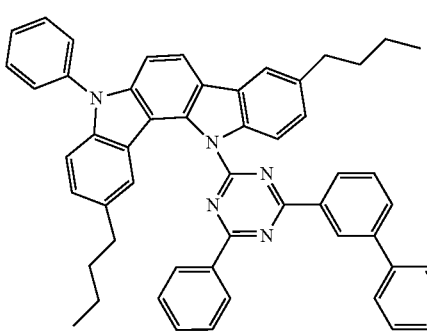
1-115
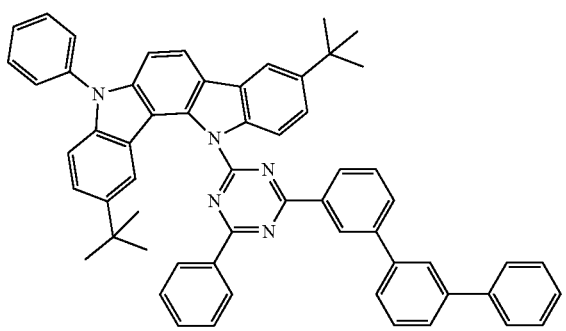
-continued
1-116
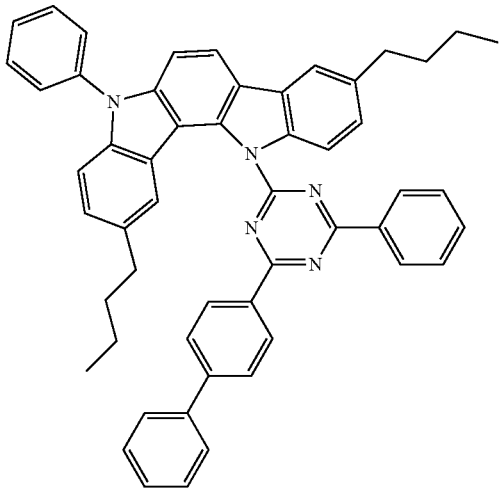
1-117
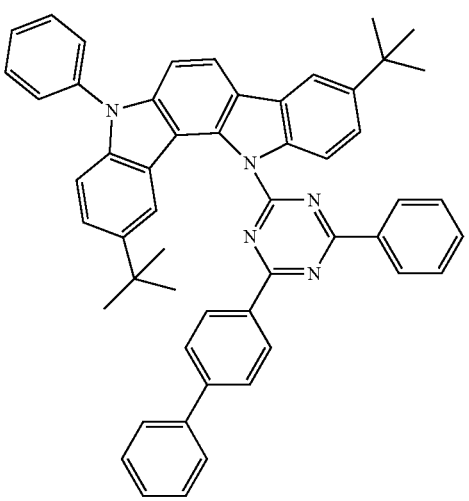
1-118
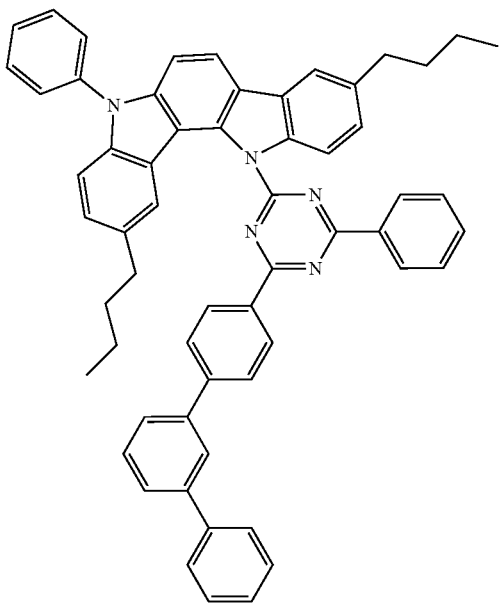

[C10]
1-119
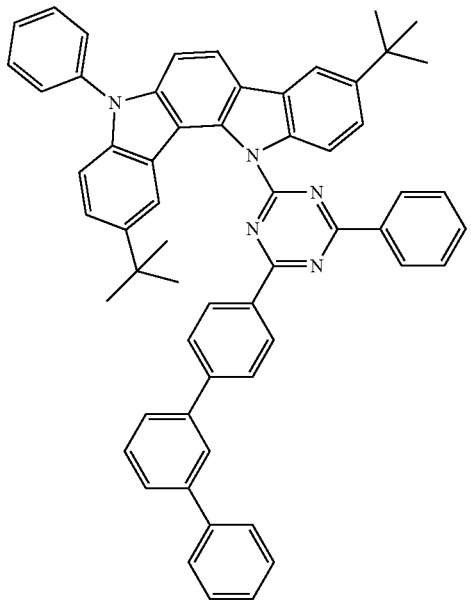
1-120
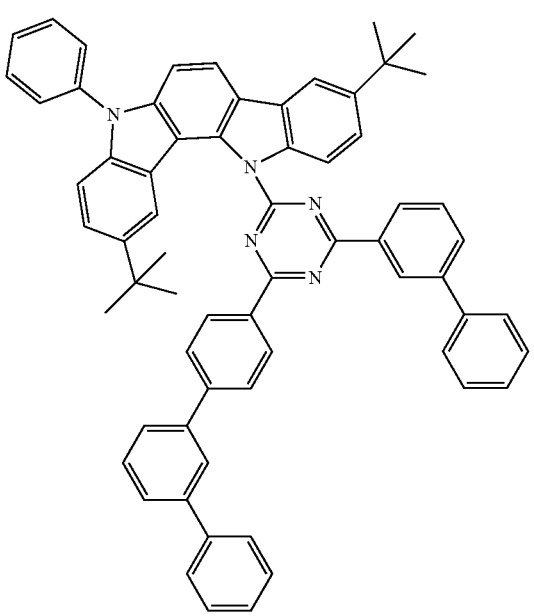
1-121
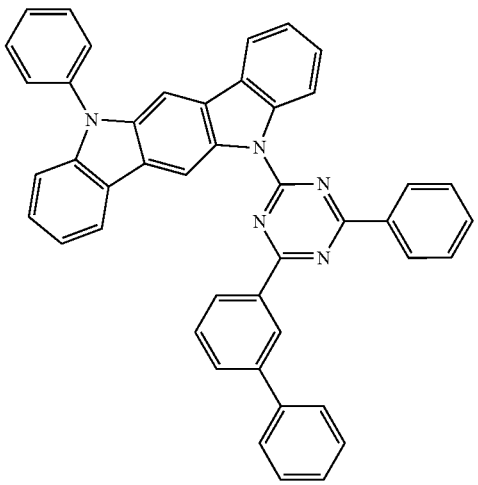
1-122
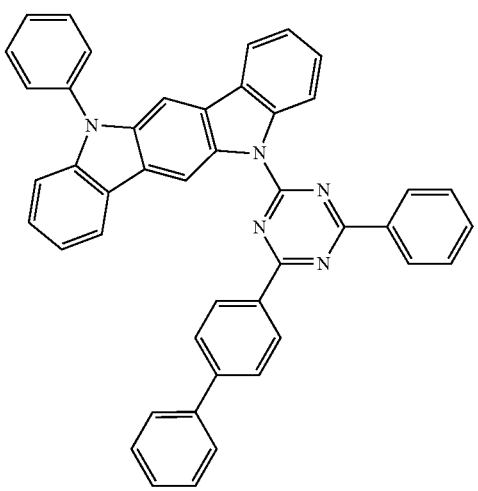
1-123
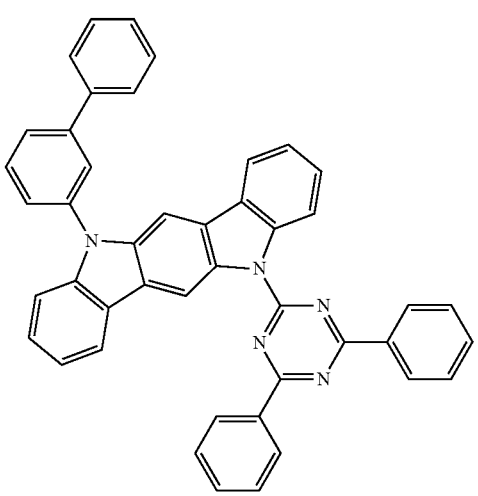

1-124
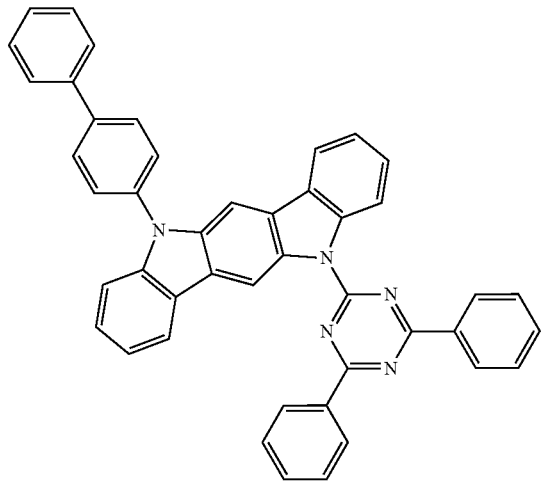
1-121
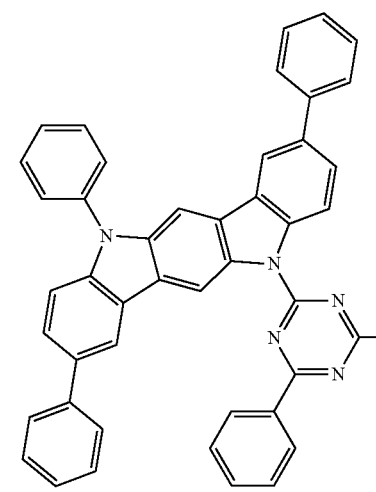
1-122
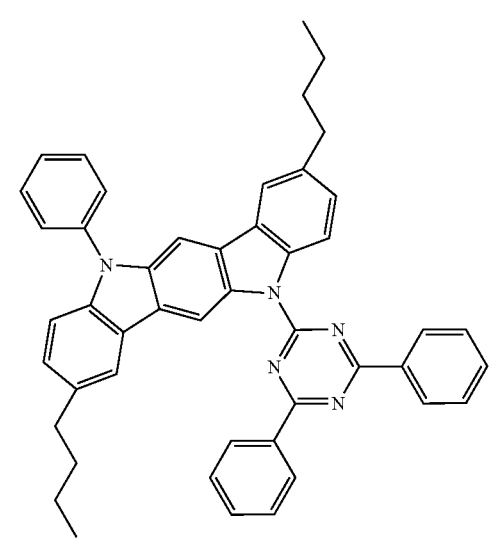
1-123
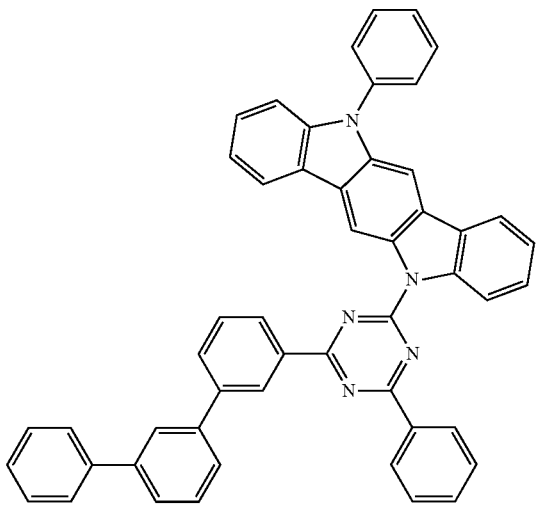
1-124
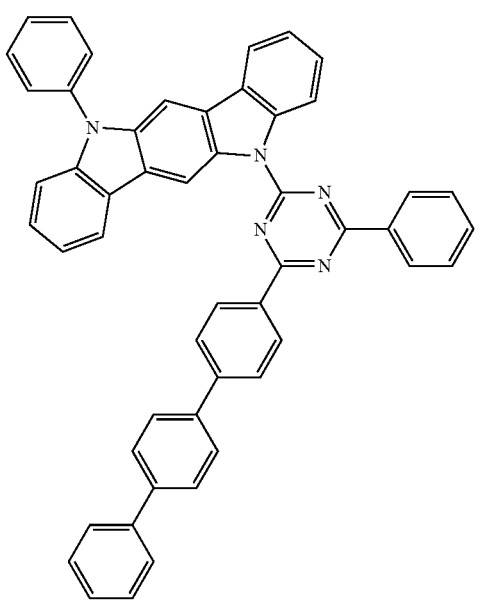

1-125
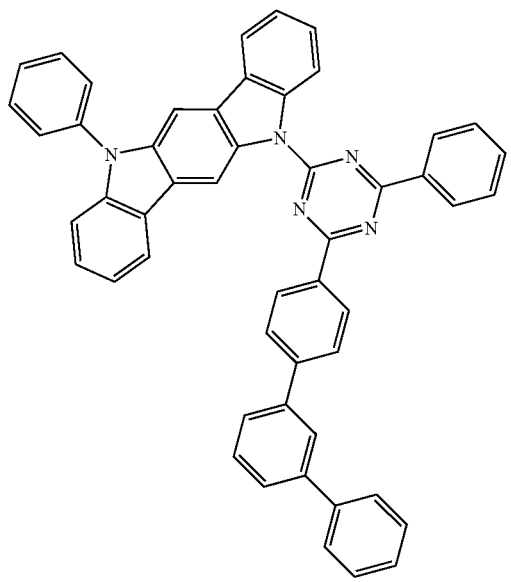
1-126
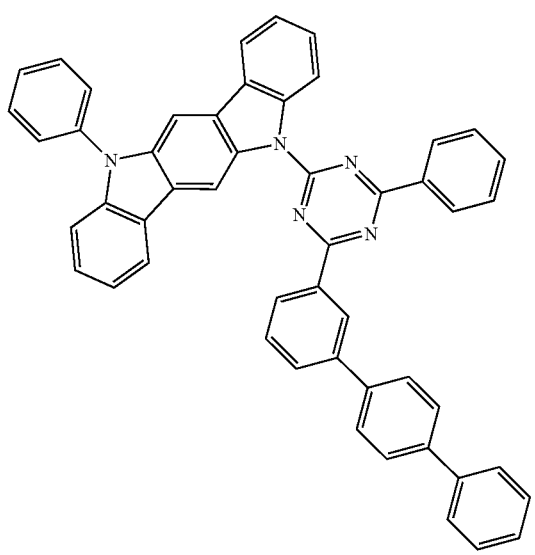
1-127
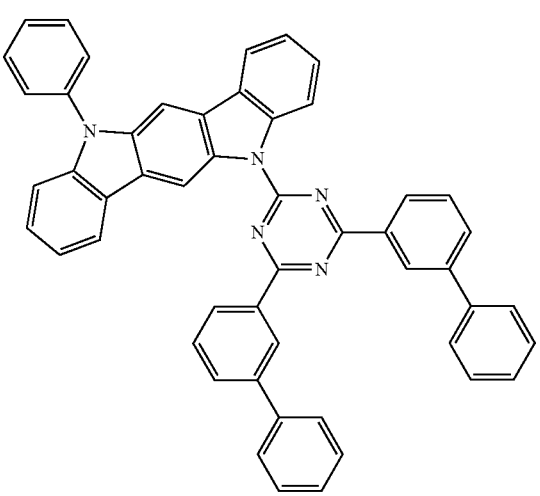
1-128
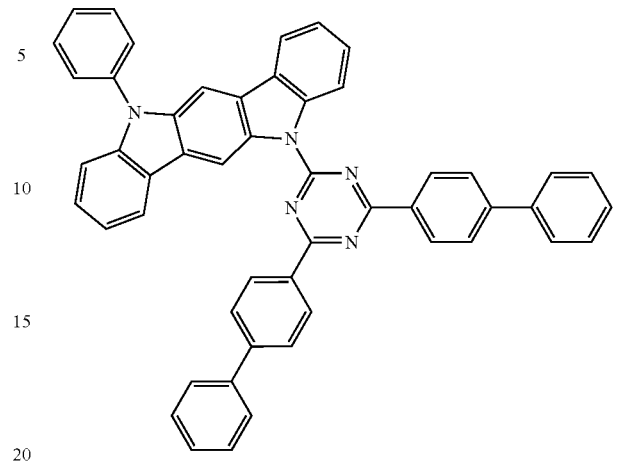
1-129
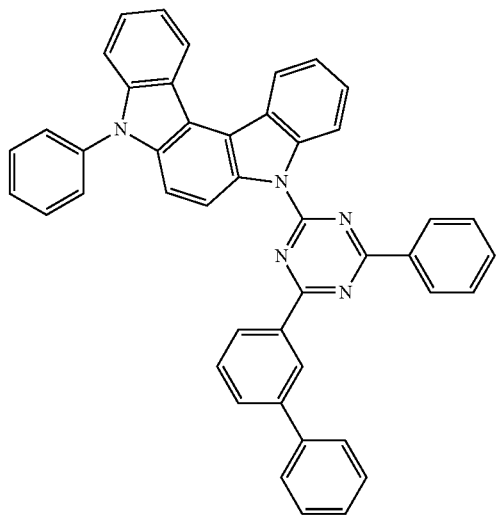
1-130
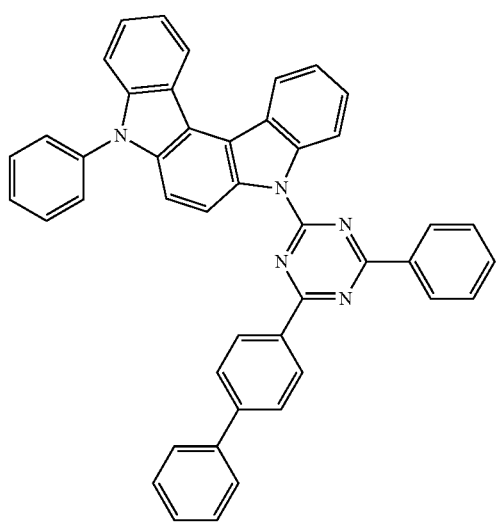

1-131
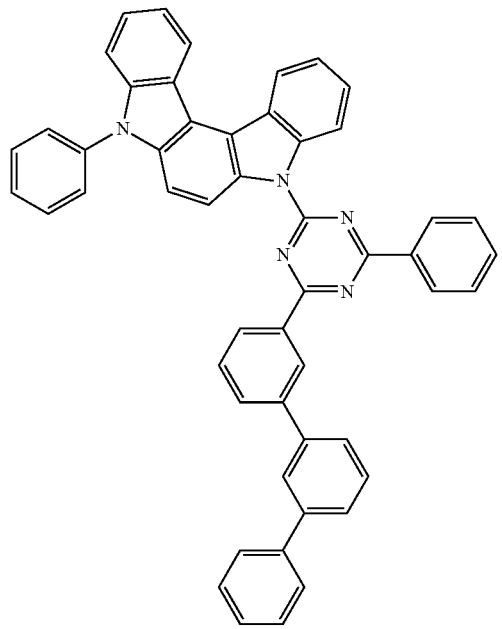
1-133
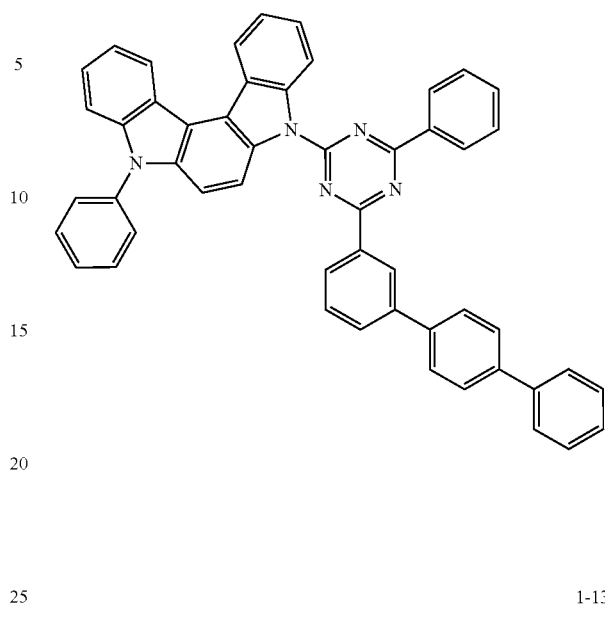
1-134
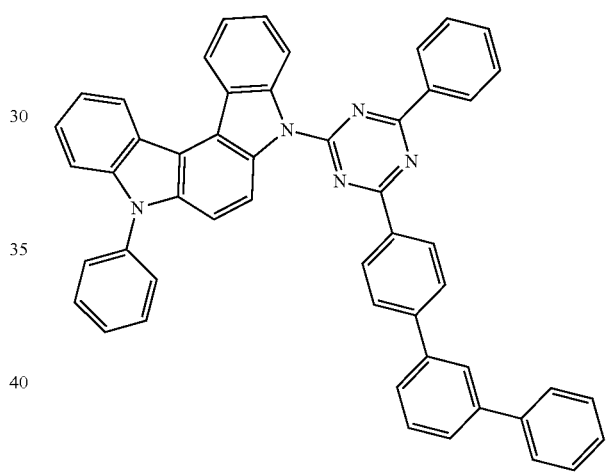
1-132
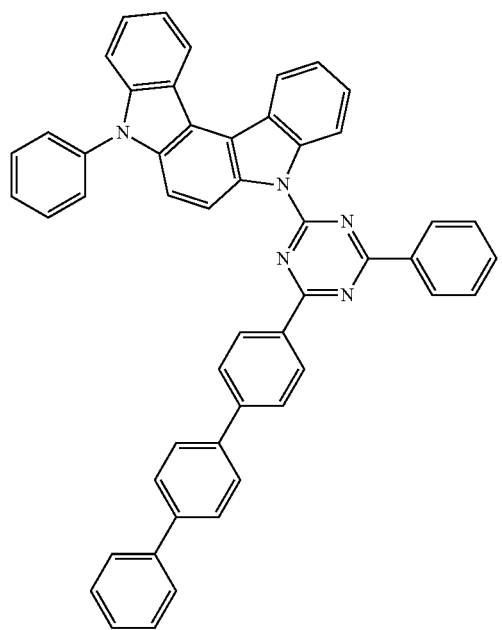
1-135
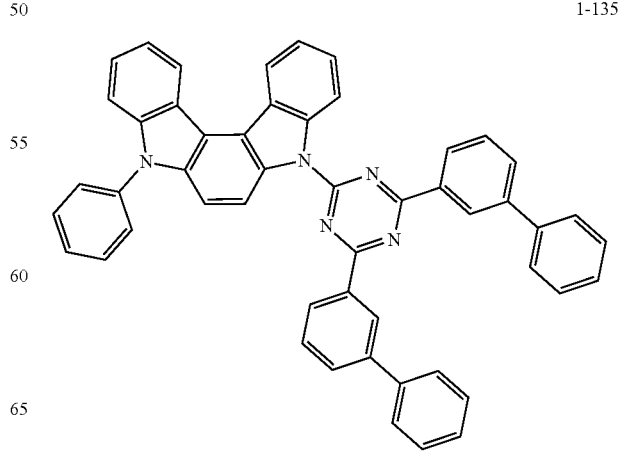

[C11]

1-142
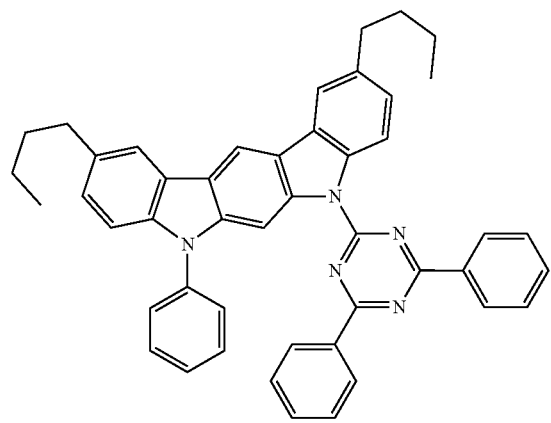
1-143
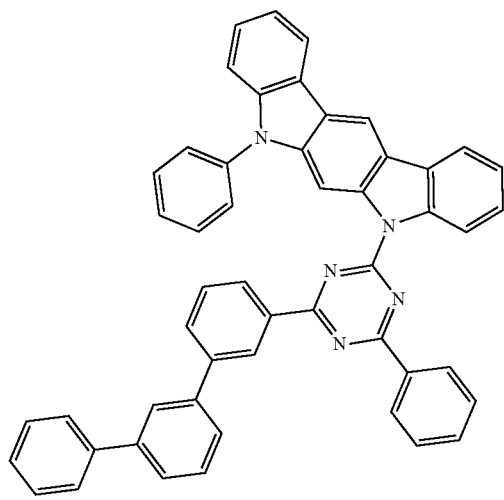
1-144
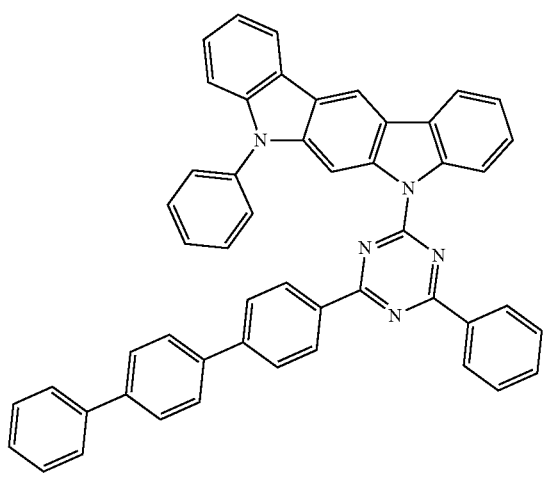
1-145
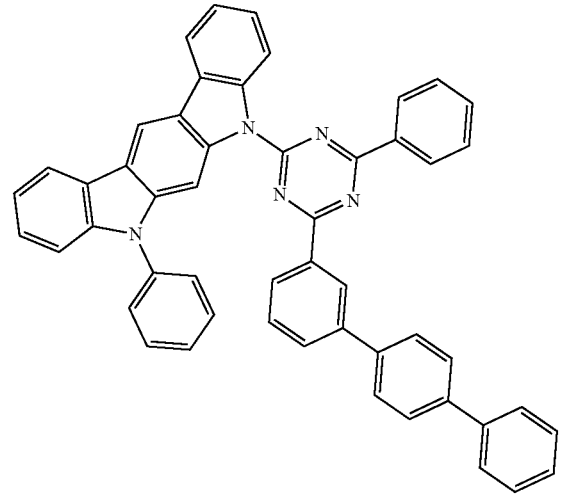
1-146
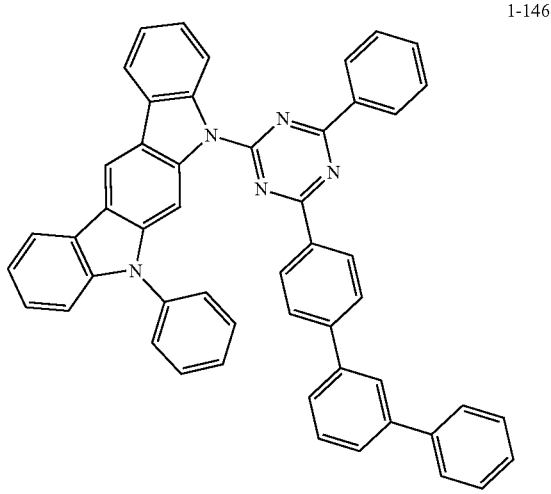
1-147
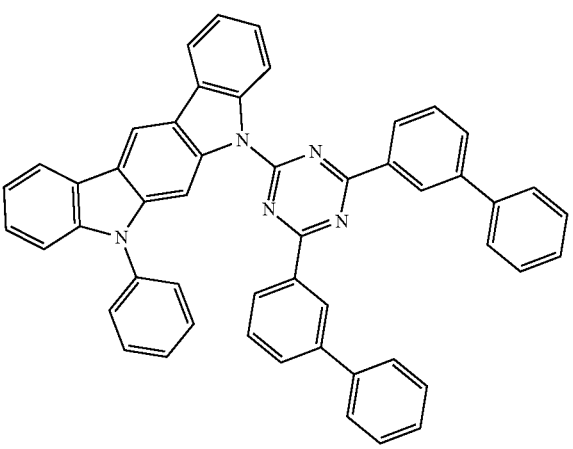

1-148
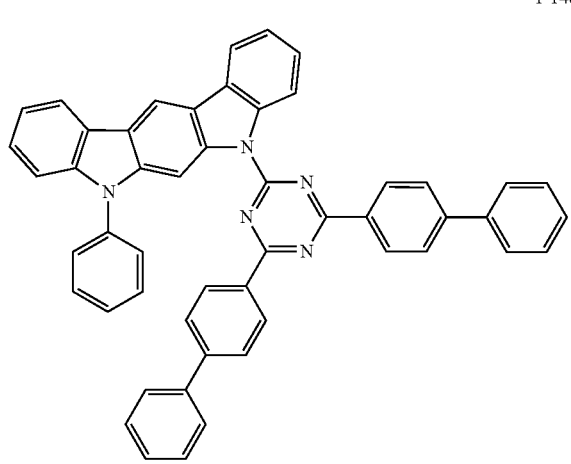
1-150
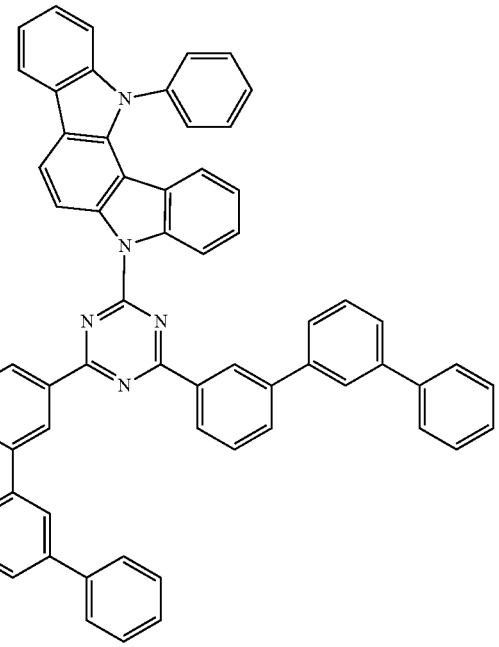
1-149
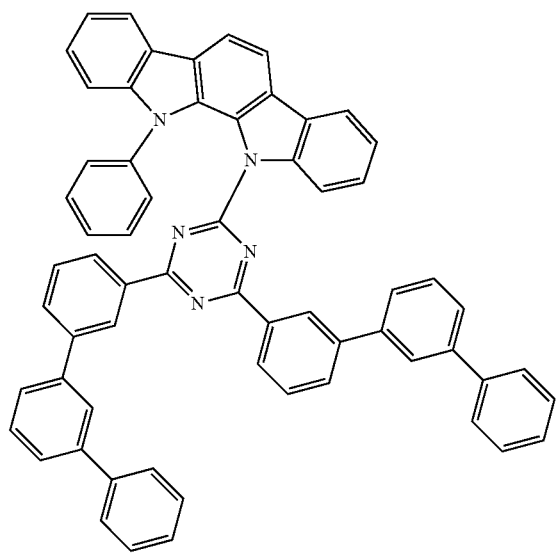
1-151

1-152
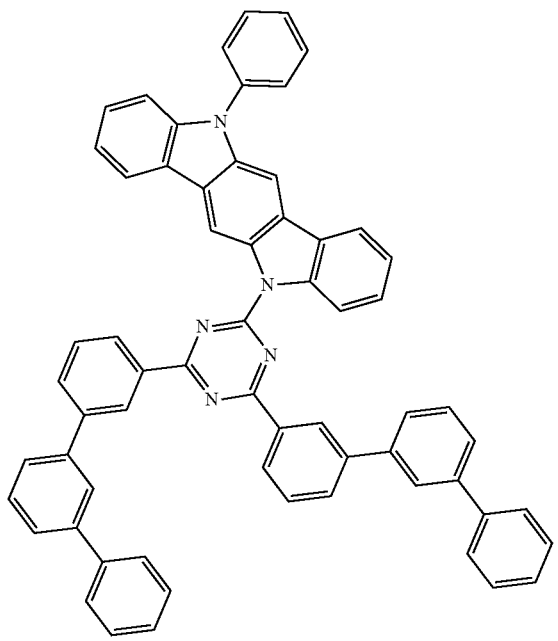
1-153
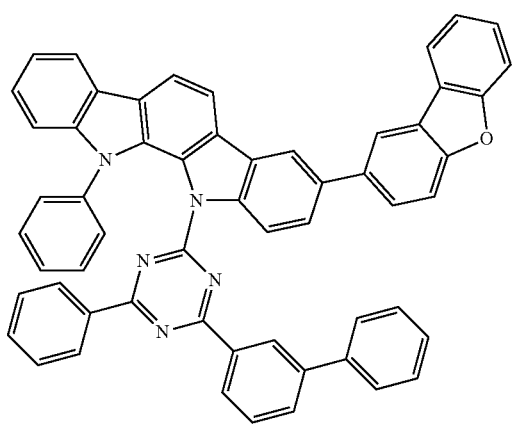
1-154
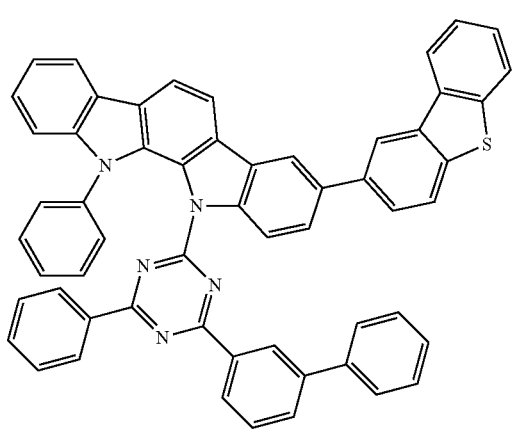
1-155
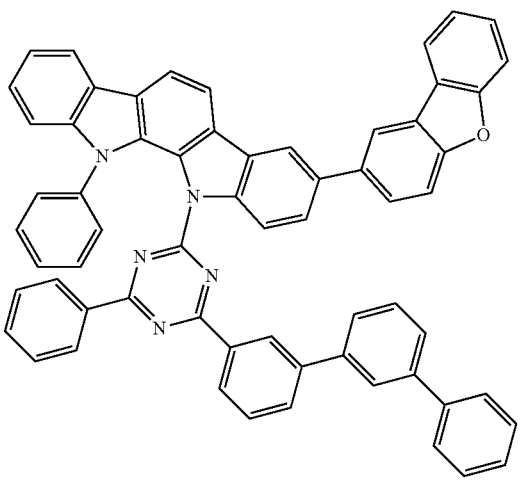
1-156
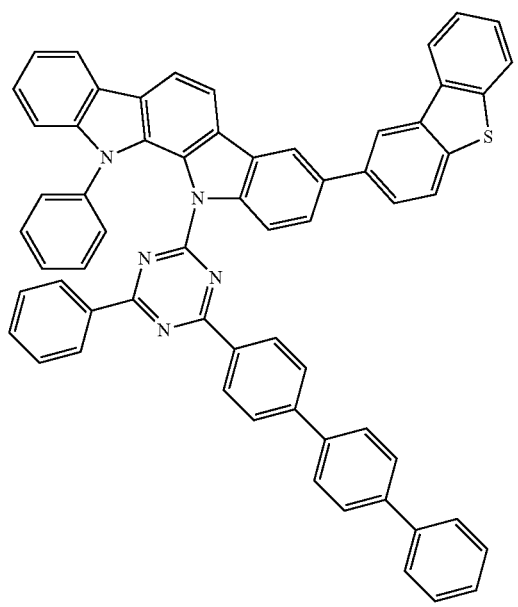
[C12]
1-157
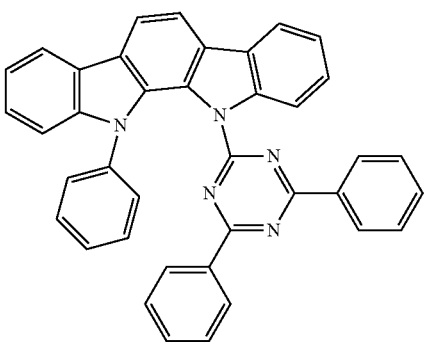

1-158

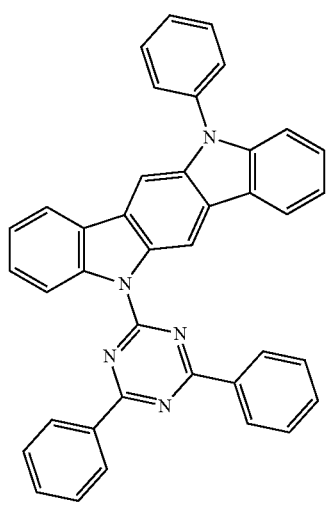

1-159

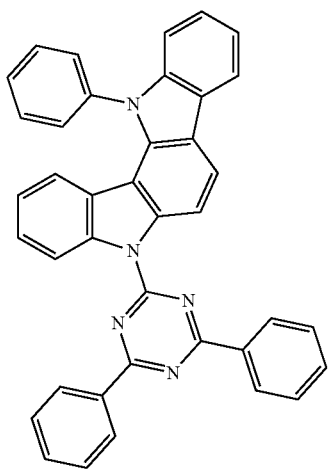

1-160

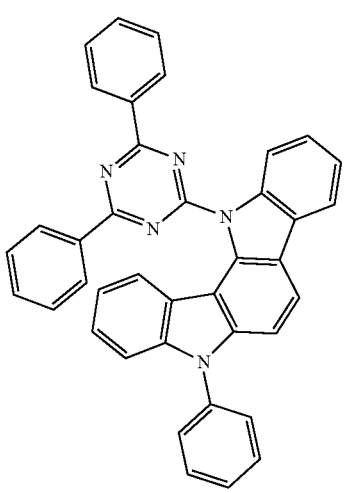

1-161

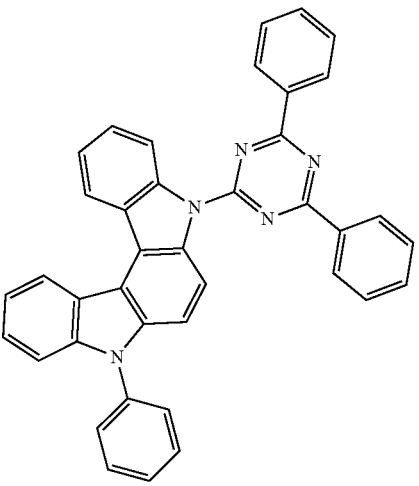

The compounds with general formulas (2), (3), and (4) that constitute the second host will now be described. The notations common to general formulas (2) to (4) have the same definitions thereamong.

$Ar^2$ and $Ar^3$ represent aromatic hydrocarbon groups having 6 to 14 carbons and groups in which 1 or 2 of these aromatic hydrocarbon groups are linked. Aromatic hydrocarbon groups having 6 to 12 carbons are preferred, while aromatic hydrocarbon groups having 6 to 10 carbons are more preferred.

$Ar^2$ and $Ar^3$ can be specifically exemplified by aromatic groups generated by the removal of one H from any aromatic compound, e.g., benzene, naphthalene, anthracene, phenanthrene, fluorene, and so forth, and by linked aromatic groups generated by the removal of one H from a compound in which the aromatic rings of two of these aromatic compounds are linked to each other. Aromatic groups generated from benzene, naphthalene, anthracene, and phenanthrene are preferred, as are linked aromatic groups in which two of these aromatic groups are linked to each other. Aromatic groups generated from benzene, naphthalene, and phenanthrene are more preferred. $Ar^3$ is even more preferably a phenyl group. The linked aromatic group here is a group represented by formulas such as —$Ar^4$—$Ar^6$, —$Ar^4$—$Ar^5$—$Ar^6$, or —$Ar^4$(—$Ar^5$)—$Ar^6$, wherein $Ar^4$, $Ar^5$, and $Ar^6$ are each independently an aromatic hydrocarbon group having 6 to 14 carbons. $Ar^4$ is a divalent or trivalent group; $Ar^5$ is a monovalent or divalent group; and $Ar^6$ is a monovalent group.

$L^1$ represents a direct bond or a divalent phenylene group with any of formulas (2a), (2b), and (2c), and a divalent phenylene group represented by formula (2a) or (2b) is preferred. $L^2$ represents a divalent phenylene group represented by formula (2c).

When the aromatic group directly bonded to N in the carbazole ring is a phenylene group, this is taken to mean that it is $L^1$.

Specific examples of the compounds represented by general formulas (2) to (4) are given below, but there is no limitation to these exemplary compounds.

[C13]
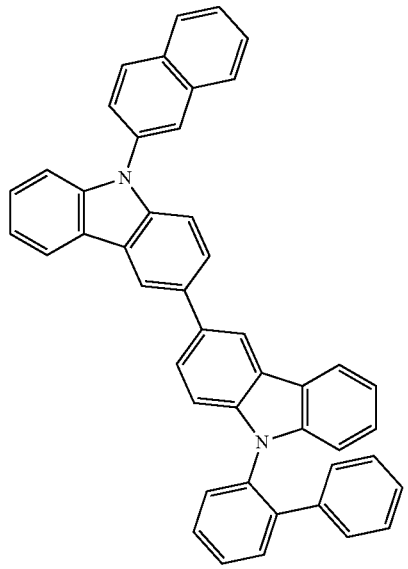
2-1
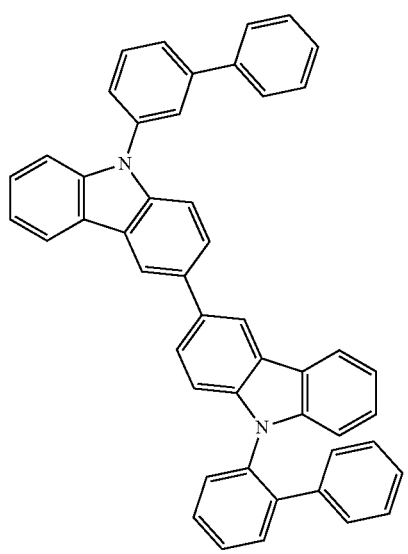
2-2
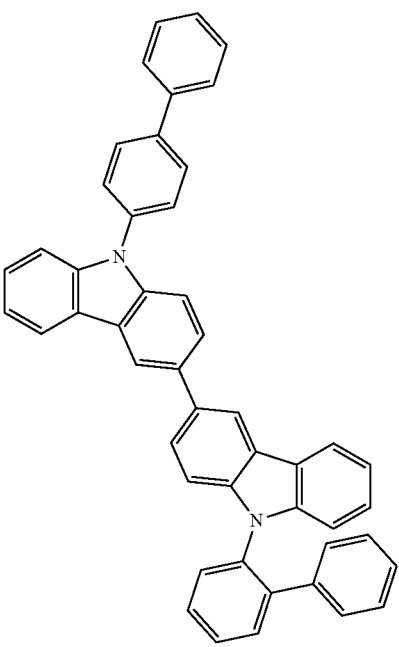
2-3
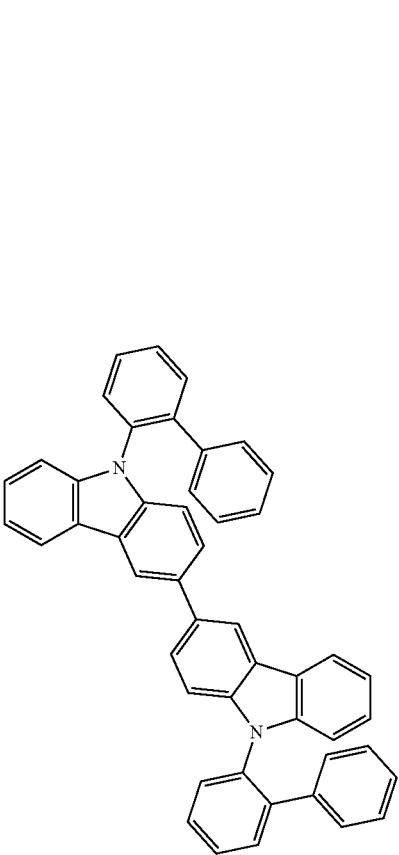
2-4

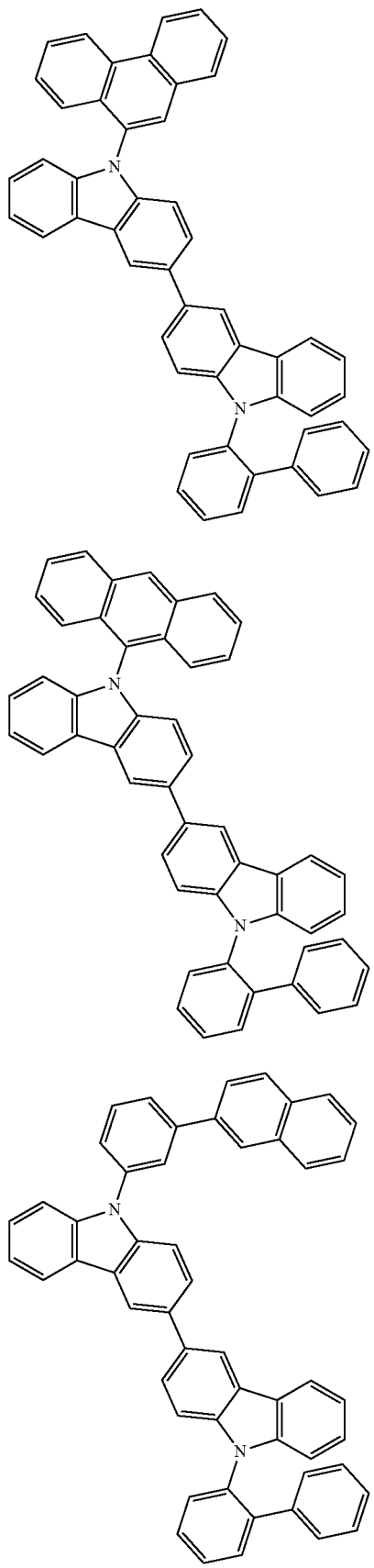

2-10
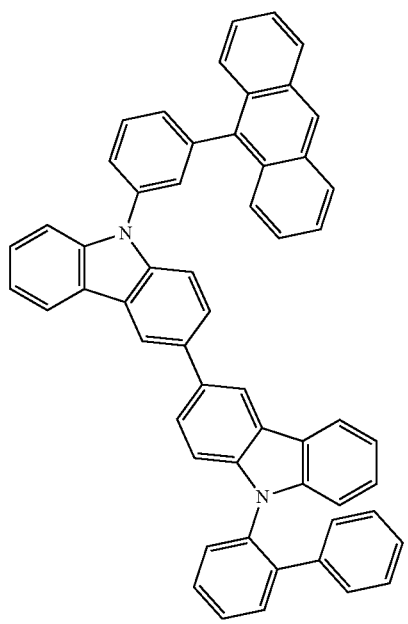
2-11
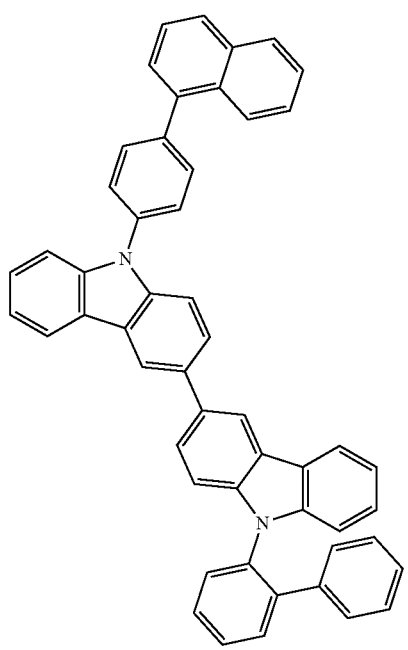
2-12
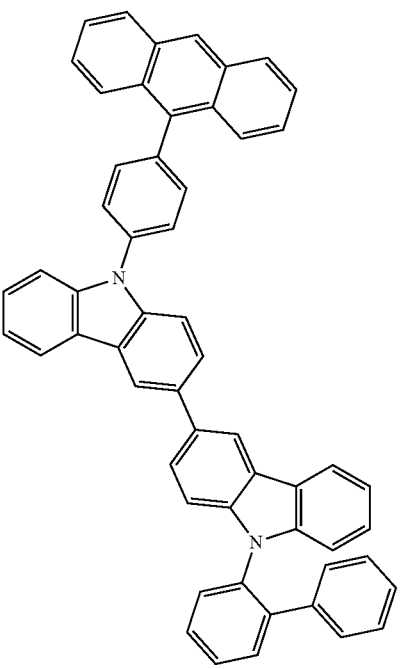
2-13
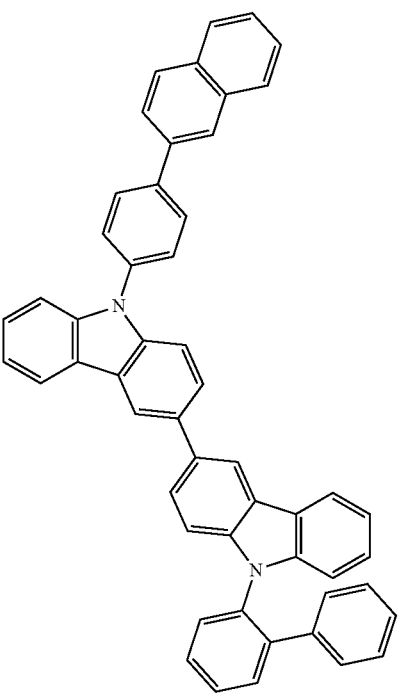

2-14
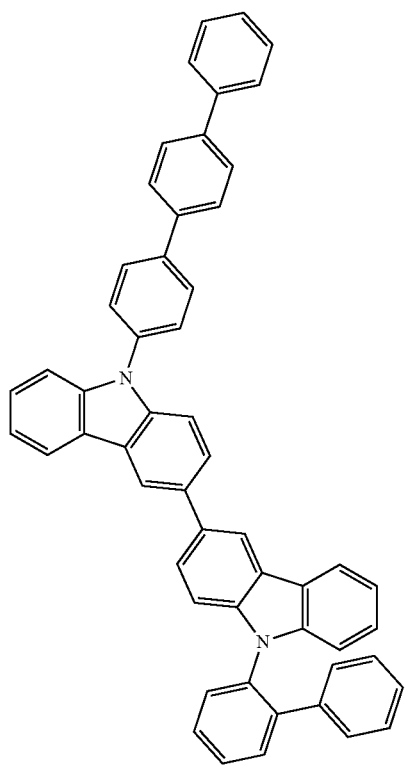
2-15
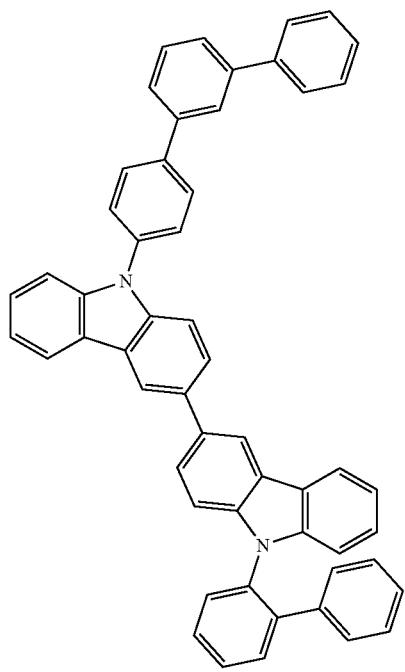
2-16
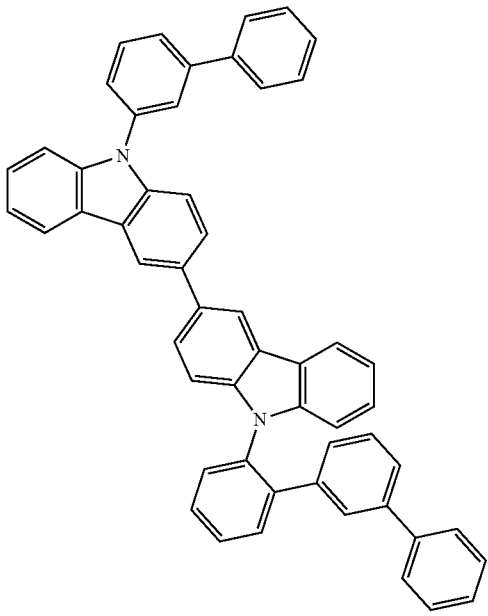
2-17
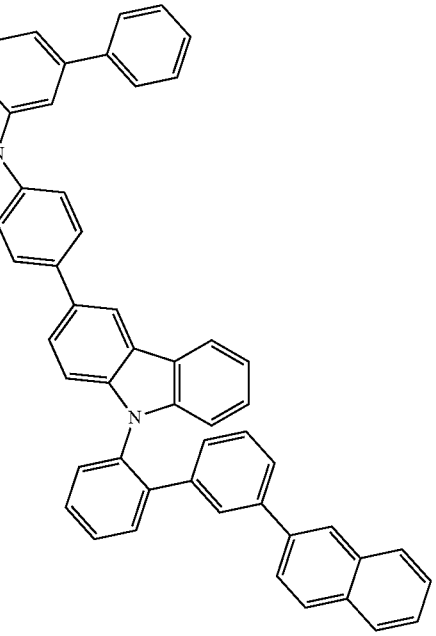

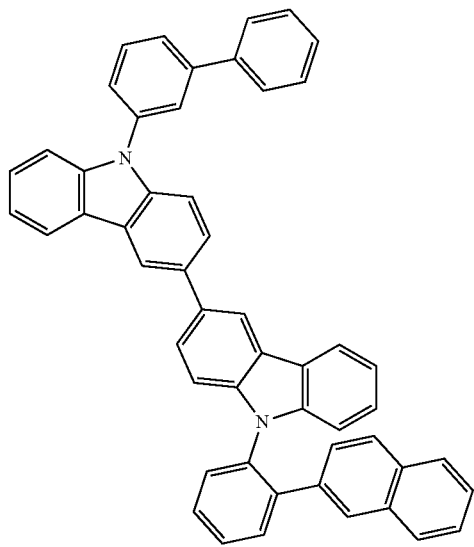 2-18
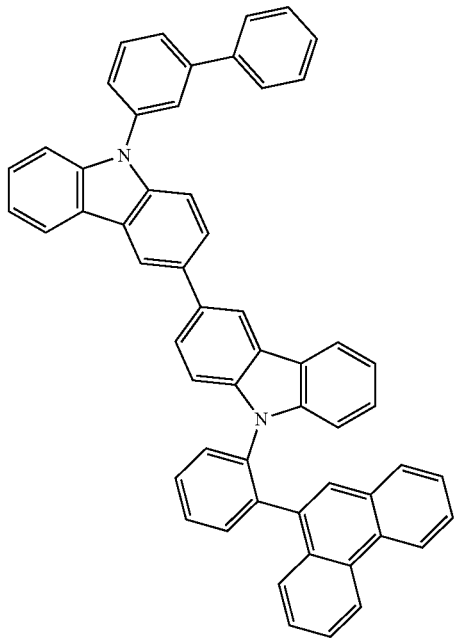 2-20
[C14]
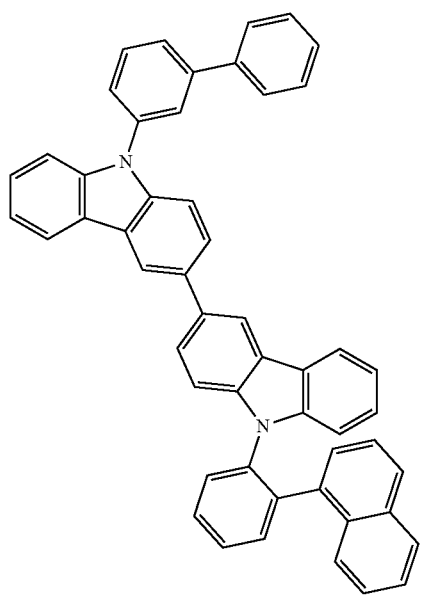 2-19
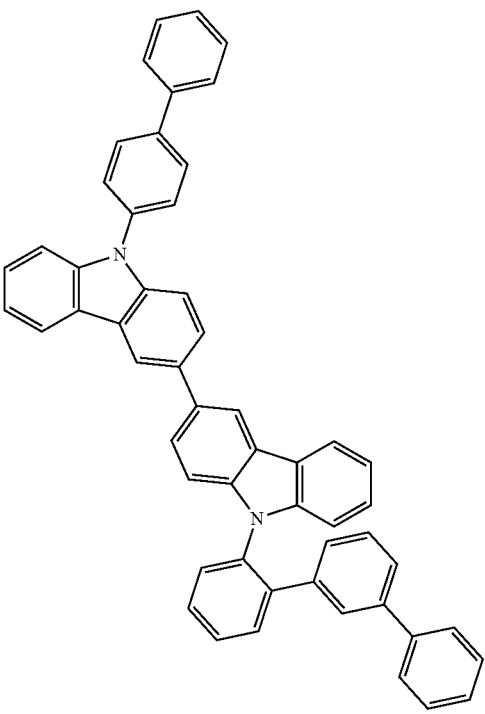 2-21

2-22
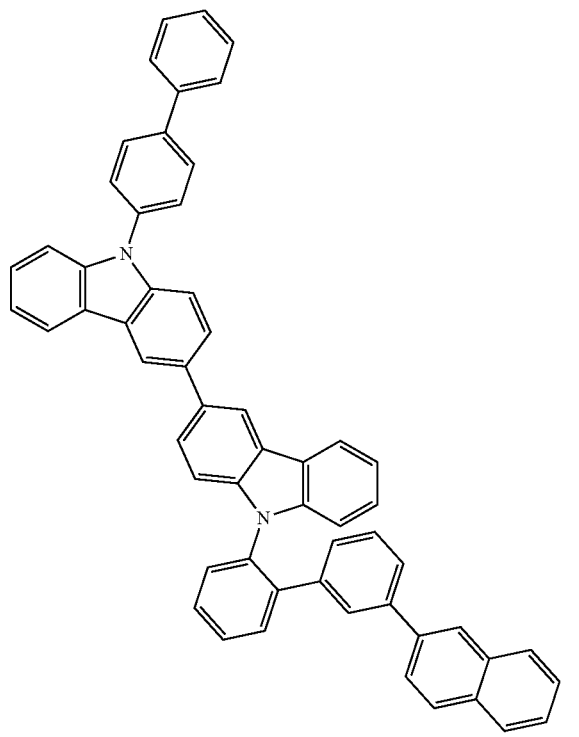
2-24
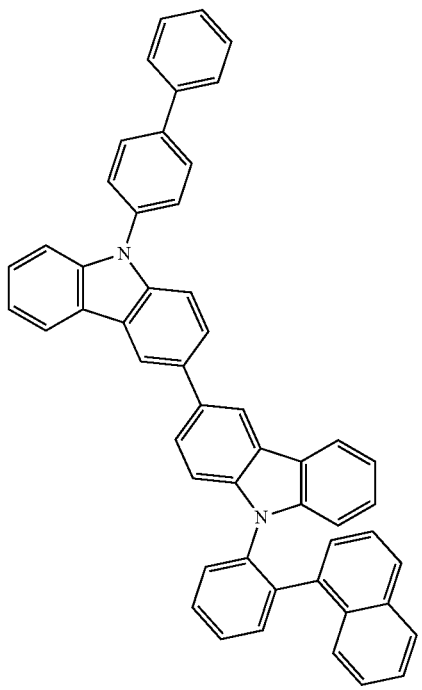
2-23
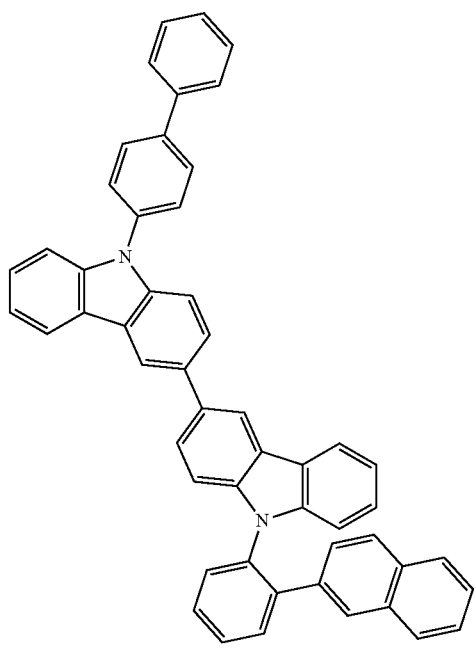
2-25
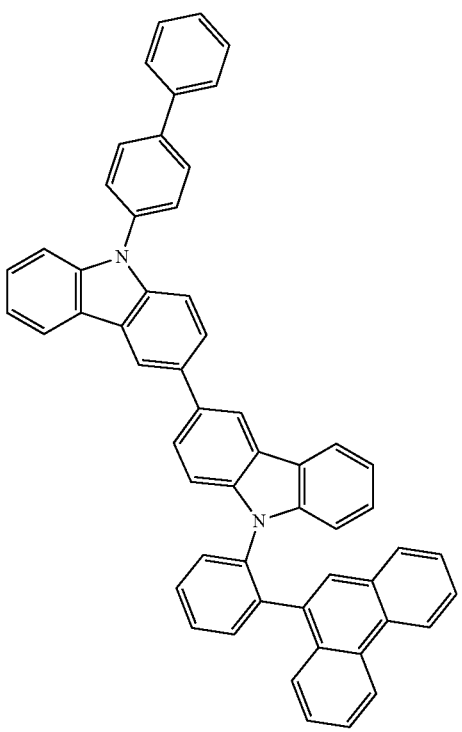

2-26
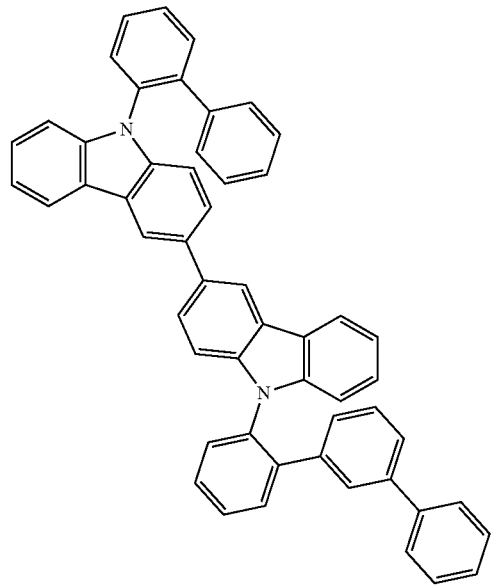
2-27
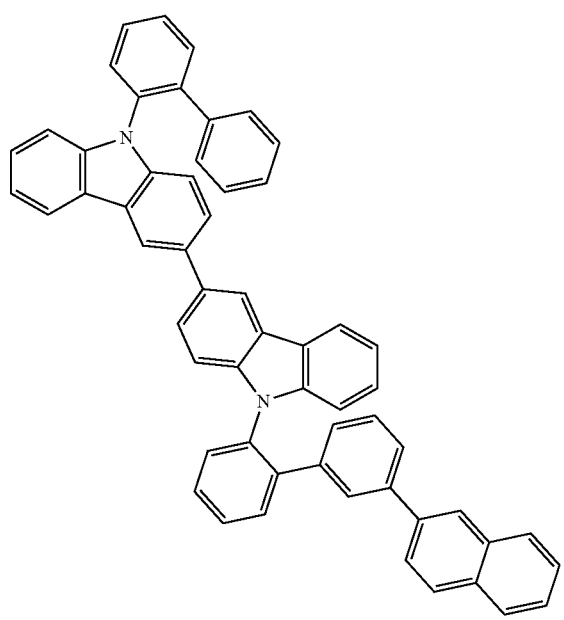
2-28
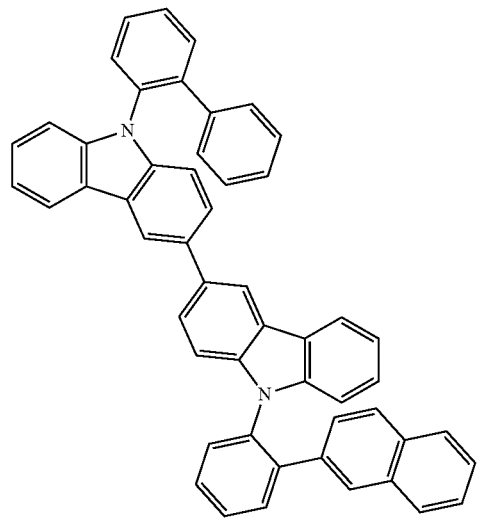
2-29
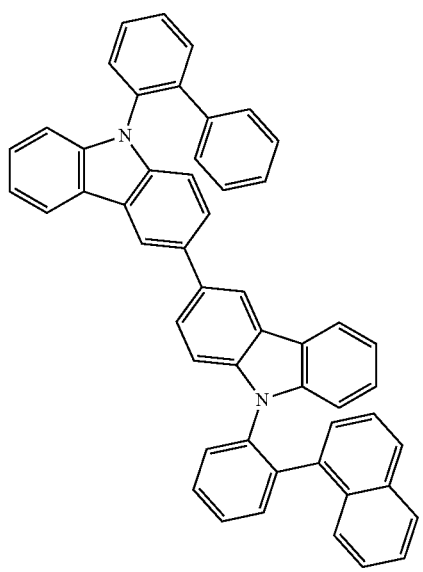

2-30
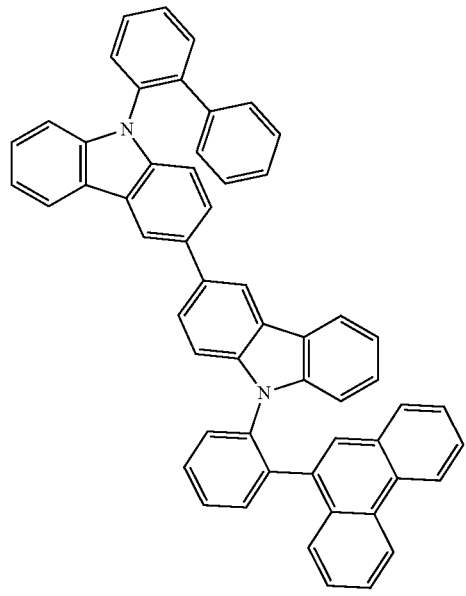
2-31
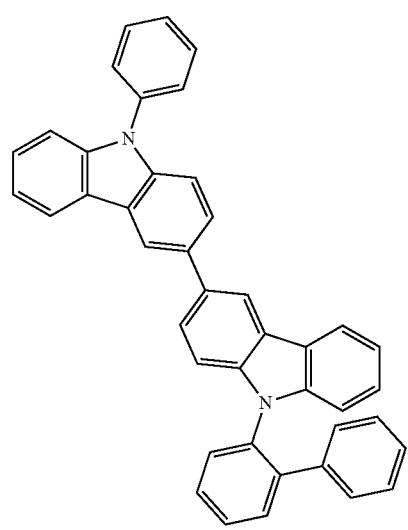
2-32
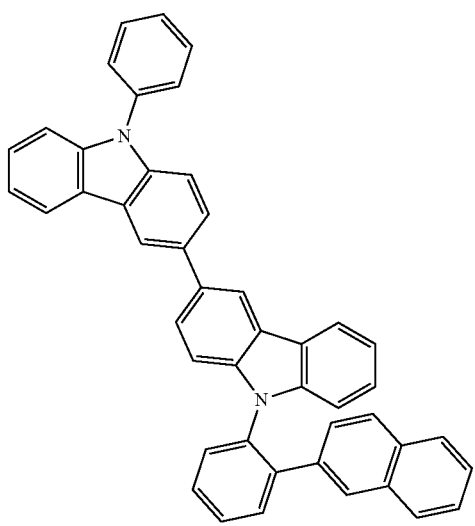
2-33
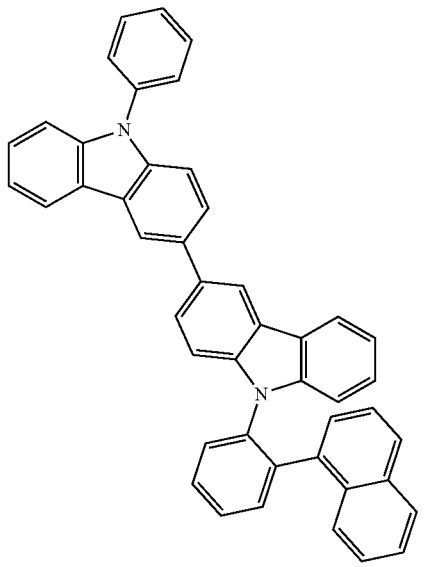
2-34
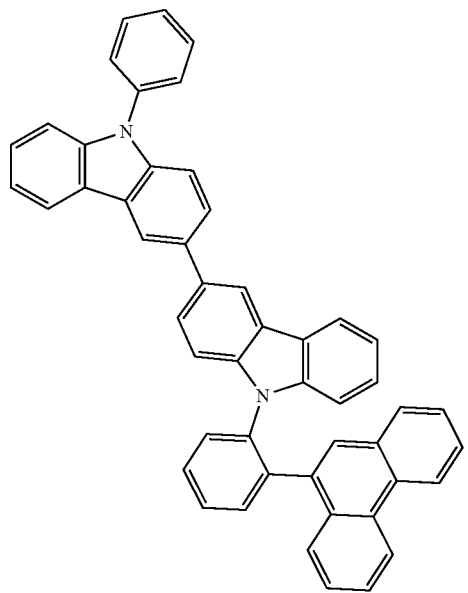

2-35
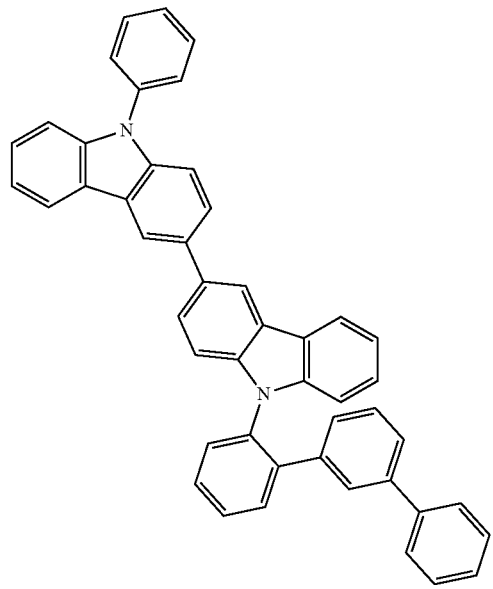
2-37
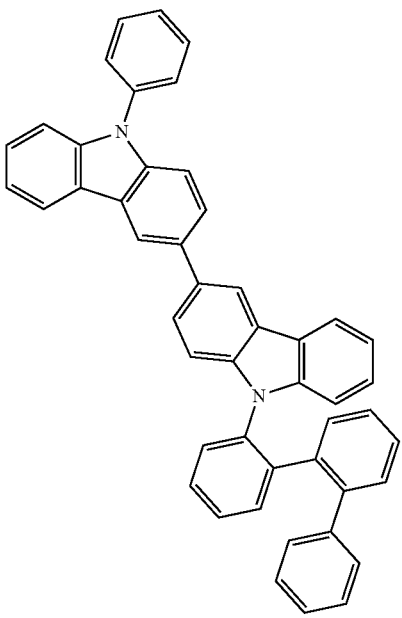
2-36
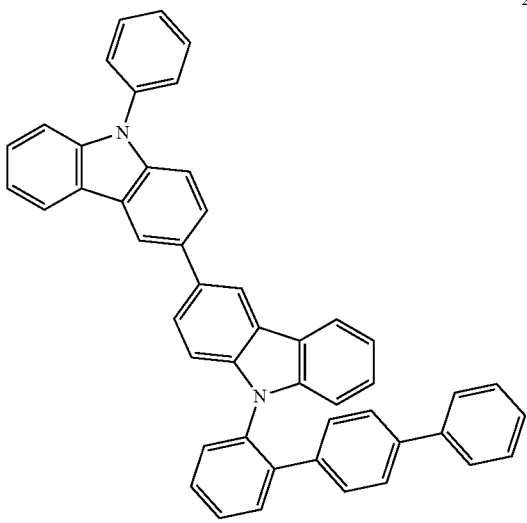
2-38
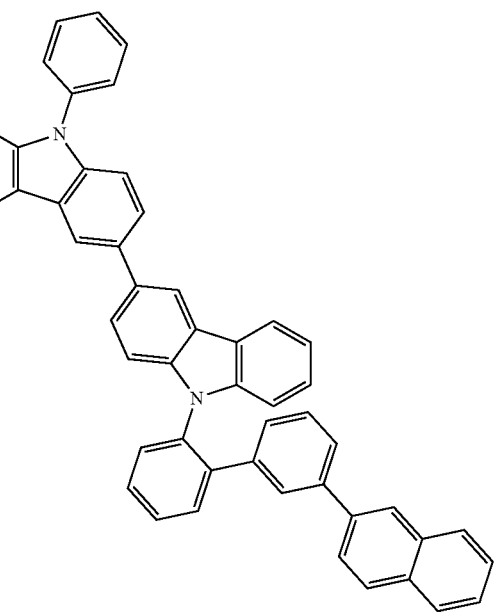

2-39
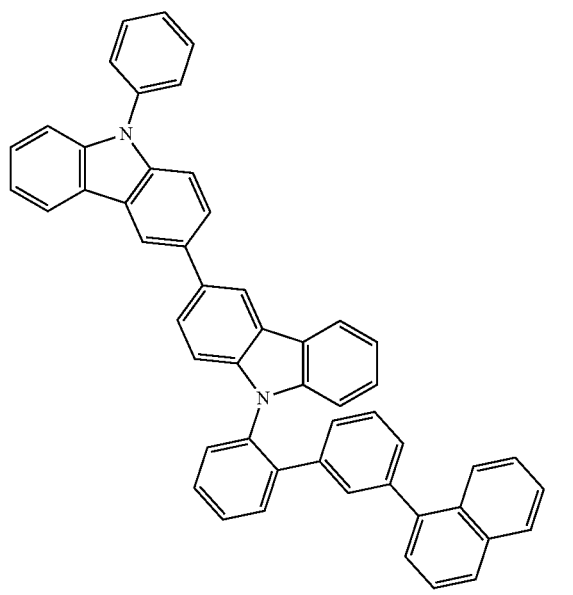
[C15]
2-40
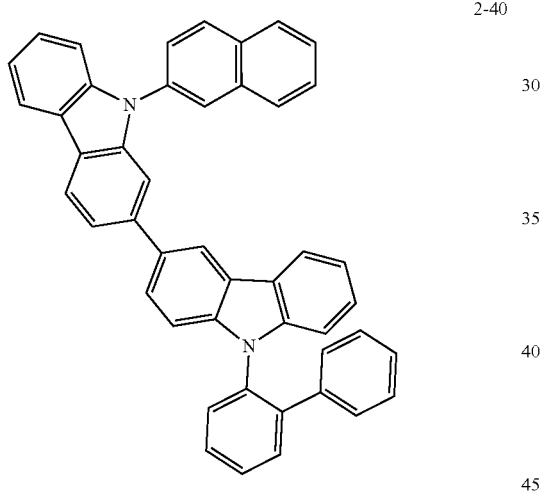
2-41
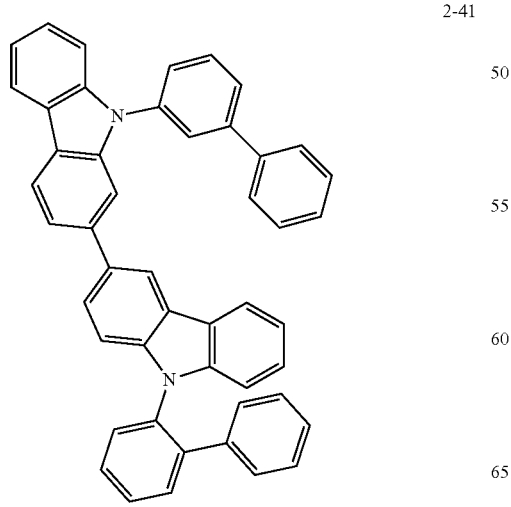
2-42
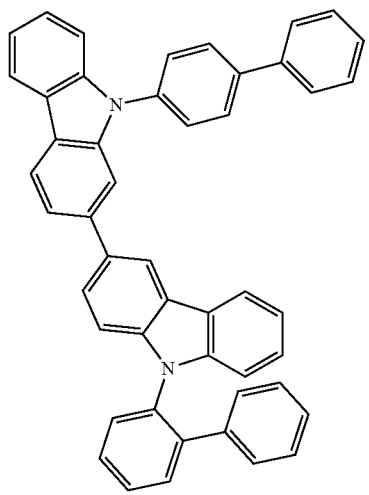
2-43
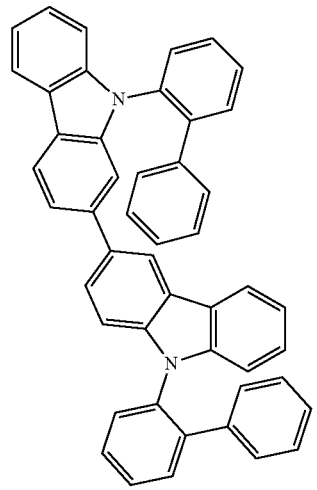
2-44
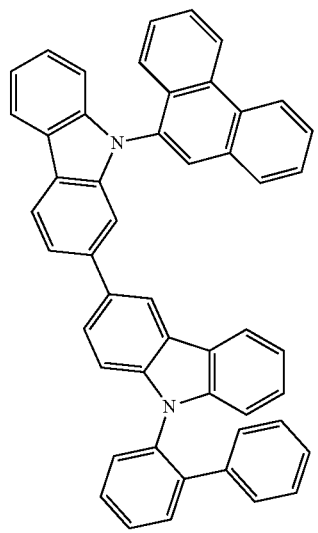

2-45
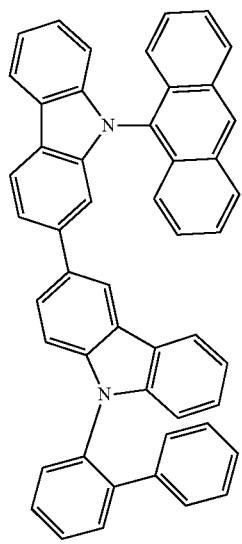
2-48
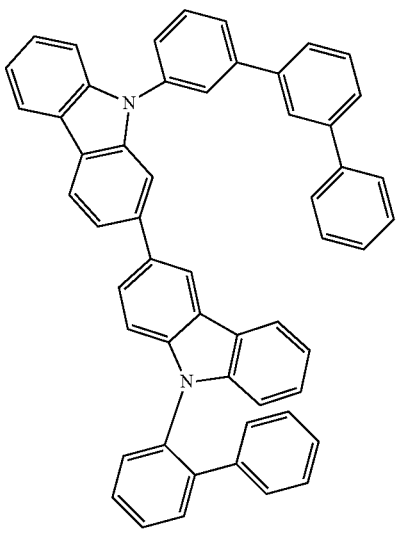
2-46
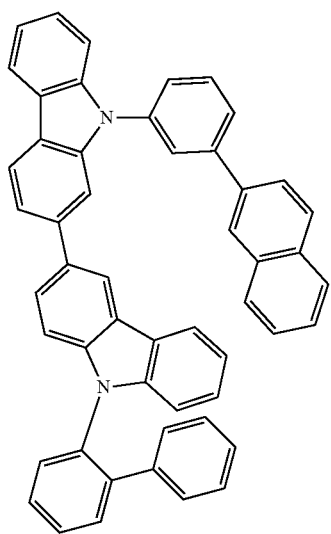
2-49
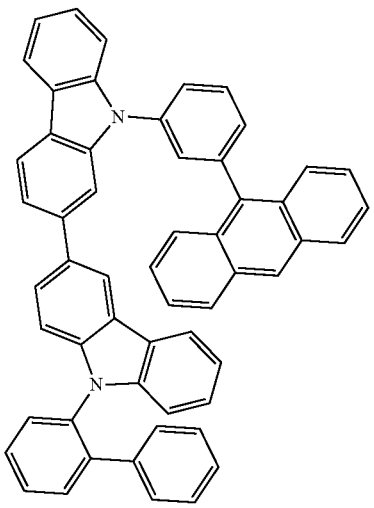
2-47
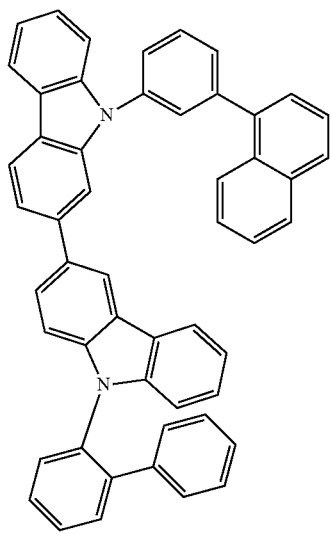
2-50
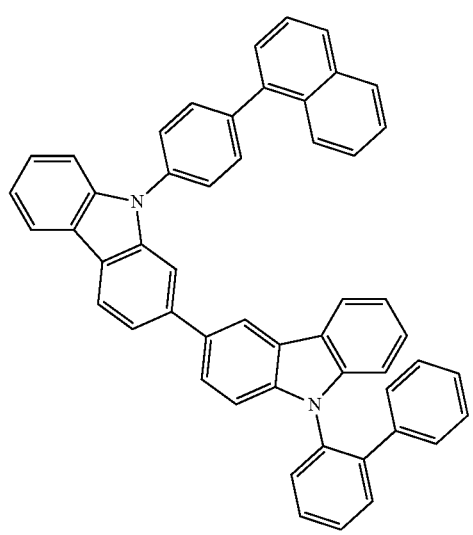

2-51
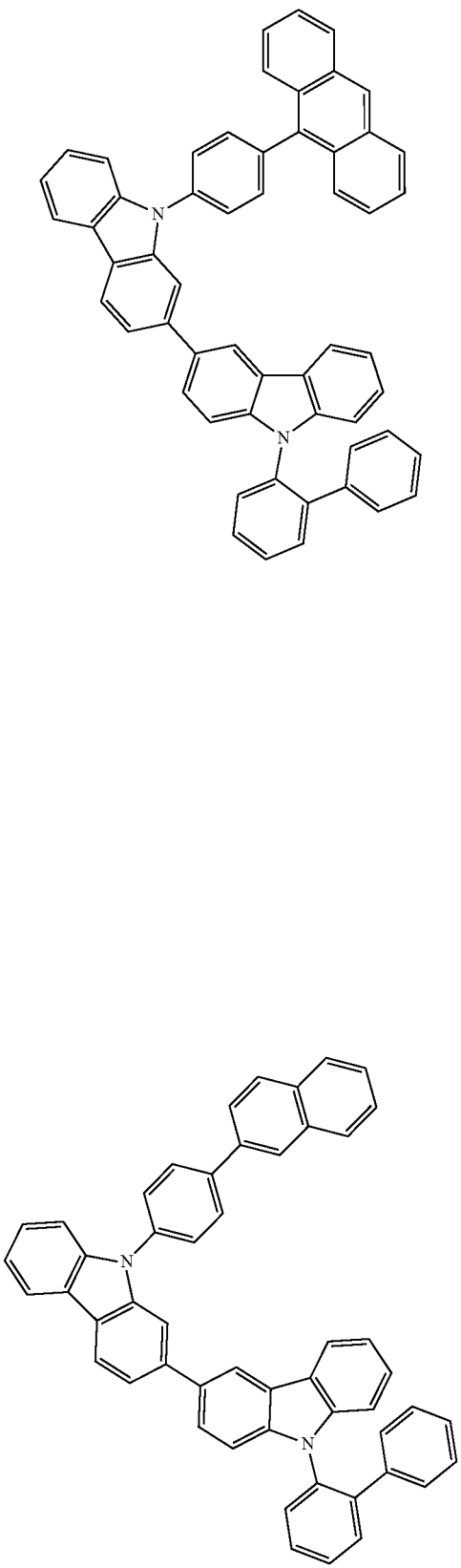
2-52
2-53
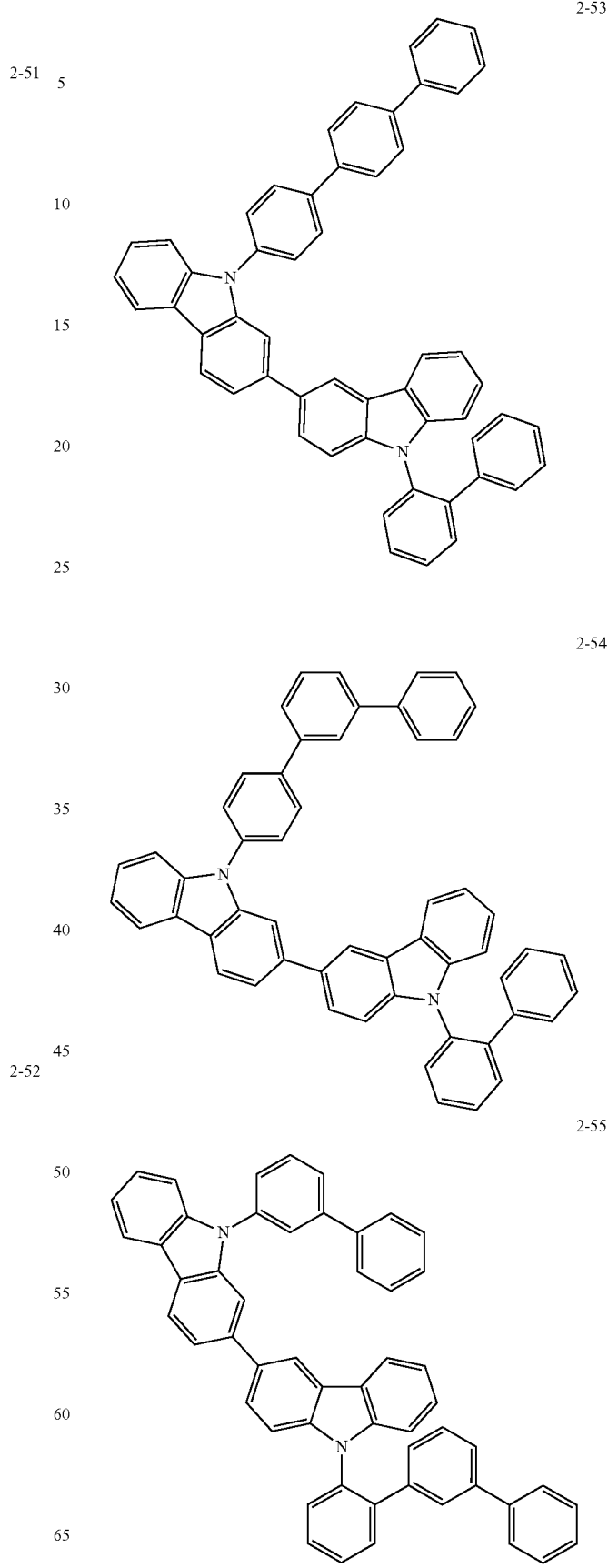
2-54
2-55

2-56
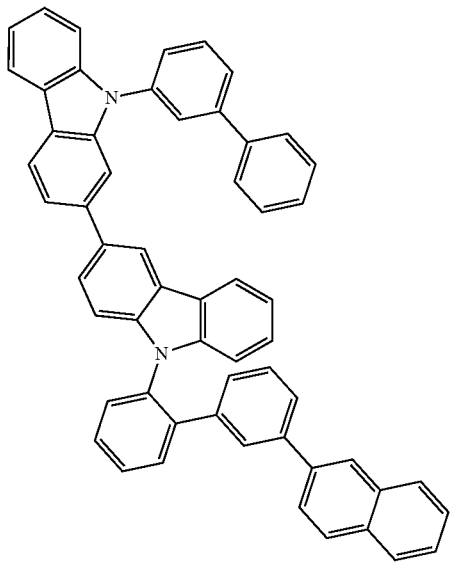
2-57
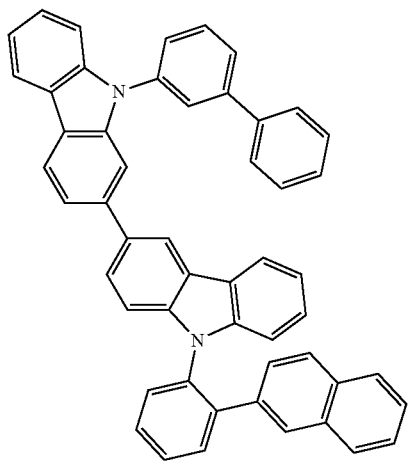
2-58
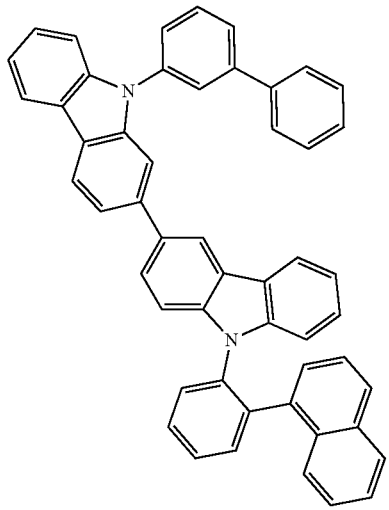
2-59
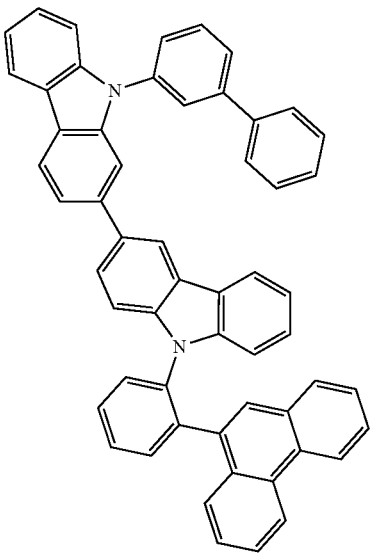
[C16]
2-60
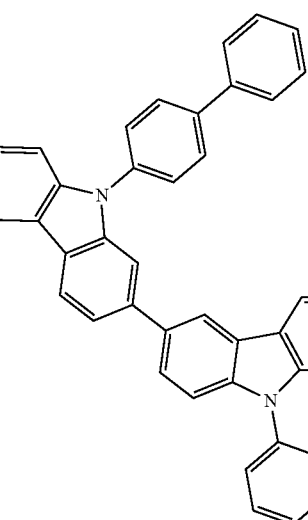
2-61
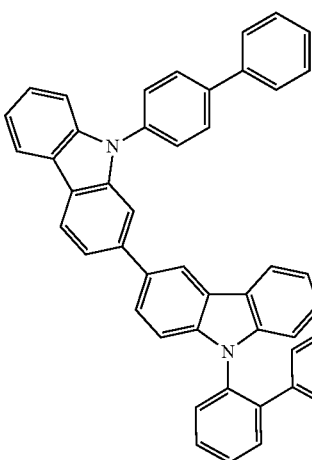

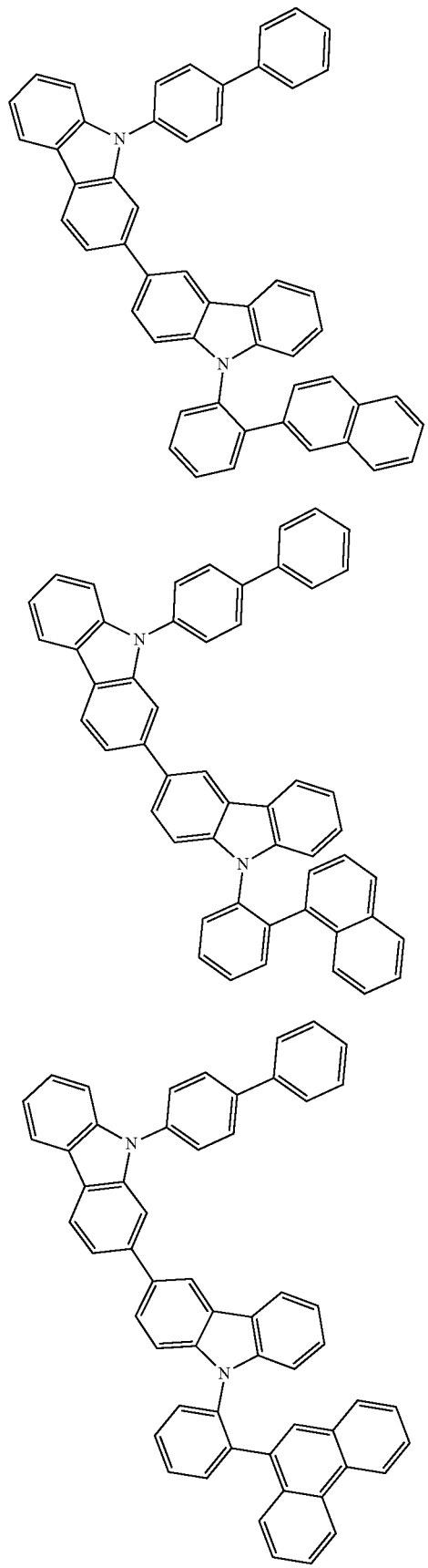
2-62
2-63
2-64
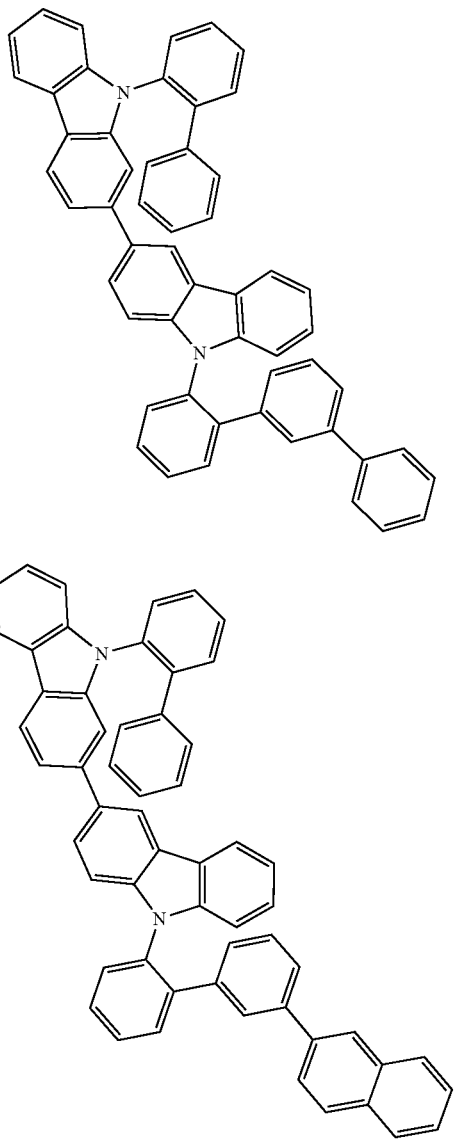
2-65
2-66
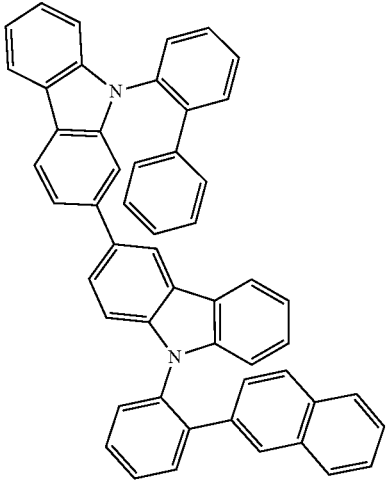
2-67

-continued
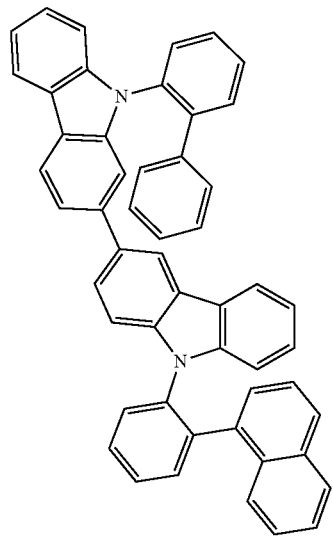
2-68
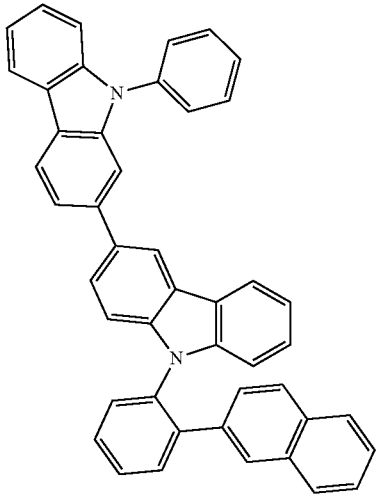
2-71
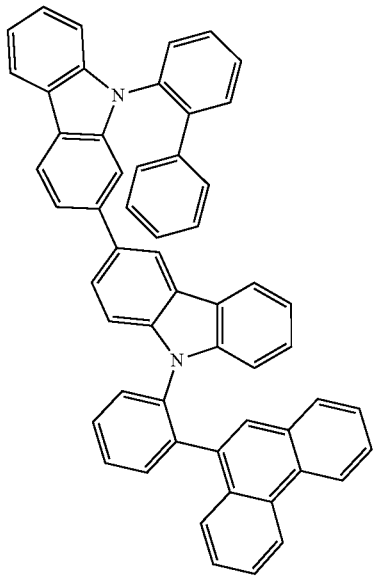
2-69
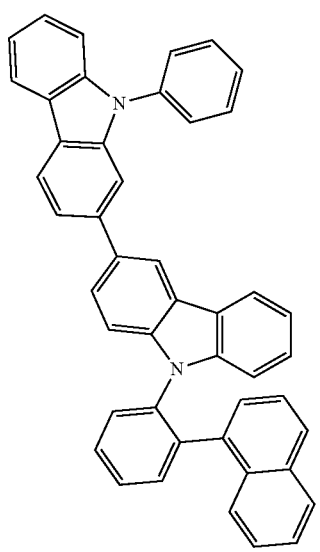
2-72
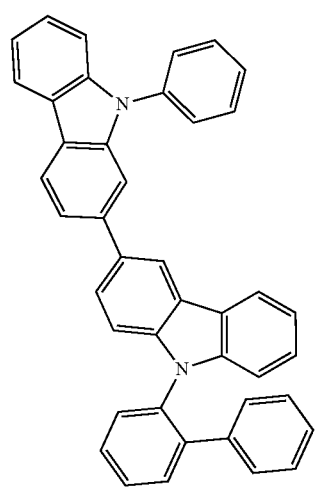
2-70
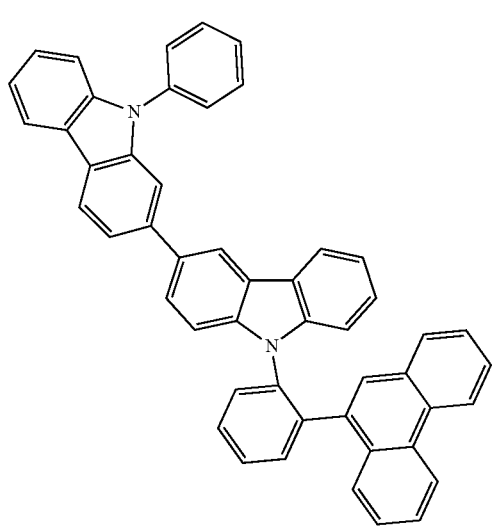
2-73

2-74
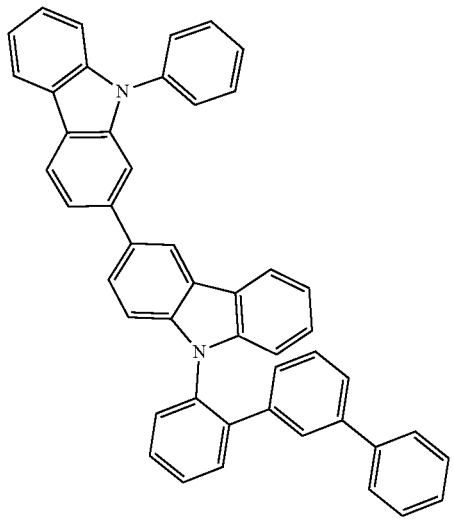
2-75
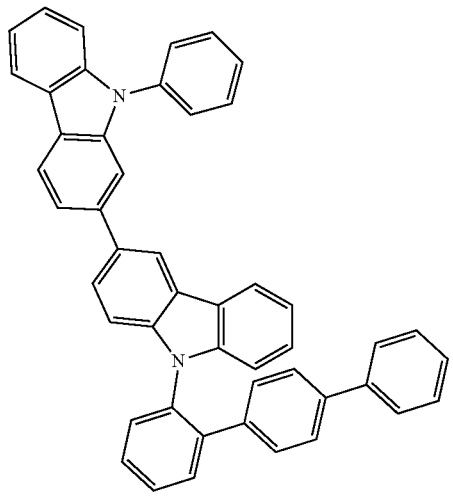
2-76
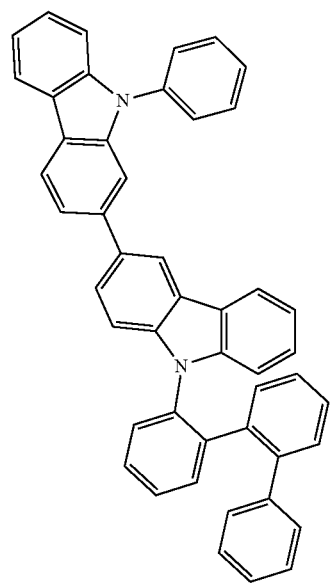
2-77
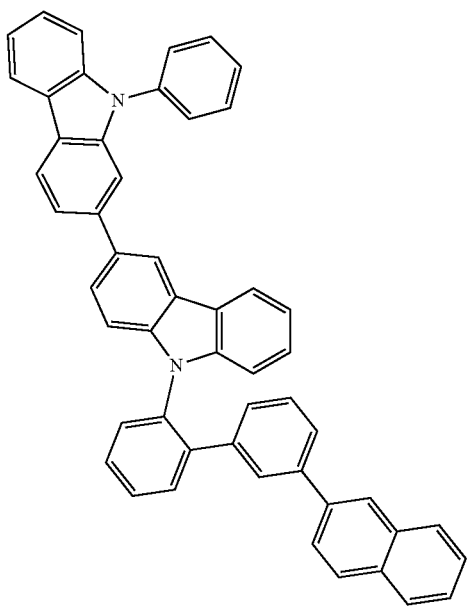
2-78
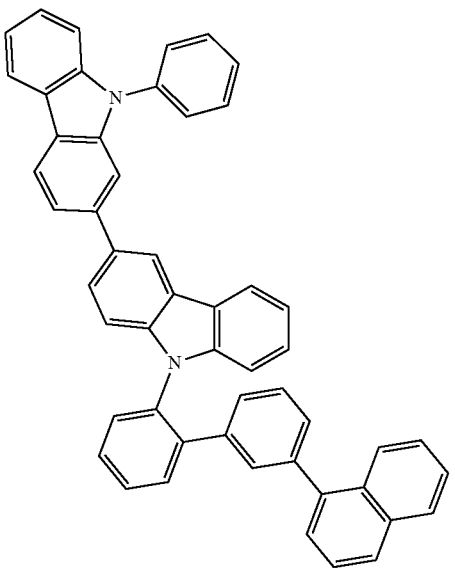

[C17]
2-79
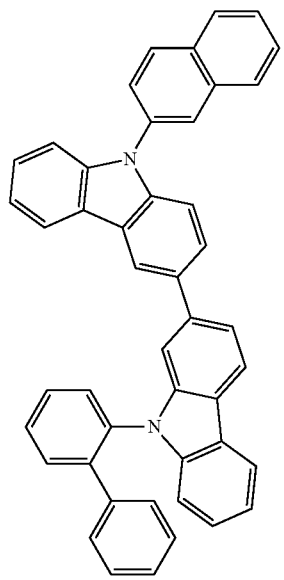
2-80
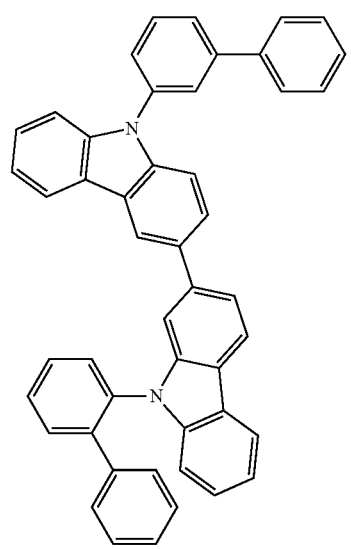
2-81
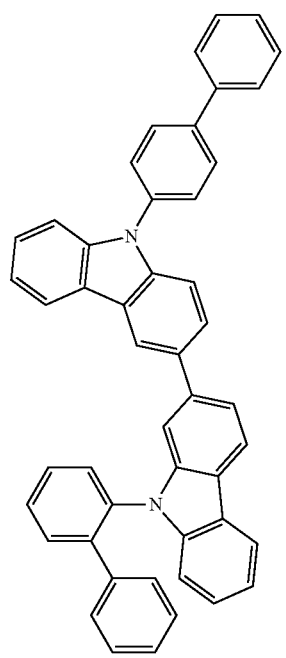
2-82
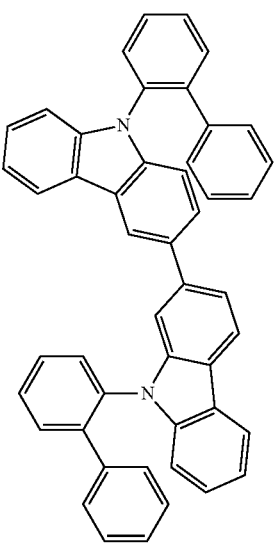

2-83
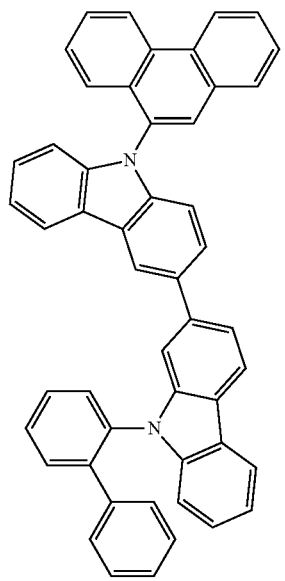
2-85
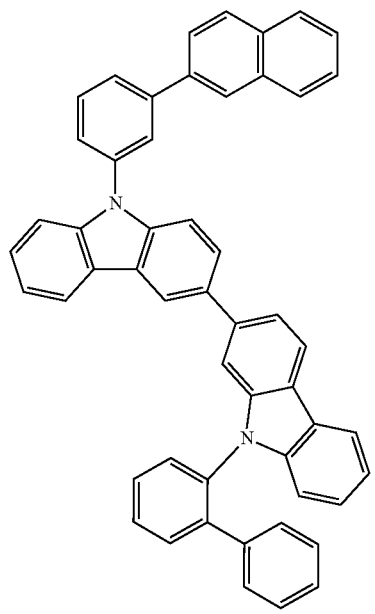
2-84
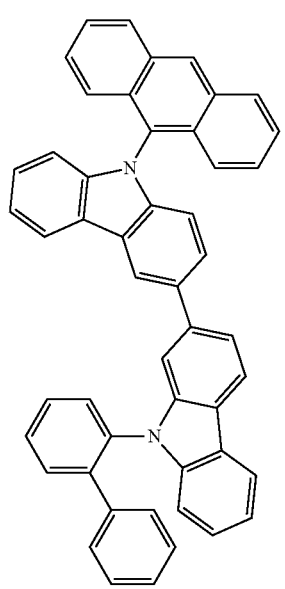
2-86
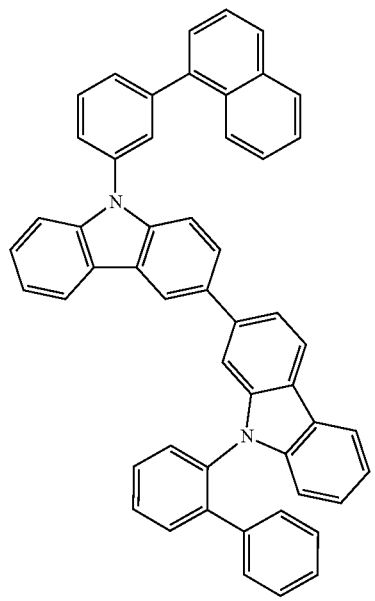

101
-continued
2-87
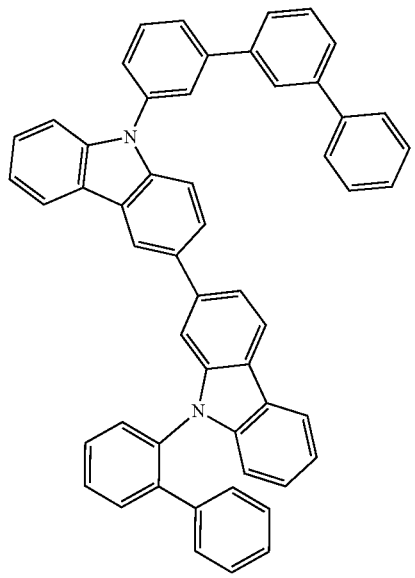
2-88
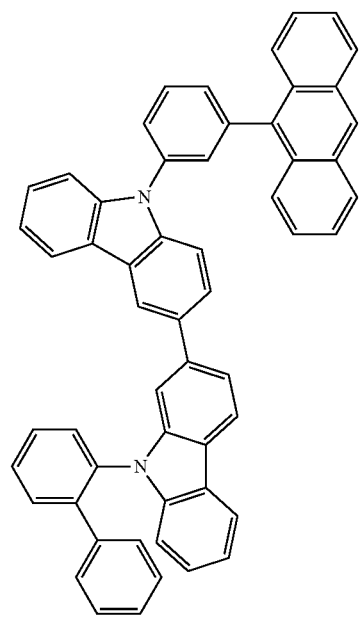
102
-continued
2-89
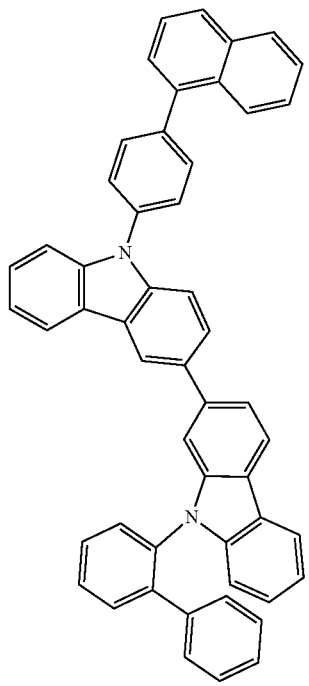
2-90
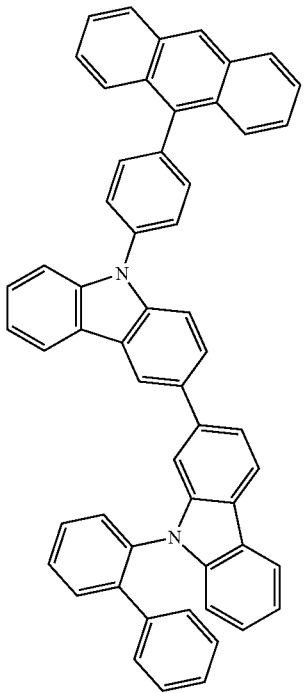

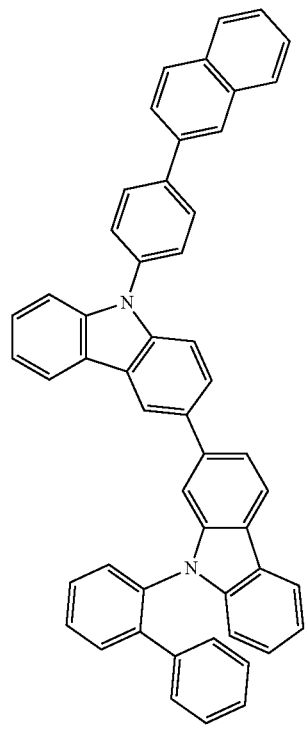
2-91
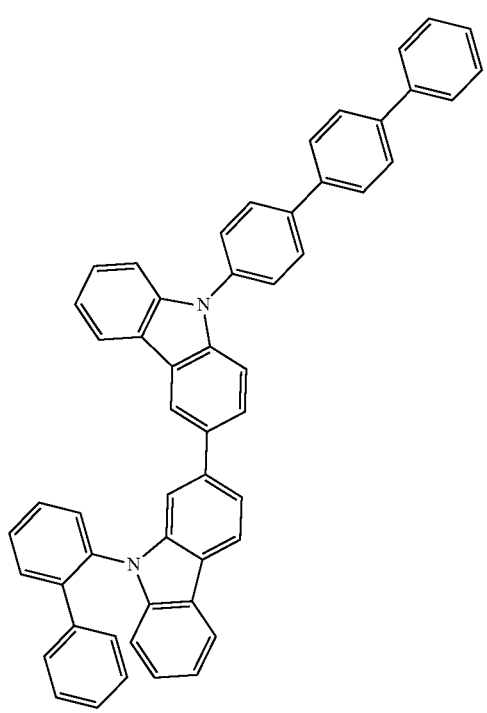
2-92
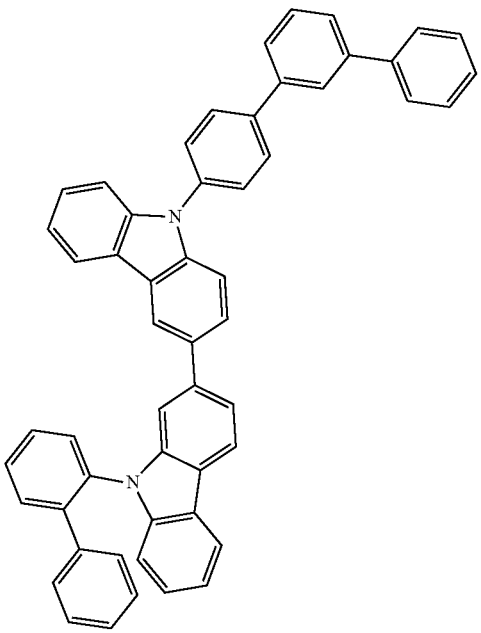
2-93
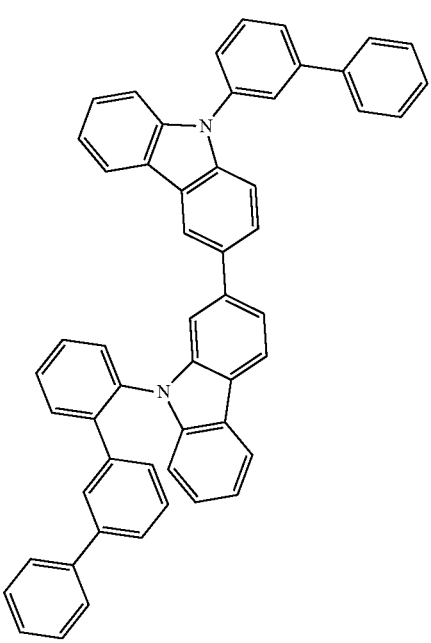
2-94

-continued
2-95
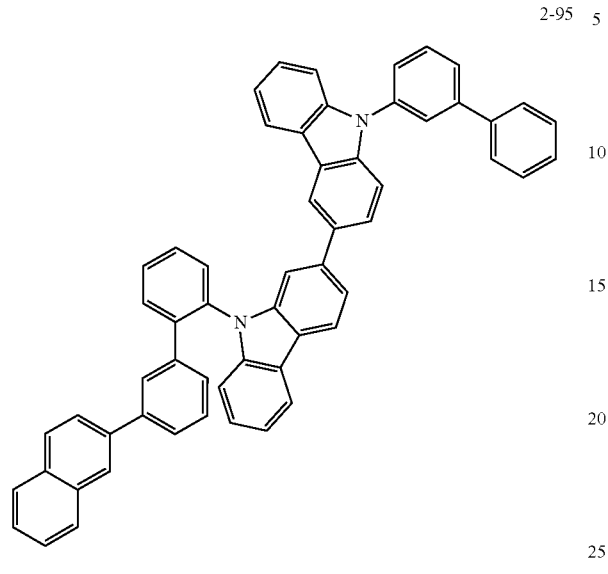
2-97
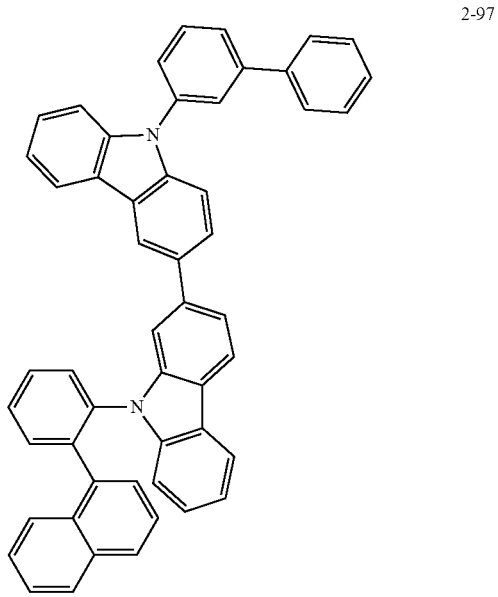
2-96
2-98
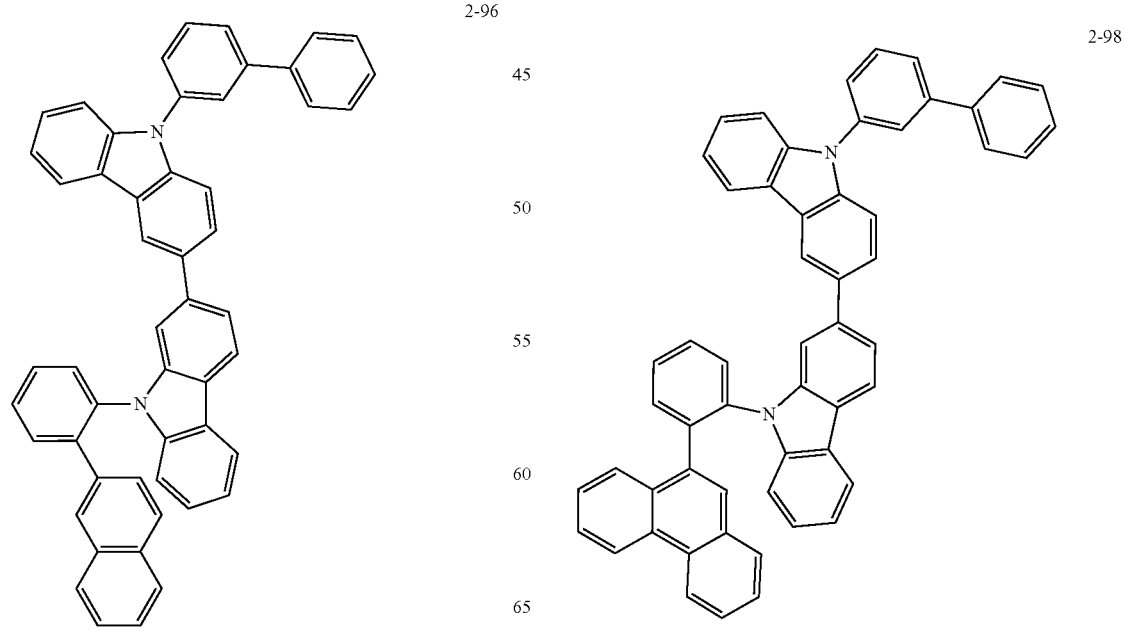

[C18]
2-99
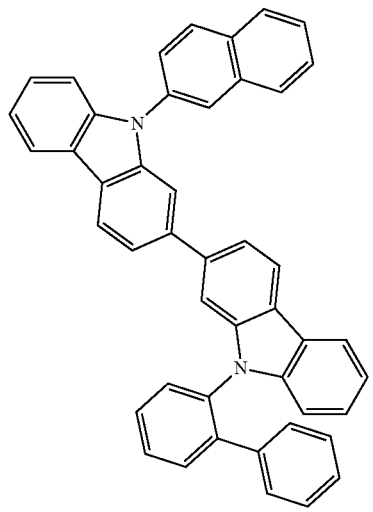
2-100
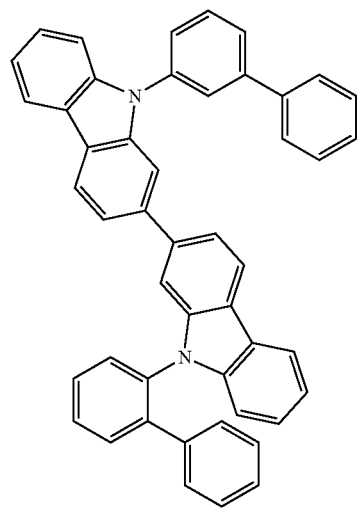
2-101
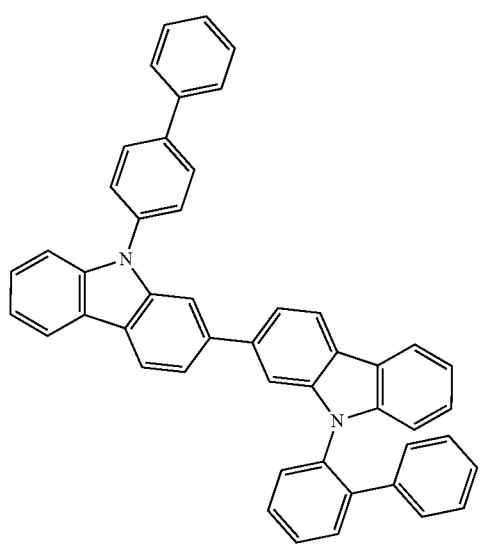
2-102
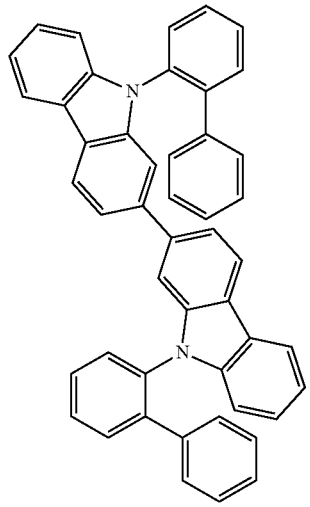
2-103
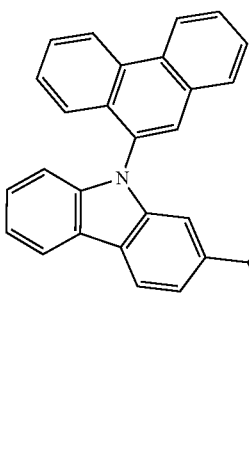
2-104
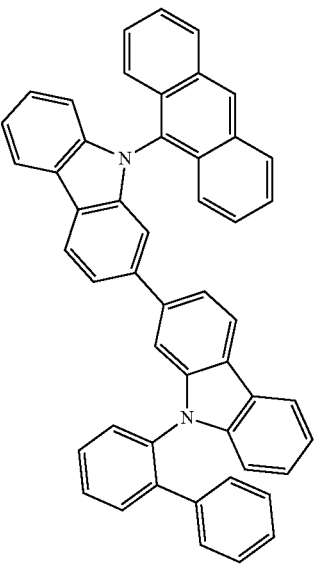

2-105
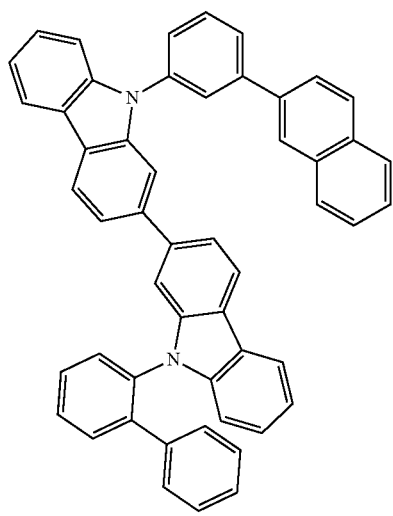
2-106
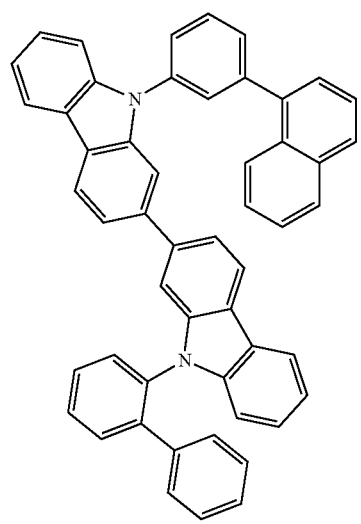
2-107
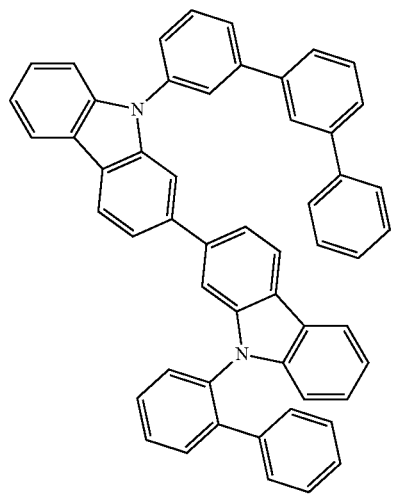
2-108
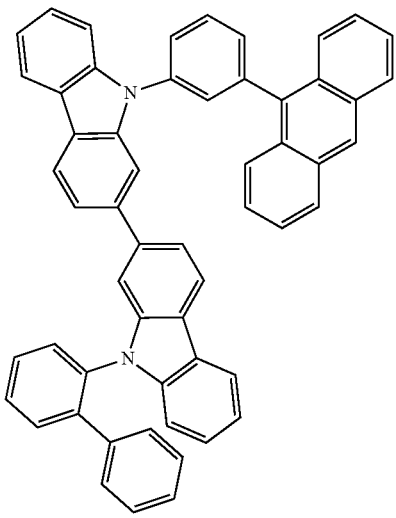
2-109
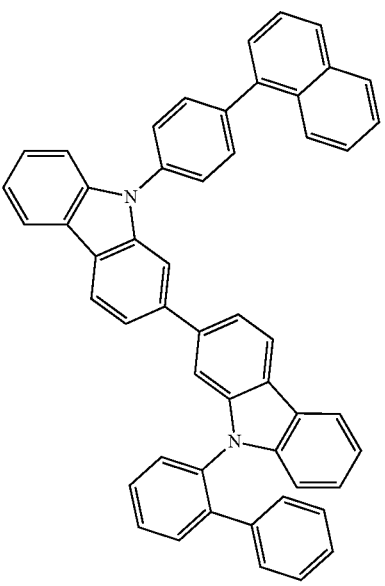

2-110
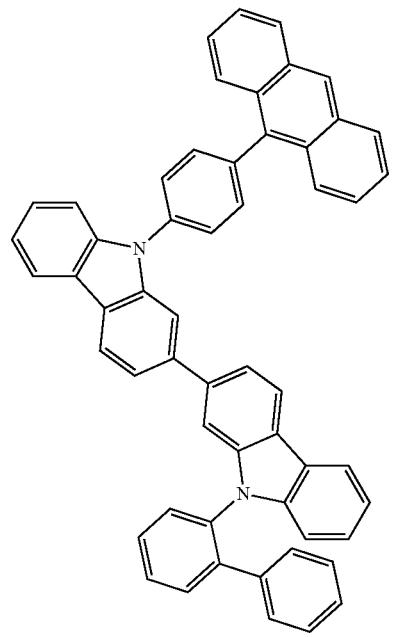
2-111
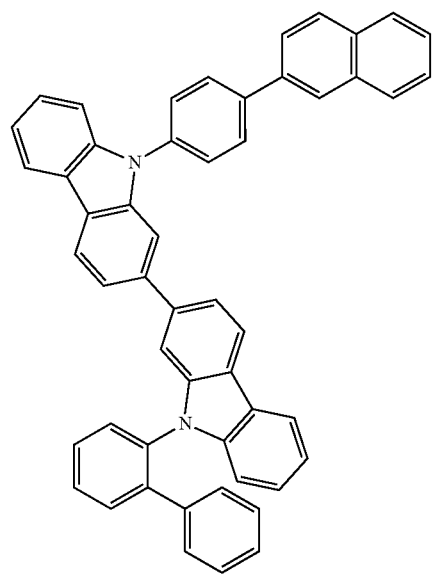
2-112
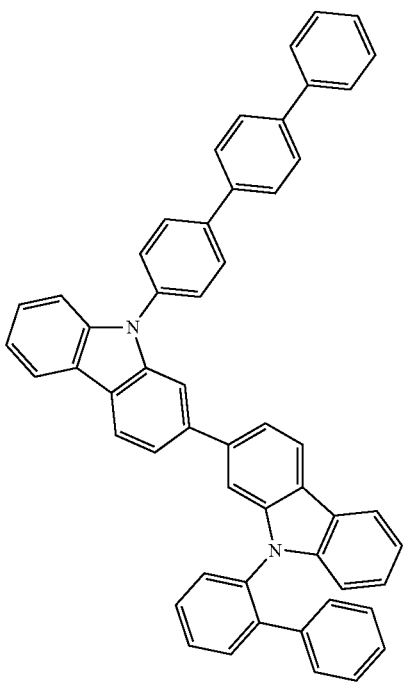
2-113
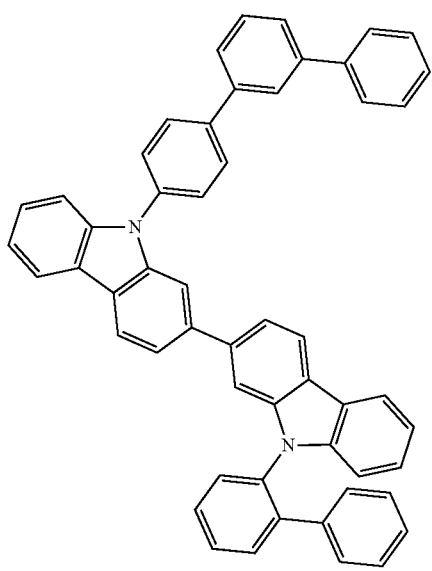

2-114
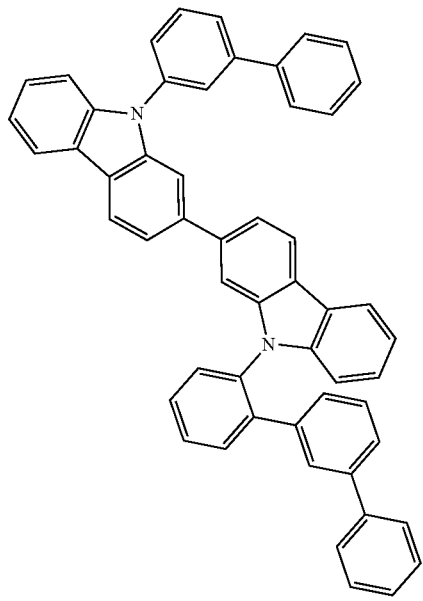
2-116
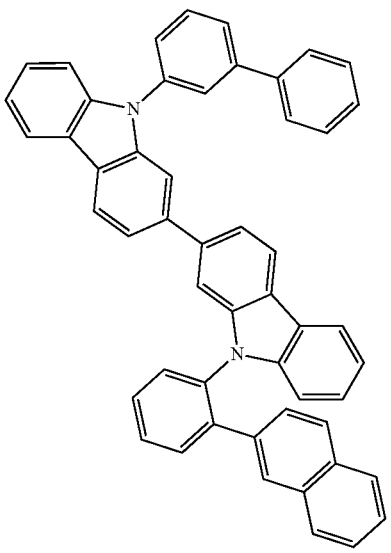
2-115
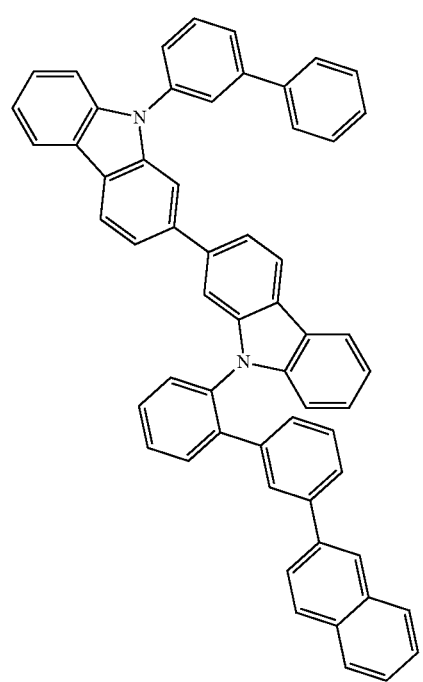
2-117
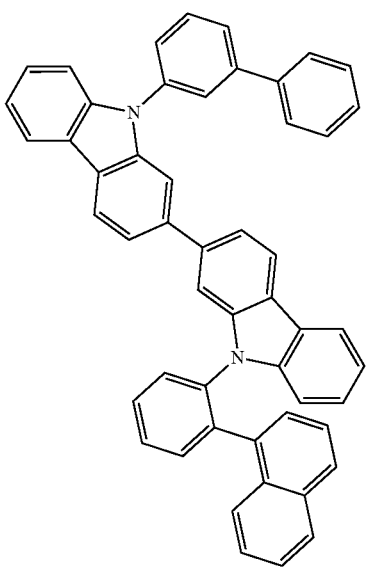

2-118
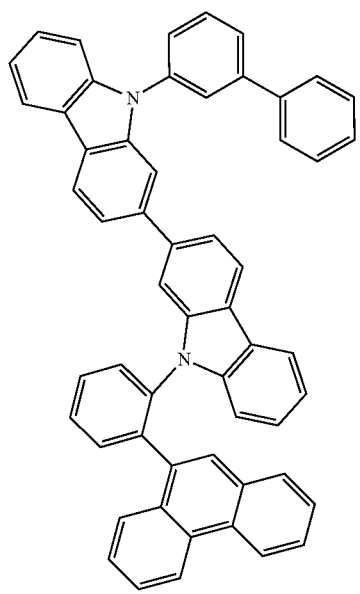
2-119
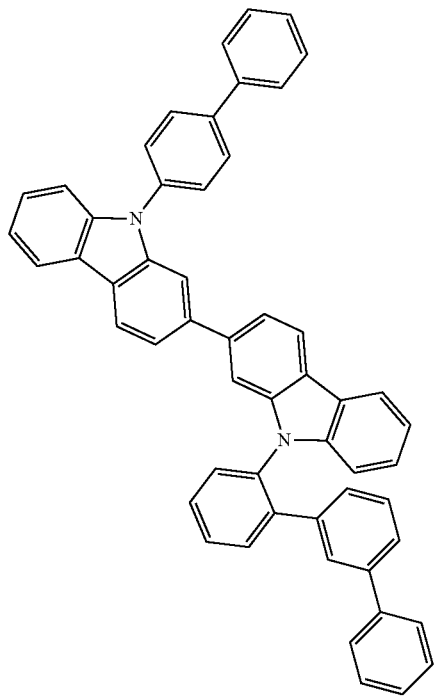
2-120
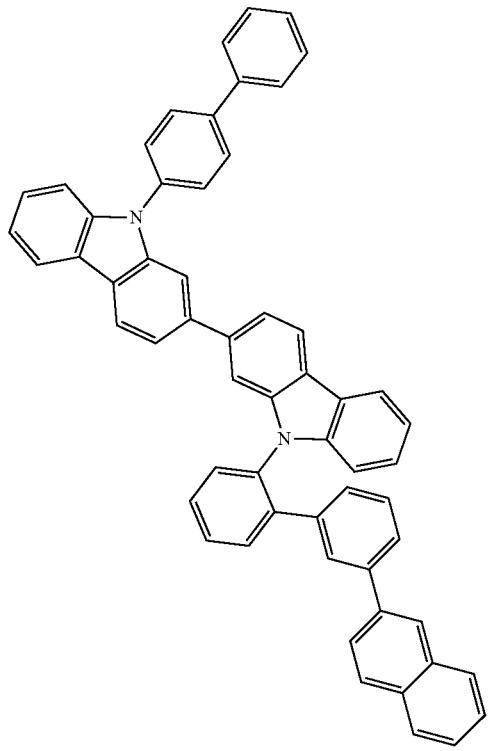
2-121
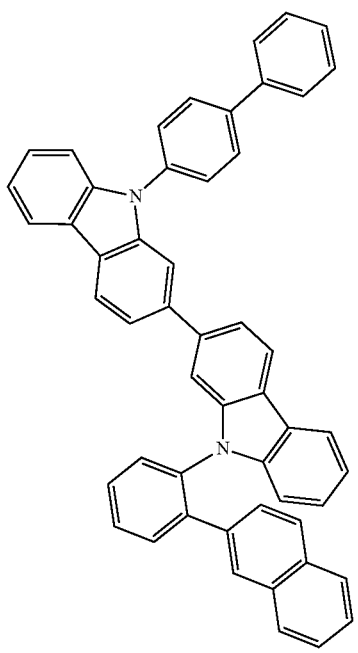

2-122
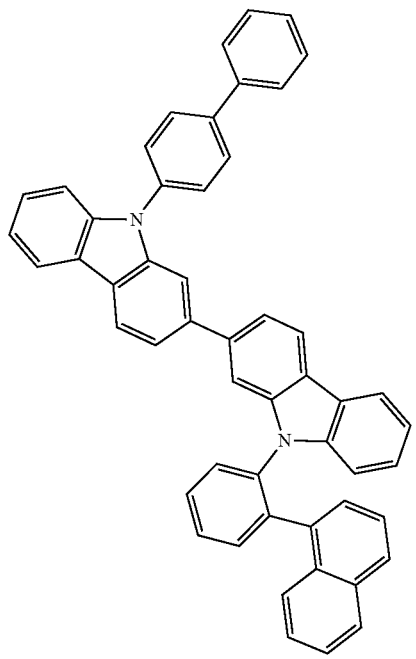
2-124
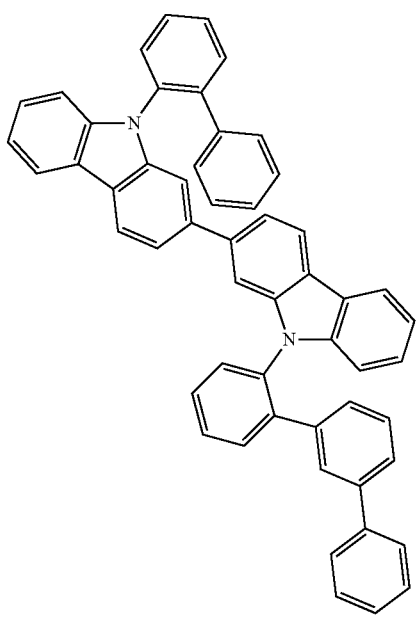
2-123
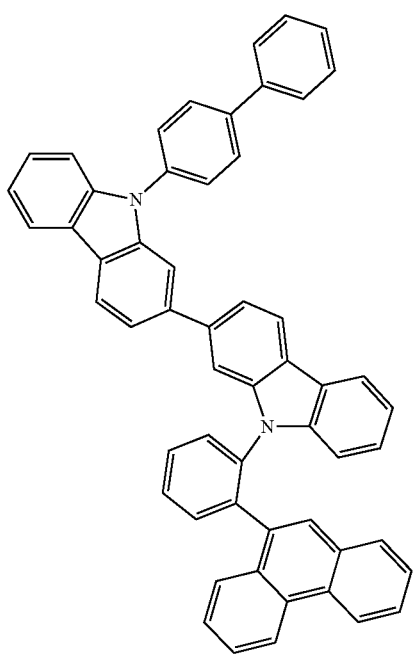
2-125
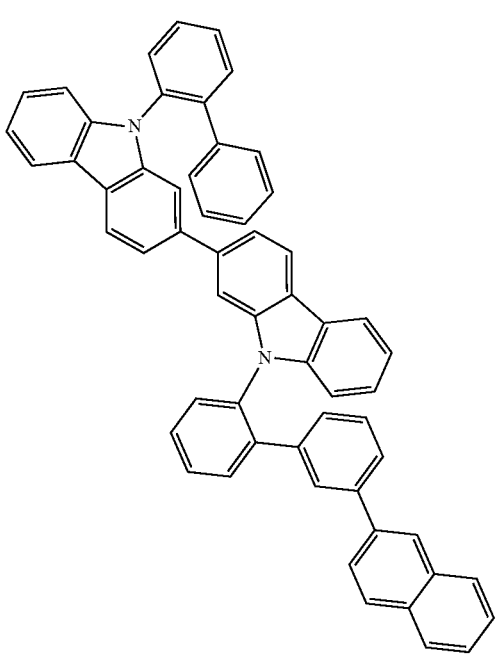

1-126
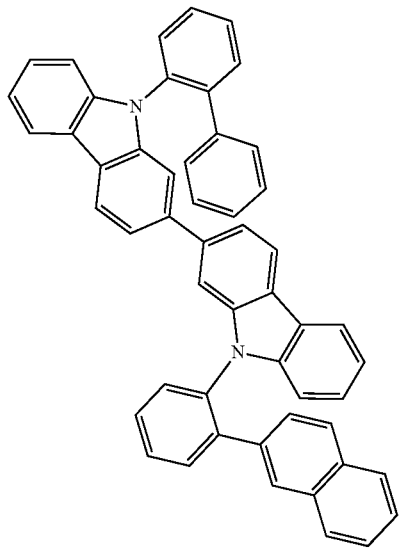
1-127
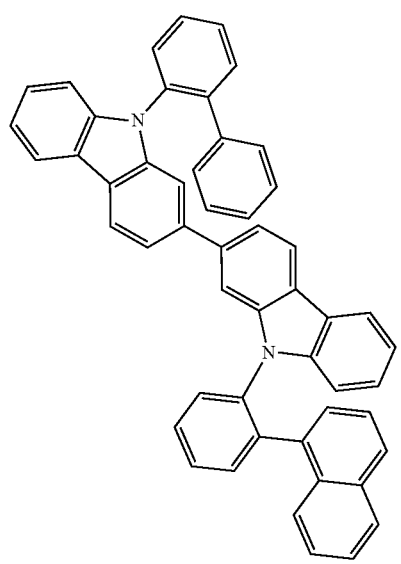
2-128
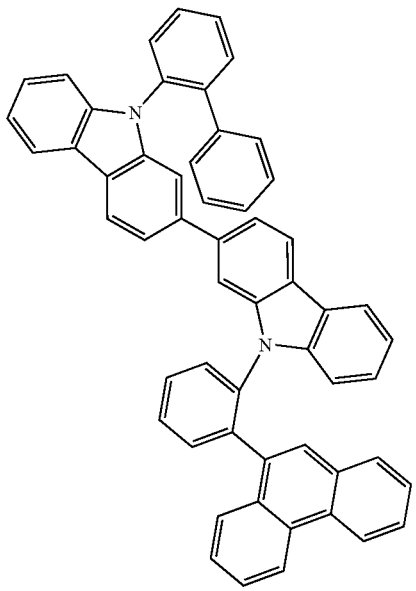
2-129
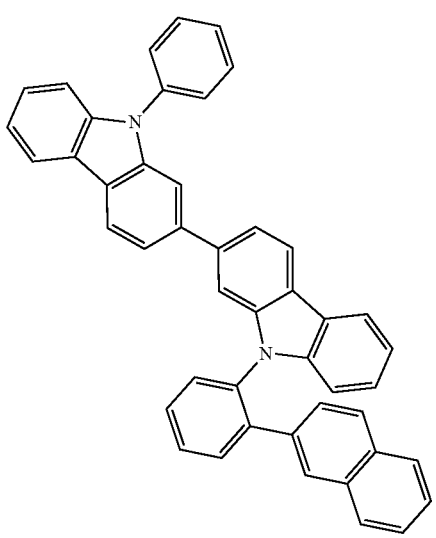
2-130

-continued
2-131
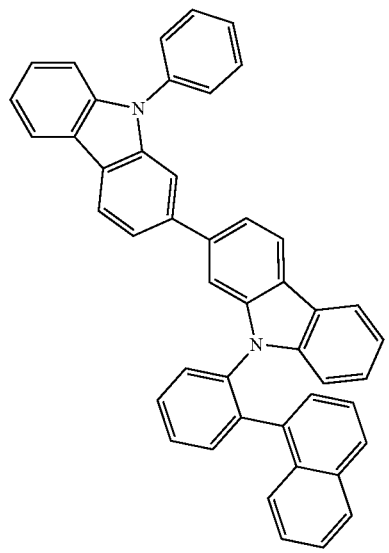
2-132
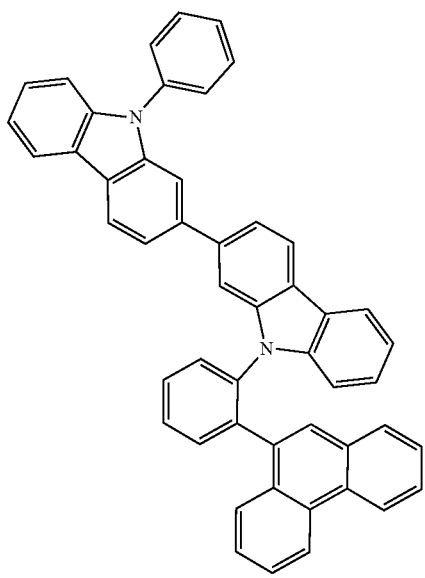
-continued
2-133
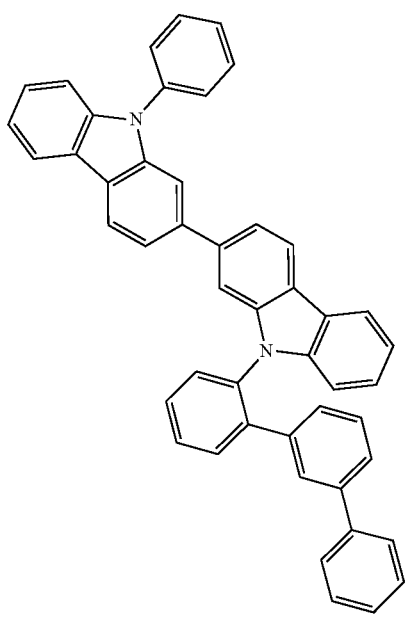
2-134
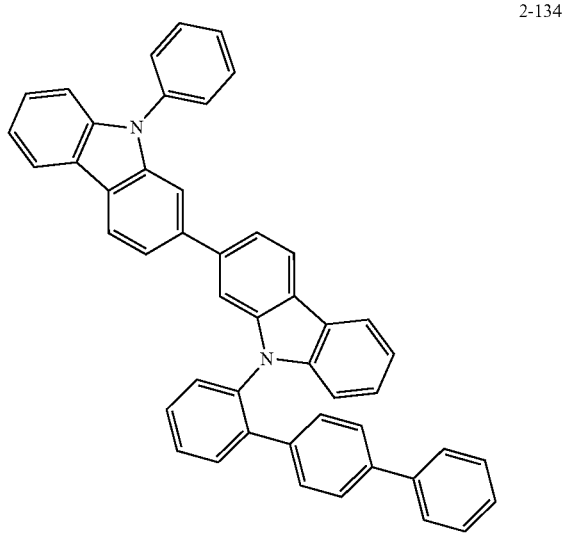

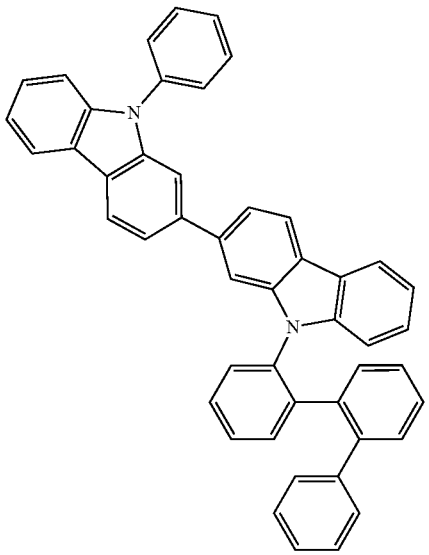

2-135

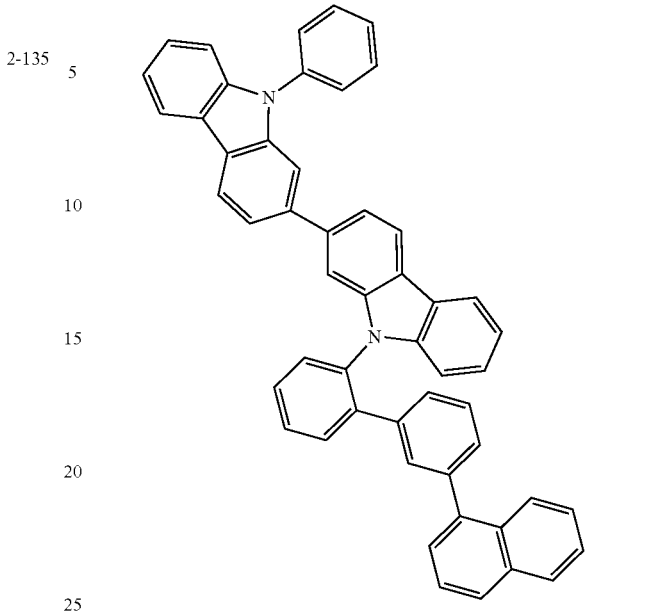

2-137

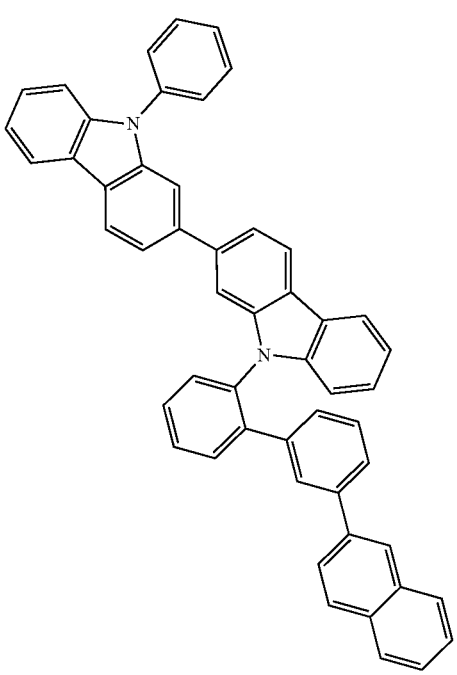

2-136

An excellent organic EL element can be provided by the use, as host material in a light-emitting layer, of a first host selected from compounds represented by general formula (1) and a second host selected from compounds represented by general formula (2).

The first host and the second host may be used by vapor deposition individually from different vapor deposition sources; however, preferably they are premixed prior to vapor deposition to form a premix and the light-emitting layer is then formed by simultaneous vapor deposition of this premix from one vapor deposition source. In this case, the light-emitting dopant material required for formation of the light-emitting layer, or another host used on an optional basis, may be mixed in the premix; however, vapor deposition from separate vapor deposition sources may be carried out when there is a large difference in the temperatures that provide a desirable vapor pressure.

With regard to the mixing ratio (weight ratio) between the first host and the second host, the proportion of the first host with reference to the sum of the first host and the second host may be 20% to 60% and is preferably greater than 20% and less than 55% and is more preferably 40% to 50%.

In addition, the difference in the electron affinities (EA) between the first host and the second host is preferably greater than 0.1 eV and less than 0.6 eV. The value of the EA can be determined on a thin film of the host material using the value of the ionization potential (IP) yielded by photo-electron spectroscopy and the value of the energy gap determined from the absorption edge when the absorption spectrum is measured.

The structure of the organic EL element according to the present invention is described below with reference to the drawing, but the structure of the organic EL element according to the present invention is not limited to or by this.

FIG. 1 is a cross-sectional diagram that shows an example of the structure of a general organic EL element used in the present invention. 1 refers to a substrate; 2 refers to an anode; 3 refers to a hole injection layer; 4 refers to a hole transport layer; 5 refers to a light-emitting layer; 6 refers to an electron transport layer; and 7 refers to a cathode. The organic EL element according to the present invention may have an exciton blocking layer adjacent to the light-emitting layer and may have an electron blocking layer between the light-emitting layer and the hole injection layer. The exciton blocking layer may be inserted on either the cathode side or cathode side of the light-emitting layer or may be inserted on both sides at the same time. The organic EL element according to the present invention has an anode, light-emitting layer, and cathode as essential layers, but preferably has, in addition to the essential layers, a hole injection/transport layer and an electron injection/transport layer and also preferably has a hole blocking layer between the light-emitting layer and the electron injection/transport layer. A hole injection/transport layer denotes either or both of a hole injection layer and a hole transport layer, while an electron injection layer denotes either or both of an electron injection layer and an electron transport layer.

The structure may also be the reverse of that in FIG. 1, i.e., the stacking sequence on the substrate 1 may be cathode 7, electron transport layer 6, light-emitting layer 5, hole transport layer 4, and anode 2. Layers may also be added and omitted as necessary in this case.

—Substrate—

The organic EL element according to the present invention is preferably supported on a substrate. This substrate is not particularly limited and may be a substrate as heretofore used in organic EL elements; for example, a substrate of glass, a transparent plastic, quartz, and so forth may be used.

—Anode—

A material composed of a metal, alloy, or electroconductive compound that has a high work function (4 eV or more), or of a mixture of the preceding, is preferably used for the anode material in the organic EL element. Specific examples of such an electrode material are metals such as Au and conductive transparent materials such as CuI, indium tin oxide (ITO), $SnO_2$, and ZnO. An amorphous material that can form a transparent conductive film, such as IDIXO ($In_2O_3$—ZnO), may also be used. The anode may be formed by forming a thin film of the electrode material by a method such as vapor deposition or sputtering and then forming a pattern with the desired shape by photolithography. When pattern accuracy is not a stringent requirement (approximately 100 μm or more), a pattern may be formed during vapor deposition or sputtering of the electrode material through a mask with the desired shape. Otherwise, a wet film-forming method, e.g., a printing method or a coating method, may be used when a coatable substance such as an organic conductive compound is used. The anode desirably has a transmittance greater than 10% when the emitted light is extracted through the anode, and the anode preferably has a sheet resistance of several hundred Ω/sq. or less. The film thickness will vary depending on the material, but is selected generally from the range of 10 to 1000 nm and preferably 10 to 200 nm.

—Cathode—

On the other hand, a material composed of a metal (referred to as electron-injecting metal), alloy, or electroconductive compound that has a low work function (4 eV or less), or a mixture of the preceding, is used for the cathode material. Specific examples of such an electrode material are sodium, sodium-potassium alloys, magnesium, lithium, magnesium/copper mixtures, magnesium/silver mixtures, magnesium/aluminum mixtures, magnesium/indium mixtures, aluminum/aluminum oxide ($Al_2O_3$) mixtures, indium, lithium/aluminum mixtures, rare-earth metals, and so forth. Among these, and considered from the standpoint of the electron injectability and ability to withstand oxidation and so forth, mixtures of an electron-injecting metal and a second metal that is stable and has a higher work function than the electron-injecting metal, e.g., a magnesium/silver mixture, magnesium/aluminum mixture, magnesium/indium mixture, aluminum/aluminum oxide mixture, lithium/aluminum mixture, aluminum, and so forth, are advantageous. The cathode may be produced by forming a thin film of these cathode materials by a procedure such as vapor deposition or sputtering. The cathode preferably has a sheet resistance of several hundred Ω/sq. or less, and the film thickness is selected from the range of generally 10 nm to 5 μm and preferably 50 to 200 nm. In order to transmit the emitted light, either of the anode and cathode in the organic EL element is advantageously transparent or semi-transparent due to the improved luminance.

A transparent or semitransparent cathode can be fabricated by forming the aforementioned metal at a film thickness of 1 to 20 nm at the cathode and subsequently forming thereon an electroconductive transparent material as indicated above in the description of the anode. The application of this procedure enables the fabrication of an element in which both the anode and cathode exhibit transparency.

—Light-Emitting Layer—

The light-emitting layer is a layer that emits light after the generation of excitons by the recombination of holes and electrons injected from the anode and cathode, respectively, and an organic light-emitting dopant material and a host material are present in the light-emitting layer.

A first host represented by general formula (1) and a second host represented by general formula (2) are used as the host material in the light-emitting layer. While a combination with a single known host material or a plurality of known host materials may also be used, the amount of use thereof, with reference to the sum of the host materials, should be not more than 50 wt % and is preferably not more than 25 wt %.

The first host and second host can each be vapor deposited from different vapor deposition sources, or the first host and the second host can be vapor deposited at the same time from a single vapor deposition source by making a premix by premixing prior to vapor deposition.

When the first host and second host are used after premixing, a small difference in the 50% weight loss temperatures ($T_{50}$) is desirable in order to achieve the highly reproducible fabrication of organic EL elements that exhibit excellent characteristics. The 50% weight loss temperature refers to the temperature at which a 50% reduction in weight occurs when the temperature is raised from room temperature to 550° C. at a rate of 10° C./minute in a TG-DTA measurement under reduced pressure (50 Pa) and a nitrogen flow. The greatest amount of evaporation or volatilization by sublimation is thought to occur at around these temperatures.

This difference in the 50% weight loss temperatures between the first host and second host is preferably within 20° C. and is more preferably within 15° C. Known methods, e.g., grinding/mixing and so forth, may be used for the premixing method, and mixing to uniformity is desirably carried out to the greatest extent possible.

When a phosphorescent light-emitting dopant is used for the light-emitting dopant material, the phosphorescent light-emitting dopant preferably contains an organometal complex that contains at least one metal selected from ruthenium, rhodium, palladium, silver, rhenium, osmium, iridium, platinum, and gold. Specifically, the iridium complexes described in J. Am. Chem. Soc. 2001, 123, 4304 and Japanese Translation of PCT Application No. 2013-53051 are preferably used, but there is no limitation thereto.

Only a single phosphorescent light-emitting dopant material may be incorporated in the light-emitting layer or two or more may be incorporated. The content of the phosphorescent light-emitting dopant material, with reference to the host material, is preferably 0.1 to 30 wt % and is more preferably 1 to 20 wt %.

The phosphorescent light-emitting dopant material is not particularly limited, but may be specifically exemplified by the following.

[C20]

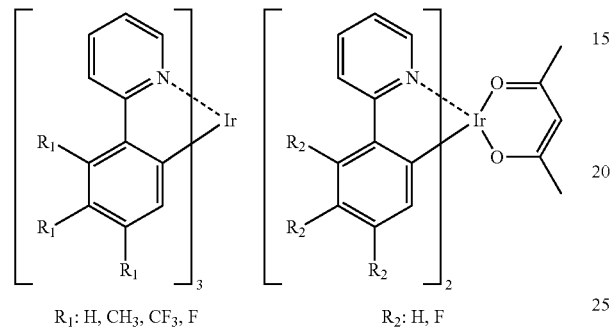

R₁: H, CH₃, CF₃, F          R₂: H, F

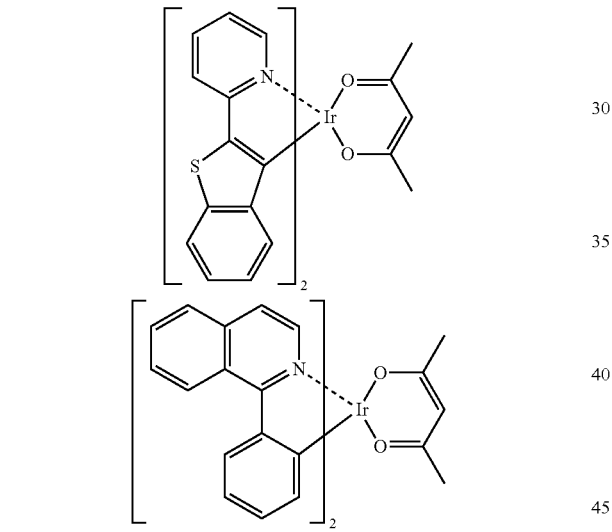

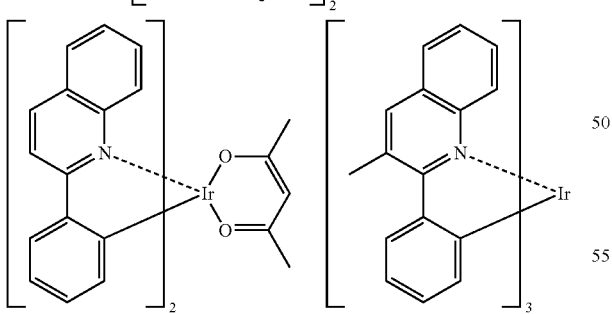

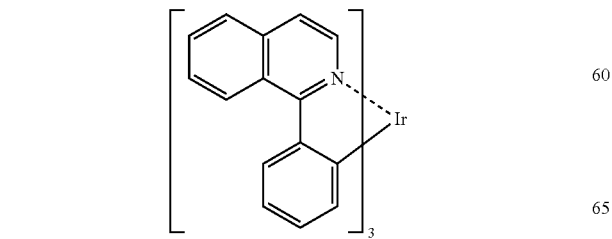

-continued

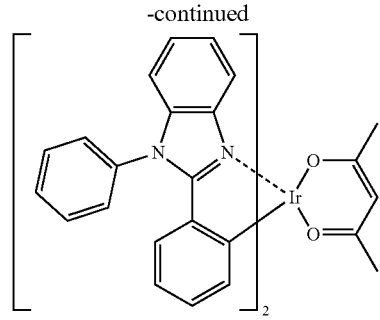

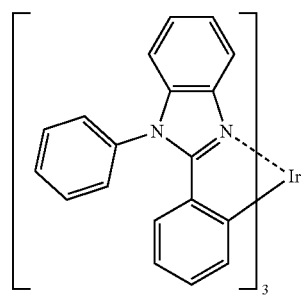

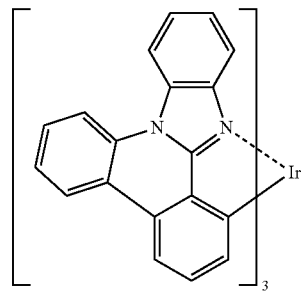

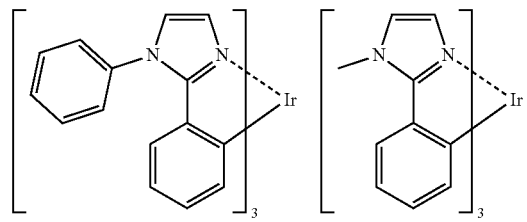

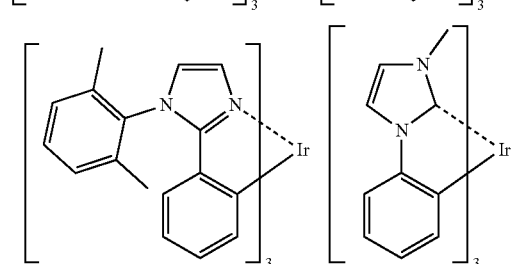

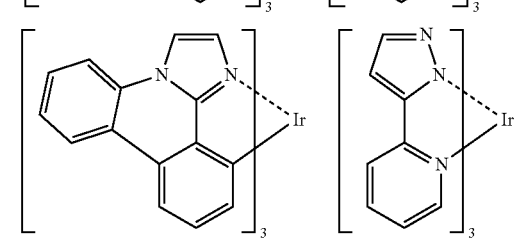

-continued

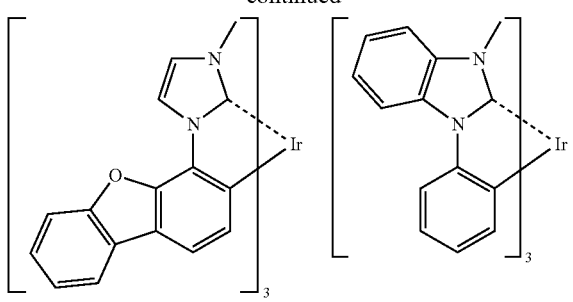

[C21]

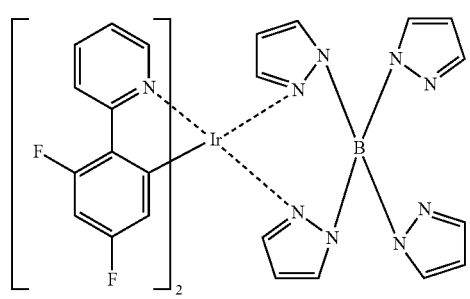

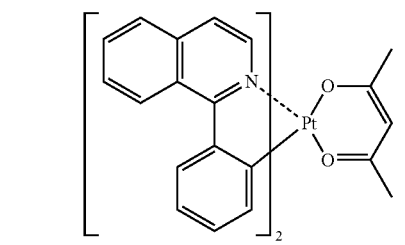

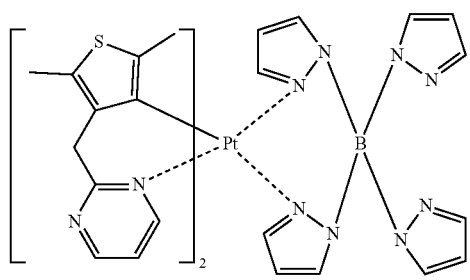

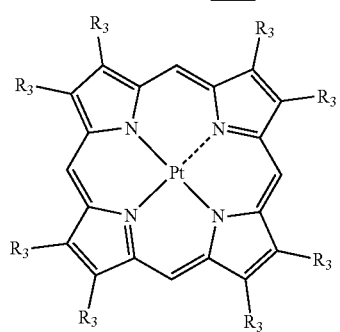

R$_3$: CH$_3$, CH$_2$CH$_3$

-continued

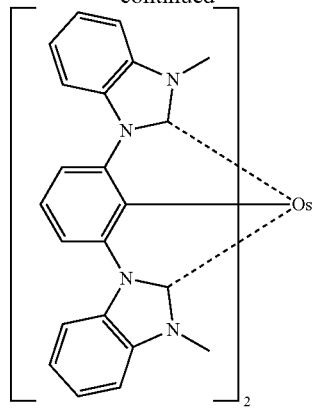

For the case of use of a fluorescent light-emitting dopant as the light-emitting dopant material, the fluorescent light-emitting dopant is not particularly limited, but can be exemplified by benzoxazole derivatives, benzothiazole derivatives, benzimidazole derivatives, styrylbenzene derivatives, polyphenyl derivatives, diphenylbutadiene derivatives, tetraphenylbutadiene derivatives, naphthalimide derivatives, coumarin derivatives, condensed aromatic compounds, perinone derivatives, oxadiazole derivatives, oxazine derivatives, aldazine derivatives, pyralizine derivatives, cyclopentadiene derivatives, bisstyrylanthracene derivatives, quinacridone derivatives, pyrrolopyridine derivatives, thiadiazolopyridine derivatives, styrylamine derivatives, diketopyrrolopyrrole derivatives, and aromatic dimethylidyne compounds; various metal complexes as represented by metal complexes of 8-quinolinol derivatives, metal complexes of pyrromethene derivatives, rare earth complexes, and transition metal complexes; polymer compounds such as polythiophene, polyphenylene, and polyphenylene vinylene; and organosilane derivatives. Condensed aromatic derivatives, styryl derivatives, diketopyrrolopyrrole derivatives, oxazine derivatives, pyrromethene metal complexes, transition metal complexes, and lanthanoid complexes are preferred, while naphthalene, pyrene, chrysene, triphenylene, benzo[c]phenanthrene, benzo[a]anthracene, pentacene, perylene, fluoranthene, acenaphthofluoranthene, dibenzo[a,j]anthracene, dibenzo[a,h]anthracene, benzo[a]naphthalene, hexacene, naphtho[2,1-f]isoquinoline, α-naphthaphenanthridine, phenanthroxazole, quinolino[6,5-f]quinoline, benzothiophanthrene, and so forth are more preferred. These may have an alkyl group, an aryl group, an aromatic heterocyclic group, or a diarylamino group as a substituent.

Only a single fluorescent light-emitting dopant material may be incorporated in the light-emitting layer or two or more fluorescent light-emitting dopant materials may be incorporated. The content of the fluorescent light-emitting dopant material, with reference to the host material, is preferably 0.1 to 20 wt % and is more preferably 1 to 10 wt %.

For the case of use of a thermally activated delayed fluorescence light-emitting dopant as the light-emitting dopant material, the thermally activated delayed fluorescence light-emitting dopant is not particularly limited, but can be exemplified by metal complexes such as tin complexes and copper complexes; the indolocarbazole derivatives described in WO 2011/070963; the cyanobenzene derivatives described in Nature 2012, 492, 234; carbazole derivatives; the phenazine derivatives described in Nature Photonics 2014, 8, 326; oxadiazole derivatives; triazole derivatives; sulfone derivatives; phenoxazine derivatives; and acridine derivatives.
The thermally activated delayed fluorescence light-emitting dopant material is not particularly limited, but may be specifically exemplified by the following.
[C22]
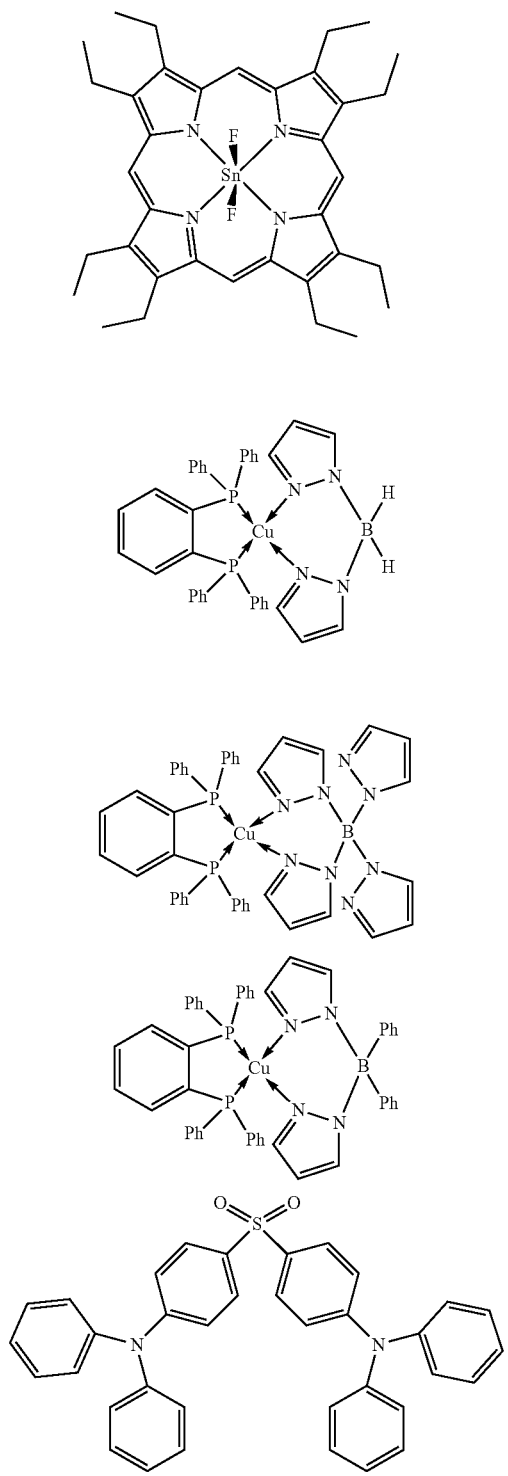
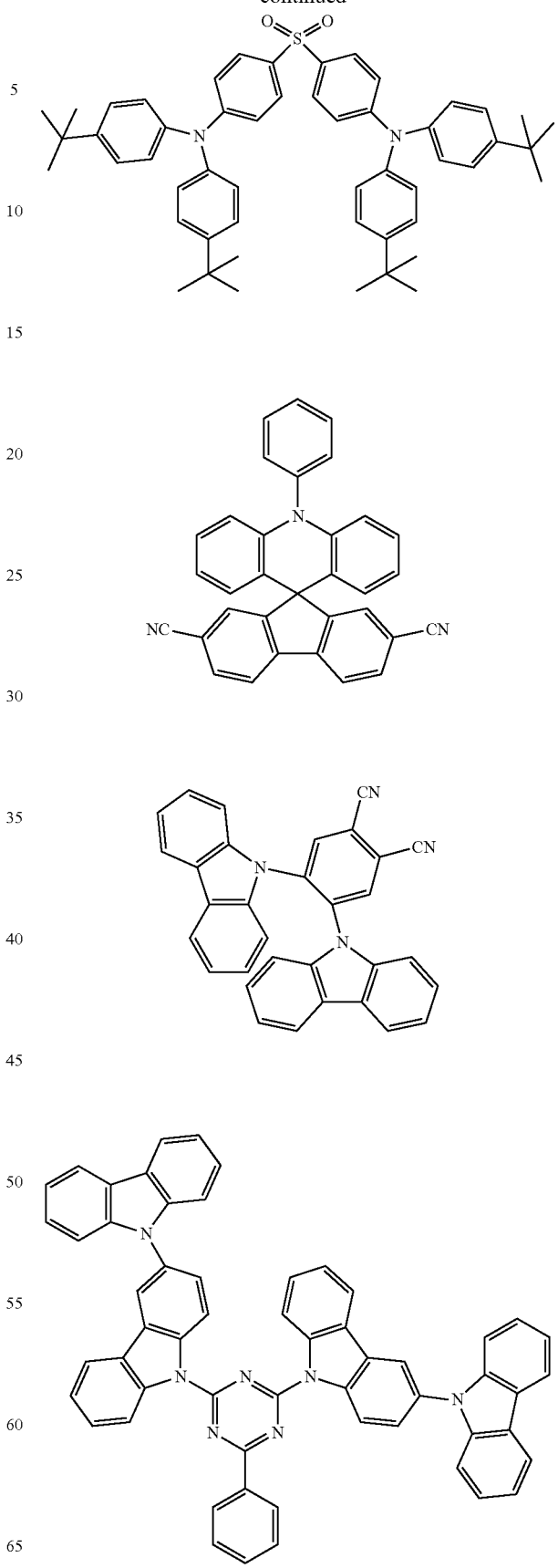

-continued

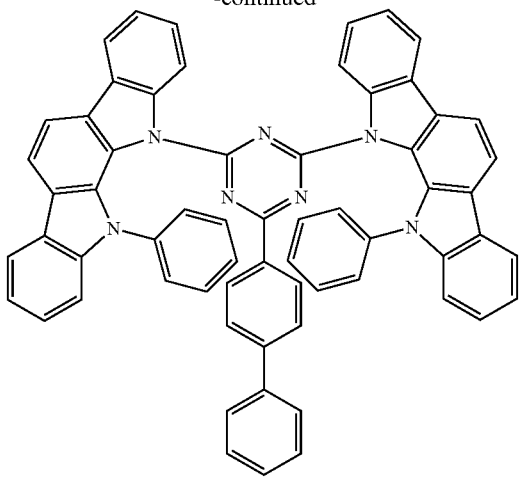

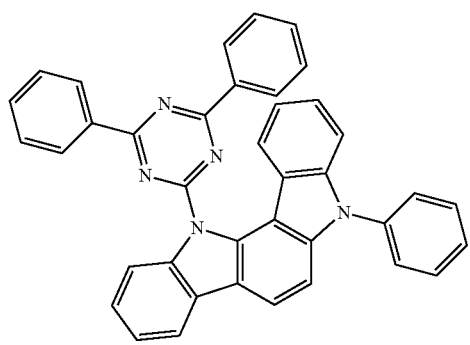

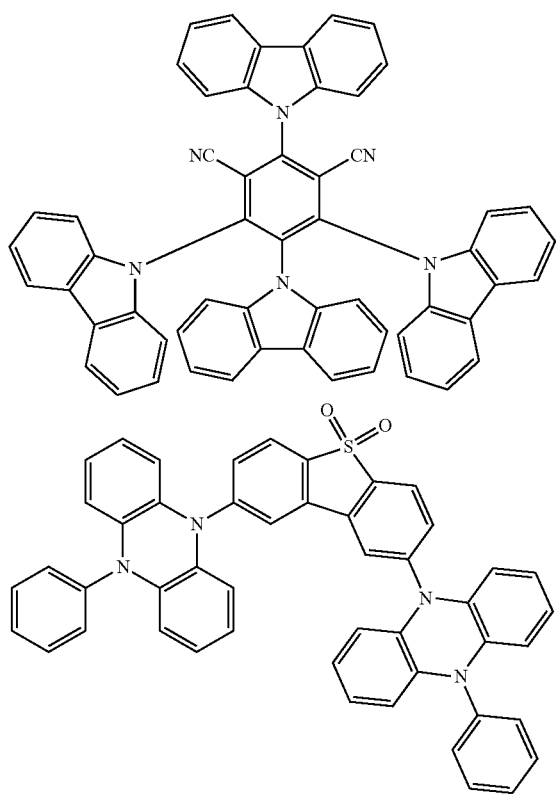

-continued

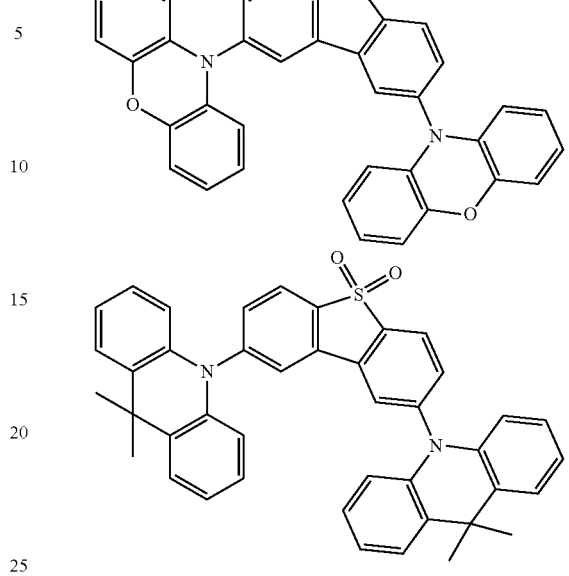

The light-emitting layer may incorporate a single thermally activated delayed fluorescence light-emitting dopant material or may incorporate two or more. The thermally activated delayed fluorescence light-emitting dopant may be used mixed with a phosphorescent light-emitting dopant and/or a fluorescent light-emitting dopant. The content of the thermally activated delayed fluorescence light-emitting dopant material with reference to the host material is preferably 0.1% to 50% and is more preferably 1% to 30%.

—Injection Layer—

The injection layer is a layer disposed between an electrode and the organic layer in order to lower the drive voltage and improve the luminance and may be a hole injection layer or an electron injection layer. It may be present between the anode and the light-emitting layer or hole transport layer and between the cathode and the light-emitting layer or electron transport layer. The injection layer may be provided on an optional basis.

—Hole Blocking Layer—

In a broad sense the hole blocking layer has the functionality of an electron transport layer and is composed of a hole blocking material that exhibits an electron transport functionality while having a very small hole transport capability. It can improve the probability of electron/hole recombination in the light-emitting layer by transporting electrons while blocking holes.

A known hole blocking layer material can be used for the hole blocking layer, but the incorporation of compounds with general formula (1) is preferred.

—Electron Blocking Layer—

In a broad sense the electron blocking layer has the functionality of a hole transport layer and, by transporting holes while blocking electrons, can improve the probability of electron/hole recombination in the light-emitting layer.

Known electron blocking layer materials can be used as the material of the electron blocking layer, and the hole transport layer materials described below can be used on an optional basis. The film thickness of the electron blocking layer is preferably 3 to 100 nm and is more preferably 5 to 30 nm.

—Exciton Blocking Layer—

The exciton blocking layer is a layer that blocks the diffusion, into a charge transport layer, of the excitons produced by hole/electron recombination in the light-emitting layer. The insertion of this layer enables the efficient confinement of the excitons within the light-emitting layer and can thus improve the emission efficiency of the element. In elements having two or more adjacent light-emitting layers, the exciton blocking layer may be inserted between two adjacent light-emitting layers.

A known exciton blocking layer material can be used as the material of the exciton blocking layer. Examples here are 1,3-dicarbazolylbenzene (mCP) and bis(2-methyl-8-quinolinolato)-4-phenylphenolatoaluminum(III) (BAlq).

—Hole Transport Layer—

The hole transport layer is composed of a hole transport material having a hole transport functionality, and a single hole transport layer may be disposed or a plurality of hole transport layers may be disposed.

The hole transport material may have a hole injection or transport capacity or an electron barrier behavior and may be organic or inorganic. Any compound selected from the heretofore known compounds may be used for the hole transport layer. The hole transport material can be exemplified by porphyrin derivatives, arylamine derivatives, triazole derivatives, oxadiazole derivatives, imidazole derivatives, polyarylalkane derivatives, pyrazoline derivatives and pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline copolymers, conductive polymer oligomers and particularly thiophene oligomers, and so forth. The use of porphyrin derivatives, arylamine derivatives, and styrylamine derivatives is preferred, and the use of arylamine compounds is more preferred.

—Electron Transport Layer—

The electron transport layer is composed of a material that has an electron transport functionality, and a single electron transport layer may be disposed or a plurality of electron transport layers may be disposed.

The electron transport material (which may also function as a hole blocking material) should function to transfer the electrons injected from the cathode to the light-emitting layer. Any compound selected from the heretofore known compounds may be used for the electron transport layer, for example, polycyclic aromatic derivatives of, e.g., naphthalene, anthracene, and phenanthroline; tris(8-quinolinolato)aluminum(III) derivatives; phosphine oxide derivatives; nitro-substituted fluorene derivatives; diphenylquinone derivatives; thiopyran dioxide derivatives; carbodiimide; fluorenylidenemethane derivatives; anthraquinodimethane and anthrone derivatives; bipyridine derivatives; quinoline derivatives; oxadiazole derivatives; benzimidazole derivatives; benzothiazole derivatives; and indolocarbazole derivatives. Polymer materials having the foregoing materials introduced in the polymer chain or having the foregoing materials as the polymer main chain may also be used.

EXAMPLES

The present invention is more particularly described in the following using examples; however, the present invention is not limited to or by these examples and can be executed using various embodiments insofar as its essential features are not exceeded.

Compound 1-11 (0.20 g) and compound 2-2 (0.80 g) were weighed out and a premix H1 was prepared by mixing while grinding with a mortar.

Premixes H2 to H9 were prepared in the same manner using the first host and second host given in Table 2.

The first host and second host and their blending ratio are given in Table 2. The compound numbers correspond to the numbers assigned to the exemplary compounds given above.

The chemical formula of the compound A used as the comparative host is given below.

[C23]

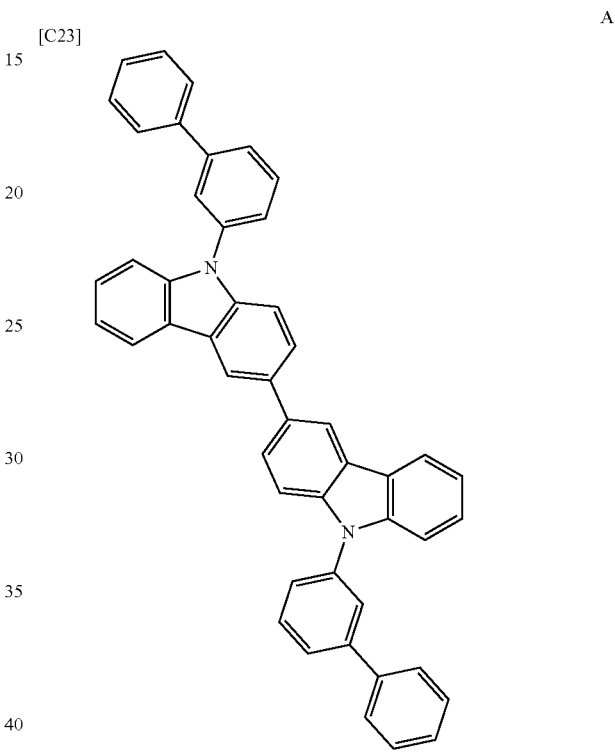

A

The 50% weight loss temperature ($T_{50}$) and the electron affinity (EA) of the compounds 1-1, 1-2, 1-3, 1-4, 1-11, 1-157, 2-2, 2-4, and compound A are given in Table 1.

TABLE 1

| compound | $T_{50}$ (° C.) | EA (eV) |
|---|---|---|
| 1-1 | 309 | 2.91 |
| 1-2 | 317 | 2.98 |
| 1-3 | 302 | 2.89 |
| 1-4 | 306 | 2.94 |
| 1-11 | 342 | 2.87 |
| 1-157 | 281 | 2.68 |
| 2-2 | 345 | 2.45 |
| 2-4 | 317 | 2.45 |
| A | 363 | 2.49 |

Example 1

Each thin film was layered by vacuum vapor deposition at a vacuum of $4.0 \times 10^{-5}$ Pa on a glass substrate on which an ITO anode had been formed in a film thickness of 110 nm. HAT-CN was first formed as a hole injection layer in a thickness of 25 nm on the ITO, followed by the formation of an NPD hole transport layer in a thickness of 30 nm. An HT-1 electron blocking layer was then formed in a thickness of 10 nm. The premix H1 as the host and Ir(ppy)$_3$ as the light-emitting dopant were subsequently co-vapor deposited from different vapor deposition sources to form a light-emitting layer with a thickness of 40 nm. This co-vapor deposition was carried out under vapor deposition conditions that provided an Ir(ppy)$_3$ concentration of 10 wt %. An ET-1 electron transport layer was then formed in a thickness of 20 nm. A 1 nm-thick lithium fluoride (LiF) electron injection layer was formed on the electron transport layer. Finally, a 70 nm-thick aluminum (Al) cathode was formed on the electron injection layer, thus fabricating an organic EL element.

Examples 2 to 9

Organic EL elements were fabricated proceeding as in Example 1, but respectively using each of the premixes H2 to H9 as the host in Example 1.

Example 10

An organic EL element was fabricated proceeding as in Example 3, except that, after the formation of the light-emitting layer in Example 3, compound 1-11 was formed in a thickness of 10 nm as a hole blocking layer and ET-1 was formed in a thickness of 10 nm as an electron transport layer.

Example 11

Each thin film was layered by vacuum vapor deposition at a vacuum of 4.0×10$^{-5}$ Pa on a glass substrate on which an ITO anode had been formed in a film thickness of 110 nm. HAT-CN was first formed as a hole injection layer in a thickness of 25 nm on the ITO, followed by the formation of an NPD hole transport layer in a thickness of 30 nm. An HT-1 electron blocking layer was then formed in a thickness of 10 nm. Compound 1-11 as the first host, compound 2-2 as the second host, and Ir(ppy)$_3$ as the light-emitting dopant were subsequently co-vapor deposited from different vapor deposition sources to form a light-emitting layer with a thickness of 40 nm. This co-vapor deposition was carried out under vapor deposition conditions that provided an Ir(ppy)$_3$ concentration of 10 wt % and a weight ratio between the first host and second host of 40:60. An ET-1 electron transport layer was then formed in a thickness of 20 nm. A 1 nm-thick LiF electron injection layer was formed on the electron transport layer. Finally, a 70 nm-thick Al cathode was formed on the electron injection layer, thus fabricating an organic EL element.

Example 12

An organic EL element was fabricated proceeding as in Example 11, but using compound 1-1 for the first host in Example 11 and using compound 2-2 for the second host.

Example 13

An organic EL element was fabricated proceeding as in Example 11, but using compound 1-2 for the first host in Example 11 and using compound 2-4 for the second host.

Example 14

An organic EL element was fabricated proceeding as in Example 11, but using compound 1-3 for the first host in Example 11 and using compound 2-4 for the second host.

Example 15

An organic EL element was fabricated proceeding as in Example 11, but using compound 1-157 for the first host in Example 11 and using compound 2-2 for the second host.

Example 16

Each thin film was layered by vacuum vapor deposition at a vacuum of 4.0×10$^{-5}$ Pa on a glass substrate on which an ITO anode had been formed in a film thickness of 110 nm. HAT-CN was first formed as a hole injection layer in a thickness of 25 nm on the ITO, followed by the formation of an NPD hole transport layer in a thickness of 45 nm. An HT-1 electron blocking layer was then formed in a thickness of 10 nm. The premix H2 as the host and Ir(piq)$_2$acac as the light-emitting dopant were co-vapor deposited from different vapor deposition sources to form a light-emitting layer with a thickness of 40 nm. This co-vapor deposition was carried out under vapor deposition conditions that provided an Ir(piq)$_2$acac concentration of 6.0 wt %. An ET-1 hole blocking layer was also formed in a thickness of 10 nm. An ET-1 electron transport layer was then formed in a thickness of 27.5 nm. A 1 nm-thick LiF electron injection layer was formed on the electron transport layer. Finally, a 70 nm-thick Al cathode was formed on the electron injection layer, thus fabricating an organic EL element.

Examples 17 and 18

Organic EL elements were fabricated proceeding as in Example 16, but respectively using each of the premixes H3 and H4 as the host in Example 16.

Example 19

An organic EL element was fabricated proceeding as in Example 17, except that, after the formation of the light-emitting layer in Example 17, compound 1-11 was formed in a thickness of 10 nm as a hole blocking layer and ET-1 was formed in a thickness of 10 nm as an electron transport layer.

Example 20

Each thin film was layered by vacuum vapor deposition at a vacuum of 4.0×10$^{-5}$ Pa on a glass substrate on which an ITO anode had been formed in a film thickness of 110 nm. HAT-CN was first formed as a hole injection layer in a thickness of 25 nm on the ITO, followed by the formation of an NPD hole transport layer in a thickness of 45 nm. An HT-1 electron blocking layer was then formed in a thickness of 10 nm. The compound 1-11 as the first host, the compound 2-2 as the second host, and Ir(piq)$_2$acac as the light-emitting dopant were co-vapor deposited from different vapor deposition sources to form a light-emitting layer with a thickness of 40 nm. This co-vapor deposition was carried out under vapor deposition conditions that provided an Ir(piq)$_2$acac concentration of 6.0 wt % and a weight ratio between the first host and second host of 30:70. An ET-1 hole blocking layer was also formed in a thickness of 10 nm. An ET-1 electron transport layer was then formed in a thickness of 27.5 nm. A 1 nm-thick LiF electron injection layer was formed on the electron transport layer. Finally, a 70 nm-thick Al cathode was formed on the electron injection layer, thus fabricating an organic EL element.

Example 21

An organic EL element was fabricated using the same conditions as in Example 20, with the exception that the co-vapor deposition of Example 20 was carried out under vapor deposition conditions that provided a weight ratio between the first host and the second host of 40:60.

Example 22

An organic EL element was fabricated using the same conditions as in Example 20, with the exception that the co-vapor deposition of Example 20 was carried out under vapor deposition conditions that provided a weight ratio between the first host and the second host of 50:50.

Comparative Example 1

An organic EL element was fabricated proceeding as in Example 1, but using the compound 1-11 by itself as the host in Example 1. The thickness of the light-emitting layer and the concentration of the light-emitting dopant were the same as in Example 1.

Comparative Examples 2 to 6

Organic EL elements were fabricated proceeding as in Comparative Example 1, but using the particular compound shown in Table 3 by itself as host.

Comparative Example 7

An organic EL element was fabricated proceeding as in Example 11, but using compound 1-11 for the first host in Example 11 and using compound A for the second host.

Comparative Example 8

An organic EL element was fabricated proceeding as in Example 11, but using 1-157 for the first host in Example 11 and using compound A for the second host.

Comparative Examples 9 and 10

Organic EL elements were fabricated proceeding as in Example 15, but using either the compound 1-2 by itself or the compound 1-11 by itself as the host in Example 15.
Compounds used in the examples are shown below.

[C24]

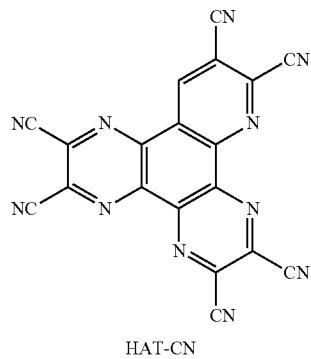

HAT-CN

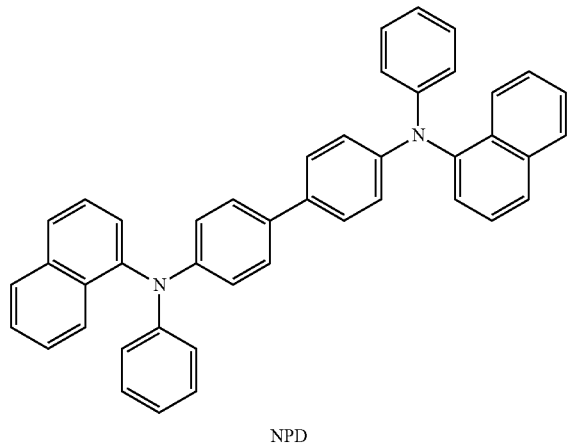

NPD

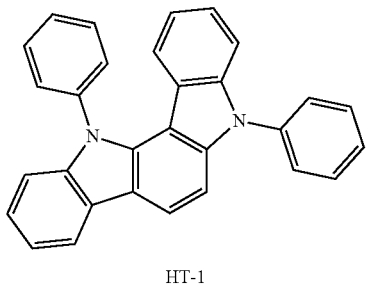

HT-1

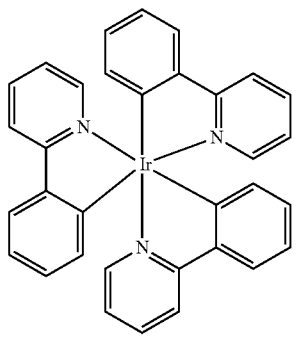

Ir(ppy)$_3$

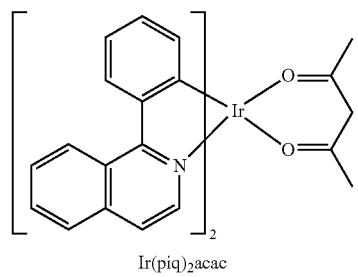

Ir(piq)$_2$acac

-continued

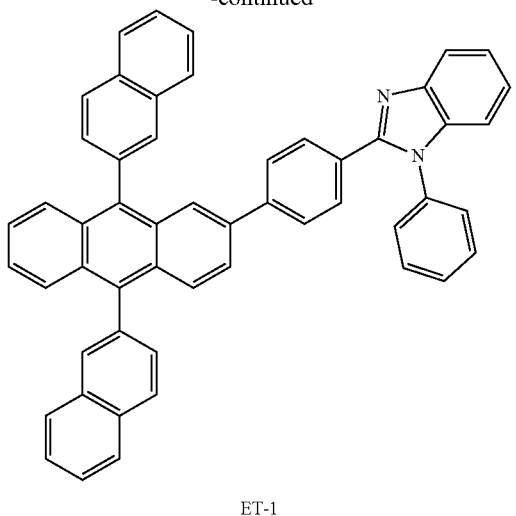

ET-1

Tables 2 and 3 give types of premixes of first and second hosts, and types and proportions of first hosts and second hosts.

TABLE 2

| example | premix | first host compound | second host compound |
|---|---|---|---|
| 1 | H1 | 1-11 (20%) | 2-2 (80%) |
| 2 | H2 | 1-11 (30%) | 2-2 (70%) |
| 3 | H3 | 1-11 (40%) | 2-2 (60%) |
| 4 | H4 | 1-11 (50%) | 2-2 (50%) |
| 5 | H5 | 1-11 (60%) | 2-2 (40%) |
| 6 | H6 | 1-1 (40%) | 2-4 (60%) |
| 7 | H7 | 1-1 (60%) | 2-4 (40%) |
| 8 | H8 | 1-2 (40%) | 2-4 (60%) |
| 9 | H9 | 1-2 (60%) | 2-4 (40%) |
| 10 | H3 | 1-11 (40%) | 2-2 (60%) |
| 11 | — | 1-11 (40%) | 2-2 (60%) |
| 12 | — | 1-1 (40%) | 2-2 (60%) |
| 13 | — | 1-2 (40%) | 2-4 (60%) |
| 14 | — | 1-3 (40%) | 2-4 (60%) |
| 15 | — | 1-157 (40%) | 2-2 (60%) |
| 16 | H2 | 1-11 (30%) | 2-2 (70%) |
| 17 | H3 | 1-11 (40%) | 2-2 (60%) |
| 18 | H4 | 1-11 (50%) | 2-2 (50%) |
| 19 | H3 | 1-11 (40%) | 2-2 (60%) |
| 20 | — | 1-11 (30%) | 2-2 (70%) |
| 21 | — | 1-11 (40%) | 2-2 (60%) |
| 22 | — | 1-11 (50%) | 2-2 (50%) |

TABLE 3

| comparative example | premix | first host compound | second host compound |
|---|---|---|---|
| 1 | — | 1-1 | — |
| 2 | — | 1-2 | — |
| 3 | — | 1-3 | — |
| 4 | — | 1-11 | — |
| 5 | — | — | 2-2 |
| 6 | — | — | 2-4 |
| 7 | — | 1-11 (40%) | A (60%) |
| 8 | — | 1-157 (40%) | A (60%) |
| 9 | — | 1-2 | — |
| 10 | — | 1-11 | — |

The organic EL elements fabricated in Examples 1 to 15 and Comparative Examples 1 to 8 were connected to an external power source and direct-current voltage was applied. In each instance, an emission spectrum with a maximum wavelength of 530 nm was observed, thus demonstrating that emission from the Ir(ppy)$_3$ was obtained.

In addition, the organic EL elements fabricated in Examples 16 to 22 and Comparative Examples 9 and 10 were connected to an external power source and direct-current voltage was applied. In each instance, an emission spectrum with a maximum wavelength of 620 nm was observed, thus demonstrating that emission from the Ir(pic)$_2$acac was obtained.

Tables 4 and 5 give the luminance, drive voltage, emission efficiency, and luminance half-life of the fabricated organic EL elements. The luminance, drive voltage, and emission efficiency in the tables are values for a drive current of 20 mA/cm$^2$ and are initial characteristics. The LT70 in Table 4 is the time required for the luminance to attenuate to 70% of the initial luminance for an initial luminance of 9000 cd/m$^2$, while the LT95 in Table 5 is the time required for the luminance to attenuate to 95% of the initial luminance for an initial luminance of 3700 cd/m$^2$. These are both life characteristics.

TABLE 4

| | luminance (cd/m$^2$) | voltage (V) | luminous efficacy (lm/W) | LT70 (h) |
|---|---|---|---|---|
| EX. 1 | 10100 | 4.9 | 32.5 | 880 |
| EX. 2 | 12100 | 4.5 | 42.6 | 1130 |
| EX. 3 | 13100 | 4.0 | 50.8 | 1230 |
| EX. 4 | 13300 | 3.8 | 54.4 | 1160 |
| EX. 5 | 13600 | 3.7 | 57.1 | 980 |
| EX. 6 | 10400 | 4.0 | 40.9 | 800 |
| EX. 7 | 10500 | 3.8 | 43.6 | 750 |
| EX. 8 | 12100 | 4.0 | 46.9 | 740 |
| EX. 9 | 12300 | 3.8 | 50.3 | 690 |
| EX. 10 | 13200 | 3.8 | 53.9 | 1360 |
| EX. 11 | 13300 | 4.0 | 51.6 | 1240 |
| EX. 12 | 12900 | 4.5 | 45.5 | 1220 |
| EX. 13 | 12200 | 3.8 | 49.9 | 880 |
| EX. 14 | 11000 | 3.6 | 47.4 | 870 |
| EX. 15 | 12000 | 3.7 | 50.9 | 1100 |
| Comp. EX. 1 | 11400 | 3.6 | 49.8 | 380 |
| Comp. EX. 2 | 13300 | 3.5 | 60.4 | 310 |
| Comp. EX. 3 | 10200 | 3.5 | 46.3 | 280 |
| Comp. EX. 4 | 13300 | 3.6 | 58.1 | 490 |
| Comp. EX. 5 | 1700 | 7.9 | 3.4 | 50 |
| Comp. EX. 6 | 1700 | 7.2 | 3.7 | 40 |
| Comp. EX. 7 | 9900 | 4.4 | 35.3 | 430 |
| Comp. EX. 8 | 10400 | 4.2 | 39.0 | 440 |

TABLE 5

| | luminance (cd/m$^2$) | voltage (V) | luminous efficacy (lm/W) | LT95 (h) |
|---|---|---|---|---|
| EX. 16 | 4600 | 4.4 | 16.6 | 420 |
| EX. 17 | 4300 | 4.0 | 16.7 | 360 |
| EX. 18 | 4100 | 3.7 | 17.2 | 310 |
| EX. 19 | 4400 | 3.8 | 18.0 | 400 |
| EX. 20 | 4400 | 4.6 | 15.1 | 370 |
| EX. 21 | 4200 | 4.2 | 15.5 | 320 |
| EX. 22 | 4000 | 3.9 | 16.0 | 280 |
| Comp. EX. 9 | 2200 | 2.8 | 12.3 | 20 |
| Comp. EX. 10 | 2400 | 3.1 | 12.2 | 30 |

As demonstrated by Tables 4 and 5, when a mixture of a first host represented by general formula (1) with a second host represented by general formula (2) is used, the life characteristics are significantly extended in comparison to the use of each individually. It is also demonstrated that, even for the use of a mixture of a first host and second host, when one is not a compound with general formula (1) or general formula (2), the luminous efficacy is low and excellent life characteristics are not obtained.

The life characteristics are also shown to be extended when a compound represented by general formula (1) is used as a hole blocking material as in Examples 10 and 19.

REFERENCE SIGNS LIST

1 Substrate
2 Anode
3 Hole injection layer
4 Hole transport layer
5 Light-emitting layer
6 Electron transport layer
7 Cathode

The invention claimed is:

1. A method for producing an organic electroluminescent element comprising one or more light-emitting layers between an anode and a cathode opposing each other, wherein at least one light-emitting layer is formed by vacuum vapor deposition and contains a first host selected from compounds represented by the following general formula (1), a second host selected from compounds represented by the following general formula (2), and a light-emitting dopant material;

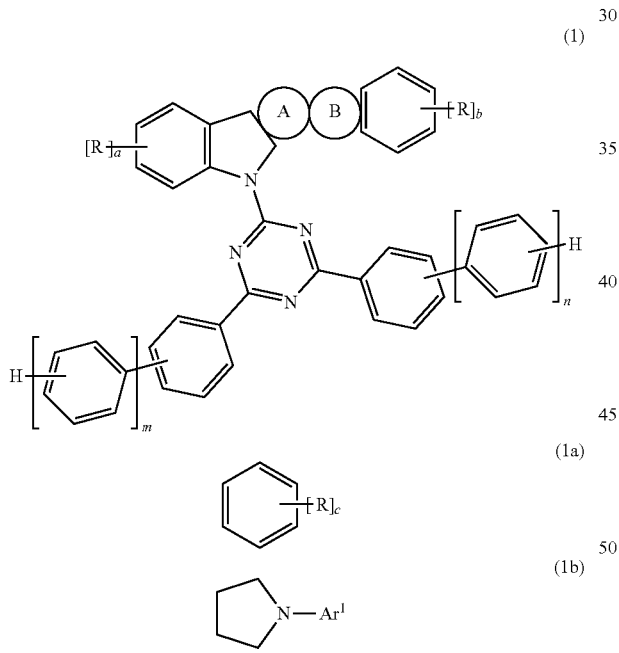

wherein, ring A is an aromatic hydrocarbon ring represented by formula (1a), ring B is a heterocycle represented by formula (1b), and ring A and ring B are each fused at any position with rings adjacent thereto;

$Ar^1$ is a phenyl group, a biphenyl group, or a terphenyl group;

each R is independently an aliphatic hydrocarbon group having 1 to 10 carbons, an aromatic hydrocarbon group having 6 to 10 carbons, or an aromatic heterocyclic group having 3 to 12 carbons;

a, b, and c each independently represent an integer of 0 to 3; and m and n each independently represent an integer of 0 to 2,

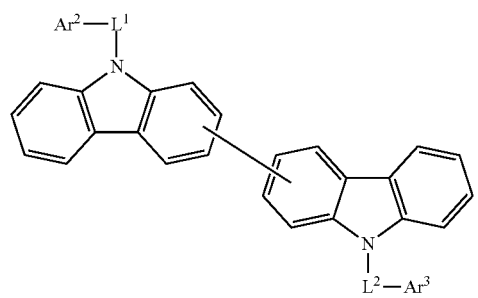

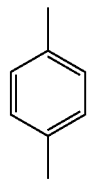

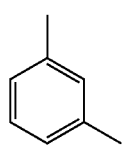

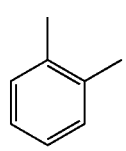

wherein, $Ar^2$ and $Ar^3$ represent an aromatic hydrocarbon group having 6 to 14 carbons or a group in which two of the aromatic hydrocarbon groups are linked to each other, wherein the two aromatic hydrocarbon groups linked to each other may be the same or may differ; $L^1$ represents a direct bond or a phenylene group of formula (2a), formula (2b), or formula (2c); and $L^2$ represents a phenylene group of formula (2c), the method comprising a step of forming a premix by mixing the first host with the second host and subsequently vapor depositing a host material containing this premix to form a light-emitting layer;

wherein the difference between the 50% weight loss temperatures of the first host and the second host is within 20° C.

2. The method for producing the organic electroluminescent element according to claim 1, wherein $Ar^3$ in general formula (2) is a phenyl group.

3. The method for producing the organic electroluminescent element according to claim 1, wherein the compound represented by general formula (2) is a compound represented by the following general formula (4):

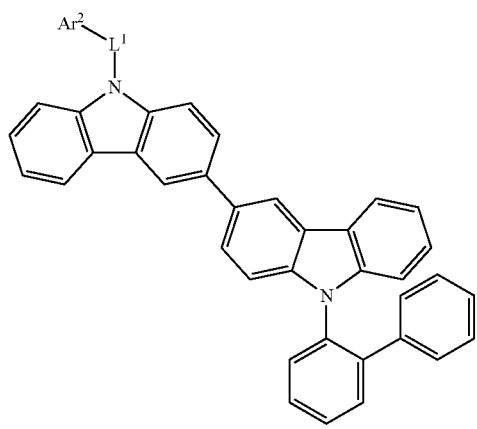

(4)

wherein, $Ar^2$ and $L^1$ are defined as for $Ar^2$ and $L^1$ of general formula (2).

4. The method for producing the organic electroluminescent element according to claim 1, wherein the proportion of the first host with reference to the sum of the first host and the second host is greater than 20 wt % and less than 55 wt %.

5. The method for producing the organic electroluminescent element according to claim 1, wherein the light-emitting dopant material is an organometal complex that contains at least one metal selected from the group consisting of ruthenium, rhodium, palladium, silver, rhenium, osmium, iridium, platinum, and gold.

6. The method for producing the organic electroluminescent element according to claim 1, wherein the light-emitting dopant material is a thermally activated delayed fluorescence light-emitting dopant material.

7. The method for producing the organic electroluminescent element according to claim 1, wherein the difference between the electron affinities (EA) of the first host and the second host is greater than 0.1 eV and less than 0.6 eV.

8. The method for producing the organic electroluminescent element according to claim 1, the organic electroluminescent element having a hole blocking layer adjacent to the light-emitting layer and containing a compound represented by general formula (1) in the hole blocking layer.

9. An organic electroluminescent element comprising one or more light-emitting layers between an anode and a cathode opposing each other, wherein at least one light-emitting layer is formed by vacuum vapor deposition and contains a first host selected from compounds represented by the following general formula (1), a second host selected from compounds represented by the following general formula (2), and a light-emitting dopant material;

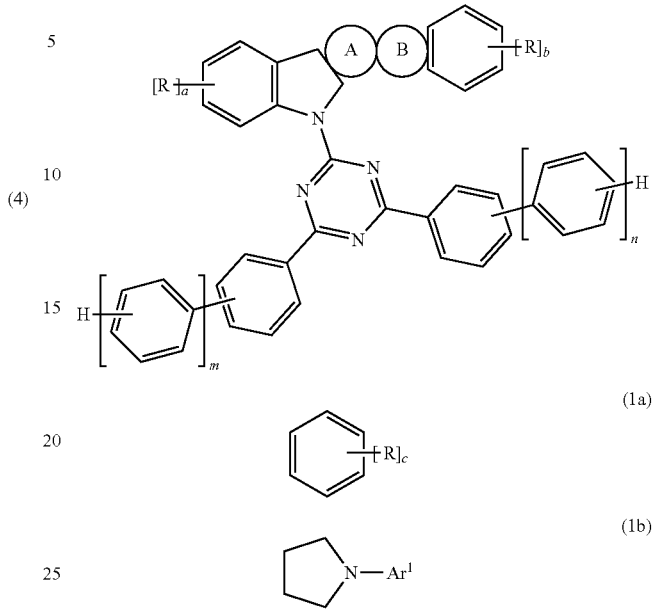

wherein, ring A is an aromatic hydrocarbon ring represented by formula (1a), ring B is a heterocycle represented by formula (1b), and ring A and ring B are each fused at any position with rings adjacent thereto;

$Ar^1$ is a phenyl group, a biphenyl group, or a terphenyl group;

each R is independently an aliphatic hydrocarbon group having 1 to 10 carbons, an aromatic hydrocarbon group having 6 to 10 carbons, or an aromatic heterocyclic group having 3 to 12 carbons;

a, b, and c each independently represent an integer of 0 to 3; and m and n each independently represent an integer of 0 to 2,

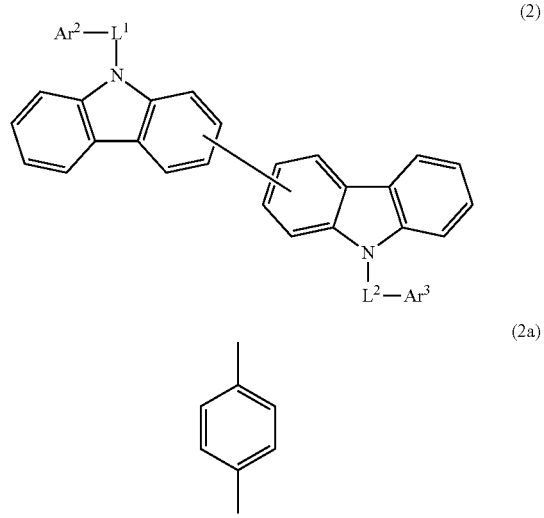

(2b)

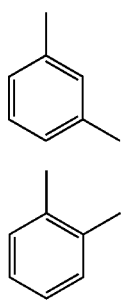

(2c)

wherein, Ar² and Ar³ represent an aromatic hydrocarbon group having 6 to 14 carbons or a group in which two of the aromatic hydrocarbon groups are linked to each other, wherein the two aromatic hydrocarbon groups linked to each other may be the same or may differ; $L^1$ represents a direct bond or a phenylene group of formula (2a), formula (2b), or formula (2c); and $L^2$ represents a phenylene group of formula (2c), wherein the difference between the 50% weight loss temperatures of the first host and the second host is within 20° C.

10. The organic electroluminescent element according to claim 9, wherein Ar³ in general formula (2) is a phenyl group.

11. The organic electroluminescent element according to claim 9, wherein the compound represented by general formula (2) is a compound represented by the following general formula (4):

(4)

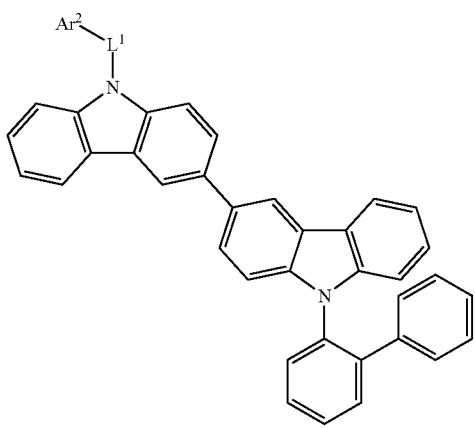

wherein, Ar² and $L^1$ are defined as for Ar² and $L^1$ of general formula (2).

12. The organic electroluminescent element according to claim 9, wherein the proportion of the first host with reference to the sum of the first host and the second host is greater than 20 wt % and less than 55 wt %.

13. The organic electroluminescent element according to claim 9, wherein the light-emitting dopant material is an organometal complex that contains at least one metal selected from the group consisting of ruthenium, rhodium, palladium, silver, rhenium, osmium, iridium, platinum, and gold.

14. The organic electroluminescent element according to claim 9, wherein the light-emitting dopant material is a thermally activated delayed fluorescence light-emitting dopant material.

15. The organic electroluminescent element according to claim 9, wherein the difference between the electron affinities (EA) of the first host and the second host is greater than 0.1 eV and less than 0.6 eV.

16. An organic electroluminescent element comprising one or more light-emitting layers between an anode and a cathode opposing each other, wherein at least one light-emitting layer is formed by vacuum vapor deposition and contains a first host selected from compounds represented by the following general formula (1), a second host selected from compounds represented by the following general formula (2), and a light-emitting dopant material;

(1)

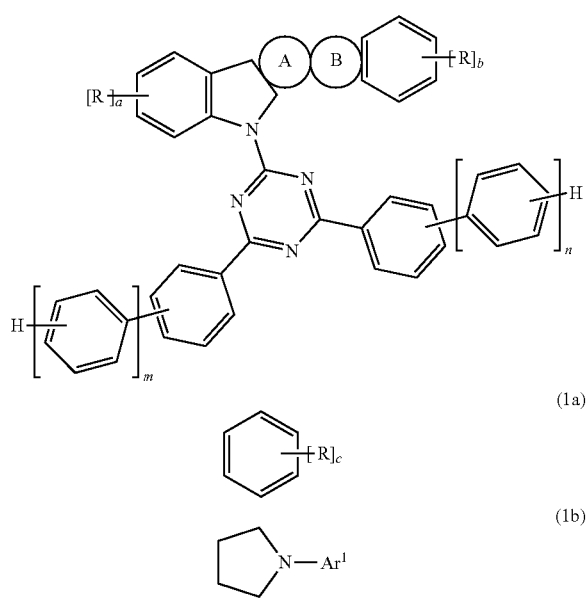

(1a)

(1b)

wherein, ring A is an aromatic hydrocarbon ring represented by formula (1a), ring B is a heterocycle represented by formula (1b), and ring A and ring B are each fused at any position with rings adjacent thereto;

Ar¹ is a phenyl group, a biphenyl group, or a terphenyl group;

each R is independently an aliphatic hydrocarbon group having 1 to 10 carbons, an aromatic hydrocarbon group having 6 to 10 carbons, or an aromatic heterocyclic group having 3 to 12 carbons;

a, b, and c each independently represent an integer of 0 to 3; and m and n each independently represent an integer of 0 to 2, (2)

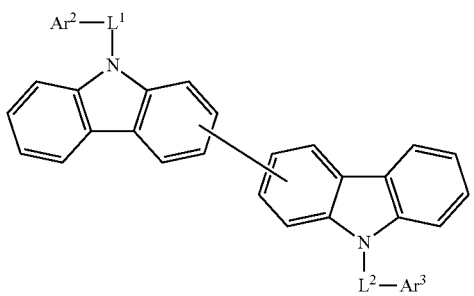

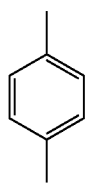
(2a)

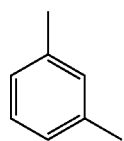
(2b)

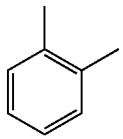
(2c)

wherein, $Ar^2$ and $Ar^3$ represent an aromatic hydrocarbon group having 6 to 14 carbons or a group in which two of the aromatic hydrocarbon groups are linked to each other, wherein the two aromatic hydrocarbon groups linked to each other may be the same or may differ; $L^1$ represents a direct bond or a phenylene group of formula (2a), formula (2b), or formula (2c); and $L^2$ represents a phenylene group of formula (2c), wherein a hole blocking layer is adjacent to the light-emitting layer and a compound represented by general formula (1) is in the hole blocking layer.

\* \* \* \* \*